US011285153B2

(12) United States Patent
Jin et al.

(10) Patent No.: US 11,285,153 B2
(45) Date of Patent: Mar. 29, 2022

(54) SUBSTITUTED PYRIMIDINE PIPERAZINE COMPOUND AND USE THEREOF

(71) Applicant: SUNSHINE LAKE PHARMA CO., LTD., Guangdong (CN)

(72) Inventors: Chuanfei Jin, Dongguan (CN); Wenhe Zhong, Dongguan (CN); Haiping Liang, Dongguan (CN); Yingjun Zhang, Dongguan (CN)

(73) Assignee: SUNSHINE LAKE PHARMA CO., LTD., Dongguan (CN)

(*) Notice: Subject to any disclaimer, the term of this patent is extended or adjusted under 35 U.S.C. 154(b) by 9 days.

(21) Appl. No.: 16/646,106

(22) PCT Filed: Sep. 21, 2018

(86) PCT No.: PCT/CN2018/106956
§ 371 (c)(1),
(2) Date: Mar. 10, 2020

(87) PCT Pub. No.: WO2019/062662
PCT Pub. Date: Apr. 4, 2019

(65) Prior Publication Data
US 2020/0276196 A1 Sep. 3, 2020

(30) Foreign Application Priority Data
Sep. 29, 2017 (CN) .......................... 201710902245.7

(51) Int. Cl.
A61K 31/496 (2006.01)
A61K 31/198 (2006.01)
A61K 31/495 (2006.01)
A61K 31/05 (2006.01)
A61K 31/55 (2006.01)
A61P 25/16 (2006.01)
A61K 31/506 (2006.01)
A61K 45/06 (2006.01)
C07D 401/14 (2006.01)
C07D 403/14 (2006.01)

(52) U.S. Cl.
CPC ............ A61K 31/506 (2013.01); A61K 45/06 (2013.01); C07D 401/14 (2013.01); C07D 403/14 (2013.01)

(58) Field of Classification Search
CPC .... A61K 31/506; A61K 45/06; C07D 401/14; C07D 403/06
See application file for complete search history.

(56) References Cited

U.S. PATENT DOCUMENTS

| 4,954,502 A | 9/1990 | Smith et al. |
| 5,077,293 A | 12/1991 | Smith et al. |
| 5,532,241 A | 7/1996 | Bottcher et al. |
| 6,310,068 B1 | 10/2001 | Bottcher et al. |
| 6,699,864 B2 | 3/2004 | Ruhland et al. |
| 7,572,796 B2 | 8/2009 | Schadt et al. |
| 7,829,565 B2 | 11/2010 | Heinrich et al. |
| 9,598,401 B2 | 3/2017 | Zhang et al. |
| 9,714,232 B2 | 7/2017 | Zhang et al. |
| 10,316,015 B2 | 6/2019 | Ben Haim et al. |
| 10,316,025 B2 * | 6/2019 | Zhang ................. C07D 403/12 |
| 2006/0122191 A1 | 6/2006 | Heinrich et al. |

(Continued)

FOREIGN PATENT DOCUMENTS

| CN | 104163813 A | 11/2014 |
| CN | 104418842 A | 3/2015 |

(Continued)

OTHER PUBLICATIONS

Pessoa-Mahana et al., "Synthesis 5-Hydroxytryptamine1A Receptor Affinity and Docking Studies of 3-[3-(4-Aryl-1-piperazinyl)-propy]-1H-Indole Derivatives," Chem. Pharm. Bull., 2012, vol. 60, No. 5, pp. 632-638.

Dec. 27, 2018 International Search Report issued in International Patent Application No. PCT/CN2018/106956.

Dec. 27, 2018 Written Opinion of the International Searching Authority issued in International Patent Application No. PCT/CN2018/106956.

Apr. 20, 2021 Extended European Search Report issued in European Patent Application No. 18863238.4.

(Continued)

Primary Examiner — Tracy Vivlemore
Assistant Examiner — Ebenezer O Sackey
(74) Attorney, Agent, or Firm — Oliff PLC

(57) ABSTRACT

A substituted pyrimidine piperazine compound and uses thereof, and a pharmaceutical composition containing the compound and uses thereof. Wherein the compound has Formula (I), or a stereoisomer, a geometric isomer, a tautomer, an N-oxide, a hydrate, a solvate, a metabolite, a pharmaceutically acceptable salt or a prodrug thereof. The substituted pyrimidine piperazine compound and the pharmaceutical composition containing the compound can be used to inhibit 5-hydroxytryptamine reuptake and/or activate the 5-HT$_{1A}$ receptors. Also, a method of preparing such compounds and pharmaceutical compositions, and uses thereof in the treatment of central nervous system dysfunction.

(I)

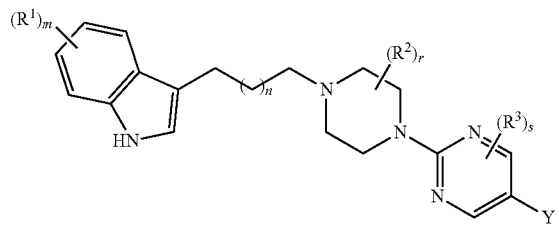

19 Claims, No Drawings

(56) References Cited

U.S. PATENT DOCUMENTS

| | | |
|---|---|---|
| 2006/0160824 A1 | 7/2006 | Heinrich et al. |
| 2010/0190768 A1 | 7/2010 | Sone et al. |
| 2011/0059982 A1 | 3/2011 | Heinrich et al. |
| 2013/0064770 A1 | 3/2013 | Newington et al. |

FOREIGN PATENT DOCUMENTS

| | | |
|---|---|---|
| CN | 104725359 A | 6/2015 |
| CN | 104725363 A | 6/2015 |
| CN | 105085491 A | 11/2015 |
| CN | 106065018 A | 11/2016 |
| WO | 95/35293 A1 | 12/1995 |
| WO | 97/36898 A1 | 10/1997 |
| WO | 2004/041815 A1 | 5/2004 |
| WO | 2015/169180 A1 | 11/2015 |
| WO | 2016/107603 A1 | 7/2016 |
| WO | 2016192657 | * 12/2016 |
| WO | 2017/025058 A1 | 2/2017 |

* cited by examiner

SUBSTITUTED PYRIMIDINE PIPERAZINE COMPOUND AND USE THEREOF

CROSS-REFERENCE TO RELATED APPLICATIONS

This is a U.S. national stage application of the International Patent Application No. PCT/CN2018/106956, filed Sep. 21, 2018, which claims priority to Chinese Patent Application No. 201710902245.7, filed Sep. 29, 2017, both of which are incorporated hereinby reference in their entirety.

FIELD OF THE INVENTION

The invention relates to the technical field of medicine, in particular to a compound or a composition for treating central nervous system dysfunction and usage and use thereof. Particularly, provided herein is a substituted pyrimidine piperazine compound which may act as a 5-hydroxytryptamine reuptake inhibitor and/or 5-$HT_{1A}$ receptor agonist.

BACKGROUND ART

5-Hydroxytryptamine (5-HT), which is a neurotransmitter that transmits signals between the brain and nervous system in the central nervous system (CNS) dysfunction, especially anxiety, depression, aggression, and impulsive mood, plays an important role. Antagonizing or activating certain types of 5-hydroxytryptamine receptors can effectively modulate central nervous system dysfunction. To date, at least 14 kinds of 5-hydroxytryptamine receptors have been identified. These receptors can be classified into different families, which are recorded as 5-$HT_1$, 5-$HT_2$, 5-$HT_3$, 5-$HT_4$, 5-$HT_5$, 5-$HT_6$ and 5-$HT_7$ respectively. The different subtypes of each family are distinguished by a, b and c. The 5-hydroxytryptamine neurons of the central nervous system are located in the raphe nucleus of the brainstem. The 5-$HT_{1A}$ receptor, a G-protein coupled receptor, is widely distributed in the regions that receive 5-hydroxytryptamine derived from the raphe nucleus, including frontal cortex, lateral septum, amygdala, hippocampus, and hypothalamus. In these cortical border regions, 5-$HT_{1A}$ is located in the postsynaptic membrane. At the same time, the 5-$HT_{1A}$ receptor is also a presynaptic membrane autoreceptor on the raphe nucleus, which can reduce discharge rate of neurons (ie, the amount of 5-hydroxytryptamine released per action potential), and the synthesis of neurotransmitters, thereby reducing the activity of 5-hydroxytryptamine in the projection zone. Activating the the 5-$HT_{1A}$ receptor on the presynaptic membrane can inhibit the synthesis of tyrosine hydroxylase and the activity of the glutamate channel (produced in the medial prefrontal cortex and directed to the raphe nucleus), thereby indirectly reducing the transport of 5-hydroxytryptamine (Jonathan Savitz, Irwin Lucki, Wayne C. Drevets. 5-$HT_{1A}$ receptor function in major depressive disorder. Prog Neurobiol. 2009, 88(1): 17-31).

Of all the indications associated with 5-hydroxytryptamine dysfunction, depression is the most important. As the World Health Organization reports that depression has become the fourth burdensome disease in humans. It is estimated that the disability adjusted life years of depression will leap to the second place in all diseases by 2020. (Bromet E, Andrade L H, Hwang I, et al., Cross-national epidemiology of DSM-IV major depressive episode. BMC Med. 2011, 9: 90).

Historically, medications for mood disorders began in the 1950s, including tricyclic antidepressants (TCAs) and monoamine oxidase inhibitors (MAOIs). These medicines work by blocking neurotransmitters (dopamine, norepinephrine, and 5-hydroxytryptamine). However, the non selective and undesirable side effects to the targets limit their use. By the 1980s, the emergence of selective 5-hydroxytryptamine reuptake inhibitors (SSRIs) changed this situation. Compared with TCAs, these drugs are equally effective, but with few side effects. Even if taken in excess, the toxicity is small (Sarko J. Andidepressant, old and new. A review of their adverse effects and toxicity in overdose. Emerg Med Clin North Am, 2000, 18 (4): 637-54).

Traditional SSRIs treatment increases the content of 5-hydroxytryptamine by inhibiting the reuptake of 5-hydroxytryptamine and regulating its transport. However, the use of SSRIs also activates the 5-$HT_{1A}$ autoreceptors of the presynaptic membrane, resulting in a decrease in the release of 5-hydroxytryptamine and a decrease in the concentration of 5-hydroxytryptamine in the synaptic cleft. However, as the time of administration increasing, SSRIs can cause desensitization of 5-$HT_{1A}$ autoreceptors, and the activation effect is restrained, thereby exerting a normal regulatory effect. It is concluded that the activation effect of 5-$HT_{1A}$ autoreceptors is an important reason for delaying the efficacy of SSRIs (Celada P, Puig M, Amargos-Bosch M, et al., The therapeutic role of 5-$HT_{1A}$ and 5-$HT_{2A}$ receptors in depression. J Psychiatry Neurosci, 2004, 29(4): 252-65). Therefore, overcoming the negative feedback effect of 5-$HT_{1A}$ autoreceptor antagonists has the prospect of enhancing and accelerating clinical anti-depression.

In contrast to SSRIs, 5-$HT_{1A}$ receptor agonists or partial agonists directly act on the postsynaptic 5-hydroxytryptamine receptors, for increasing neurotransmission of 5-hydroxytryptamine during the latency of SSRIs. Feiger and Wilcox demonstrated that buspirone and gepirone were clinically effective 5-$HT_{1A}$ partial agonists (Feiger, A. Psychopharmacol. Bull. 1996, 32: 659-65). The addition of buspirone to standard SSRIs treatments resulted in significant improvements in patients who had previously not responded to standard treatment for depression (Dimitriou, E. J. Clin. Psychopharmacol., 1998, 18: 465-9).

SUMMARY OF THE INVENTION

The present invention provides a novel compound having selective 5-hydroxytryptamine reuptake inhibitory activity and/or 5-$HT_{1A}$ receptor agonistic activity, and which has a good clinical application prospect. The compound provided herein has better pharmacodynamics, pharmacokinetics and/or toxicology properties than the existing similar compound.

The present invention relates to a novel substituted pyrimidine piperazine compound, which has strong binding affinity with 5-HT transporter (SERT) and selectively inhibits reuptake of 5-HT, and has strong binding affinity to 5-$HT_{1A}$ receptors and can effectively activate 5-$HT_{1A}$ receptors, so it can be used to prepare drugs for treating central nervous system (CNS) dysfunction. The compound of the present invention has stable properties, good safety, advantages of pharmacodynamics and pharmacokinetics, such as good brain plasma ratio, good bioavailability or good metabolic stability, so it has a good clinical application prospect.

The following is a general description of some aspects of the invention, which is not limited to this. These aspects and other parts will be more completely explained later. All references of this specification are incorporated herein by reference in their entirety. In the event that the disclosures of the specification are different from the cited references, the disclosures of this specification will be shall control.

The present invention provides a novel compound which can selectively inhibit reuptake of 5-hydroxytryptamine and/or activate the 5-HT$_{1A}$ receptors. They can be used to prepare drugs for the treatment of central nervous system (CNS) dysfunction, such as depression, anxiety disorder, bipolar disorder.

The invention also provides a method for preparing the compound and pharmaceutical compositions thereof.

In one aspect, the present invention provides a compound having Formula (I) or a stereoisomer, a geometric isomer, a tautomer, an N-oxide, a hydrate, a solvate, a metabolite, a pharmaceutically acceptable salt or a prodrug thereof,

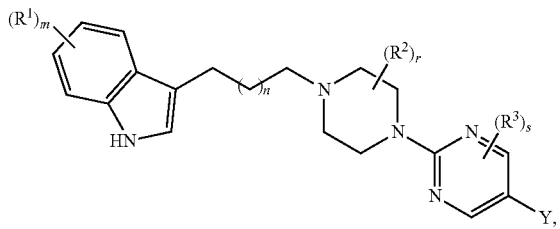

(I)

wherein

Y is $C_3$-$C_{10}$ cycloalkyl, 3-10 membered heterocyclyl or 5-10 membered heteroaryl, wherein optionally each of the $C_3$-$C_{10}$ cycloalkyl, 3-10 membered heterocyclyl, and 5-10 membered heteroaryl is independently substituted with one or more $R^x$;

each $R^x$ is independently H, D, F, Cl, Br, I, nitro, cyano, —NR$^a$R$^b$, —OR$^c$, —SR$^c$, —C(=O)R$^d$, —C(=O)OR$^c$, —C(=O)NR$^a$R$^b$, —OC(=O)R$^d$, —N(R$^a$)C(=O)R$^d$, —S(=O)R$^d$, —S(=O)$_2$R$^d$, —S(=O)$_2$OR$^c$, —S(=O)$_2$NR$^a$R$^b$, —N(R$^a$)S(=O)$_2$R$^d$, —N(R$^a$)C(=O)OR$^c$, —N(R$^a$)C(=O)NR$^a$R$^b$, $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, ($C_3$-$C_{10}$ cycloalkyl)-($C_1$-$C_6$ alkylene)-, 3-10 membered heterocyclyl, (3-10 membered heterocyclyl)-($C_1$-$C_6$ alkylene-, $C_6$-$C_{10}$ aryl, ($C_6$-$C_{10}$ aryl)-($C_1$-$C_6$ alkylene)-, 5-10 membered heteroaryl or (5-10 membered heteroaryl)-($C_1$-$C_6$ alkylene)-, wherein optionally each of the —NR$^a$R$^b$, —OR$^c$, —SR$^c$, —C(=O)R$^d$, —C(=O)OR$^c$, —C(=O)NR$^a$R$^b$, —OC(=O)R$^d$, —N(R$^a$)C(=O)R$^d$, —S(=O)R$^d$, —S(=O)$_2$R$^d$, —S(=O)$_2$OR$^c$, —S(=O)$_2$NR$^a$R$^b$, —N(R$^a$)S(=O)$_2$R$^d$, —N(R$^a$)C(=O)OR$^c$, —N(R$^a$)C(=O)NR$^a$R$^b$, $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, ($C_3$-$C_{10}$ cycloalkyl)-($C_1$-$C_6$ alkylene)-, 3-10 membered heterocyclyl, (3-10 membered heterocyclyl)-($C_1$-$C_6$ alkylene)-, $C_6$-$C_{10}$ aryl, ($C_6$-$C_{10}$ aryl)-($C_1$-$C_6$ alkylene)-, 5-10 membered heteroaryl or (5-10 membered heteroaryl)-($C_1$-$C_6$ alkylene)- is independently substituted with one or more $R^4$;

each $R^4$ is independently F, Cl, Br, I, nitro, cyano, azide, amino, hydroxy, sulfydryl, $C_1$-$C_4$ alkyl, $C_2$-$C_6$ alkenyl, $C_2$-$C_6$ alkynyl, $C_1$-$C_4$ haloalkyl, $C_1$-$C_4$ alkoxy, $C_1$-$C_4$ haloalkoxy, $C_1$-$C_4$ alkylamino, $C_1$-$C_4$ alkylthio, amino-($C_1$-$C_4$ alkylene)-, hydroxy-($C_1$-$C_4$ alkylene)-, sulfydryl-($C_1$-$C_4$ alkylene)-, ($C_1$-$C_4$ alkylamino)-($C_1$-$C_4$ alkylene)-, ($C_1$-$C_4$ alkoxy)-($C_1$-$C_4$ alkylene)-, ($C_1$-$C_4$ alkylthio)-($C_1$-$C_4$ alkylene)-, $C_3$-$C_6$ cycloalkyl, ($C_3$-$C_6$ cycloalkyl)-($C_1$-$C_4$ alkylene)-, 3-7 membered heterocyclyl, (3-7 membered heterocyclyl)-($C_1$-$C_4$ alkylene)-, phenyl, phenyl-($C_1$-$C_4$ alkylene)-, 5-6 membered heteroaryl or (5-6 membered heteroaryl)-($C_1$-$C_4$ alkylene)-;

each $R^1$ is independently H, D, F, Cl, Br, I, nitro, cyano, amino, hydroxy, sulfydryl, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, ($C_1$-$C_6$ alkoxy)-($C_1$-$C_4$ alkylene)-, $C_1$-$C_6$ alkylamino, ($C_1$-$C_6$ alkylamino)-($C_1$-$C_4$ alkylene)-, $C_1$-$C_6$ alkylthio or ($C_1$-$C_6$ alkylthio)-($C_1$-$C_4$ alkylene)-;

each $R^2$ is independently H, D, F, Cl, Br, I, $C_1$-$C_6$ alkyl, $C_1$-$C_6$ haloalkyl, —NR$^a$R$^b$, —OR$^c$, —C(=O)R$^d$, —C(=O)OR$^c$, —C(=O)NR$^a$R$^b$ or ($C_6$-$C_{10}$ aryl)-($C_1$-$C_6$ alkylene)-, or two $R^2$ of adjacent carbon atoms, together with the carbon atom they are attached to, form a $C_3$-$C_6$ carbocycle, a benzene ring, a 3-7 membered heterocyclyl ring or a 5-6 membered heteroaryl ring, or two $R^2$ of the same carbon atom, together with the carbon atom they are attached to together, form a $C_3$-$C_6$ carbocycle or a 3-7 membered heterocyclyl ring;

each $R^3$ is independently H, D, F, Cl, Br, I, nitro, cyano, amino, hydroxy, sulfydryl, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, ($C_1$-$C_6$ alkoxy)-($C_1$-$C_4$ alkylene)-, $C_1$-$C_6$ alkylamino, ($C_1$-$C_6$ alkylamino)-($C_1$-$C_4$ alkylene)-, $C_1$-$C_6$ alkylthio or ($C_1$-$C_6$ alkythio)-($C_1$-$C_4$ alkylene)-;

each $R^a$ and $R^b$ is independently H, $C_1$-$C_6$ alkyl, $C_3$-$C_6$ alkenyl, $C_3$-$C_6$ alkynyl, $C_1$-$C_6$ haloalkyl, $C_3$-$C_6$ cycloalkyl, ($C_3$-$C_6$ cycloalkyl)-($C_1$-$C_4$ alkylene)-, 3-7 membered heterocyclyl, (3-7 membered heterocyclyl)-($C_1$-$C_4$ alkylene)-, phenyl, phenyl-($C_1$-$C_4$ alkylene)-, 5-6 membered heteroaryl and (5-6 membered heteroaryl)-($C_1$-$C_4$ alkylene)-, or $R^a$ and $R^b$ together with the nitrogen atom they are attached to together, form a 3-7 membered heterocyclyl ring;

each $R^c$ and $R^d$ is independently H, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, ($C_3$-$C_6$ cycloalkyl)-($C_1$-$C_4$ alkylene)-, 3-7 membered heterocyclyl, (3-7 membered heterocyclyl)-($C_1$-$C_4$ alkylene)-, phenyl, phenyl-($C_1$-$C_4$ alkylene)-, 5-6 membered heteroaryl or (5-6 membered heteroaryl)-($C_1$-$C_4$ alkylene)-;

m is 0, 1, 2, 3 or 4;

n is 0, 1, 2, 3 or 4;

r is 0, 1, 2, 3, 4, 5 or 6; and s is 0, 1 or 2.

In some embodiments, Y is $C_3$-$C_6$ cycloalkyl, 3-6 membered heterocyclyl or 5-6 membered heteroaryl, wherein optionally each of the $C_3$-$C_6$ cycloalkyl, 3-6 membered heterocyclyl, and 5-6 membered heteroaryl is independently substituted with one or more $R^x$.

In other embodiments, Y is one of the substructures of Formulae (Y-1) to (Y-15):

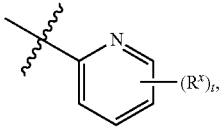

(Y-1)

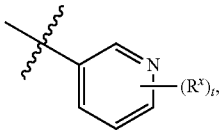

(Y-2)

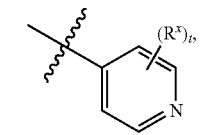

(Y-3)

(Y-4) 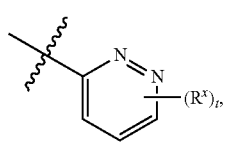
(Y-5) 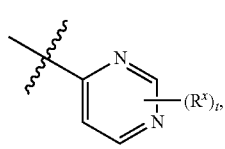
(Y-6) 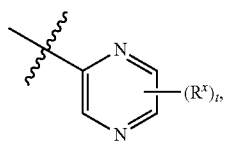
(Y-7) 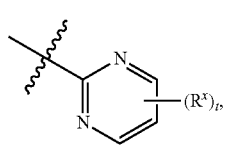
(Y-8) 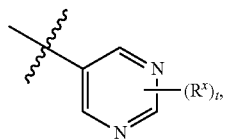
(Y-9) 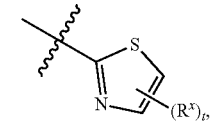
(Y-10) 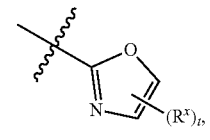
(Y-11) 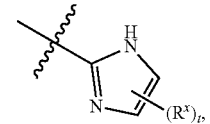
(Y-12) 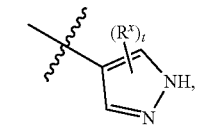
(Y-13) 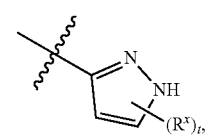
(Y-14) 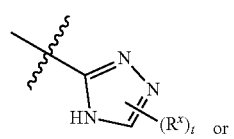 or
(Y-15) 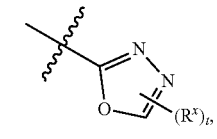
wherein each t is independently 1, 2, 3 or 4; and each $R^x$ is as defined herein.
In some embodiments, provided herein is a compound having formula (VI), (VII), (VIII) or (IX) or a stereoisomer, a geometric isomer, a tautomer, an N-oxide, a hydrate, a solvate, a metabolite, a pharmaceutically acceptable salt or a prodrug thereof,
(VI) 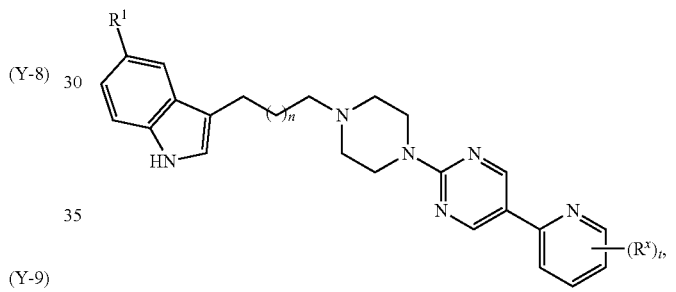
(VII) 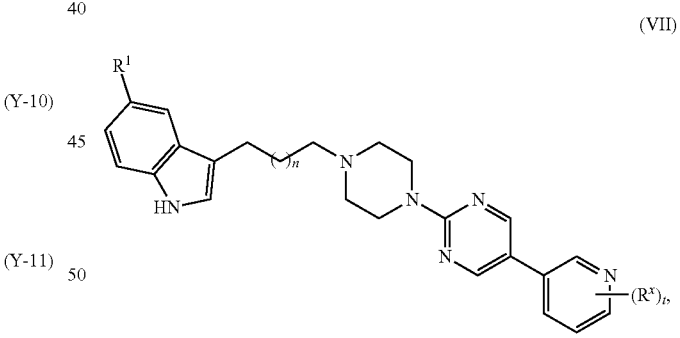
(VIII) 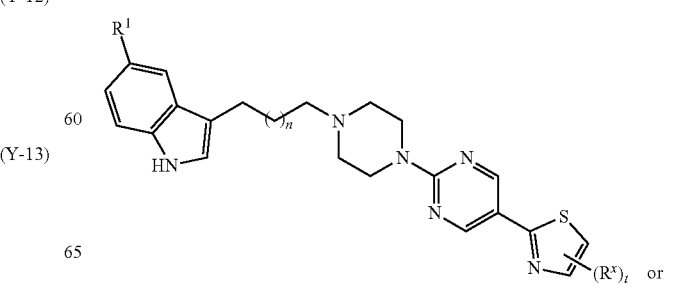 or -continued (IX)

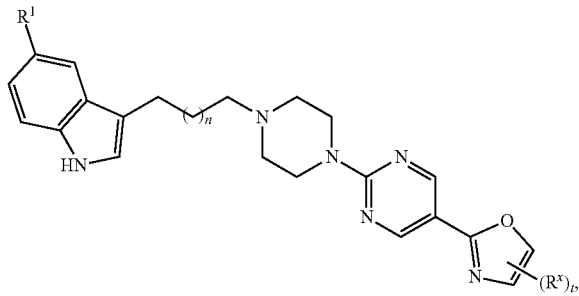

wherein each t is independently 1, 2, 3 or 4; and
$R^1$, $R^x$ and n are as defined herein.

In some embodiments, each $R^1$ is independently H, D, F, Cl, Br, I, cyano, nitro, amino, —NMe$_2$, hydroxy, —OMe, —OEt, —O(i-Pr), —O(t-Bu), methyl, ethyl, -(n-Pr), -(i-Pr), -(t-Bu) or —CF$_3$.

In some embodiments, each $R^2$ is independently H, D, F, Cl, Br, I, amino, hydroxy, methyl, ethyl, -(n-Pr), -(i-Pr), -(t-Bu) or —CF$_3$, —OMe, —OEt, —O(i-Pr) or —O(t-Bu).

In some embodiments, each $R_3$ is independently H, D, F, Cl, Br, I, cyano, nitro, amino, —NMe$_2$, hydroxy, —OMe, —OEt, —O(i-Pr), —O(t-Bu), methyl, ethyl, -(n-Pr), -(i-Pr), -(t-Bu) or —CF$_3$.

In some embodiments, each $R^x$ is independently H, D, F, Cl, Br, I, cyano, nitro, amino, —NMe$_2$, —NHEt, —NEt$_2$, hydroxy, —OMe, —OEt, —O(n-Pr), —O(i-Pr), —O(t-Bu), methyl, ethyl, -(n-Pr), -(i-Pr), -(t-Bu), —CF$_3$, —CH$_2$CH$_2$Cl, —OCHF$_2$, —OCF$_3$, —OCH$_2$CF$_3$, —OCF$_2$CHF$_2$, —OCHFCF$_3$, —OCF$_2$CF$_3$, —OCF$_2$CH$_2$CH$_3$, —OCF$_2$CH$_2$CF$_3$, —OCF$_2$CH$_2$CHF$_2$, —OCH$_2$CHFCH$_3$, —OCH$_2$CF$_2$CH$_3$, —OCH$_2$CF$_2$CF$_3$, —OCH$_2$CF$_2$CHF$_2$, —CONH$_2$, —CONHMe, —CONMe$_2$, —C(=O)OMe, —C(=O)OEt, —NHC(=O)H, —NHC(=O)CH$_3$, —NHC(=O)OMe or phenyl.

In some embodiments, each $R^a$ and $R^b$ is independently H, C$_1$-C$_4$ alkyl, C$_3$-C$_4$ alkenyl, C$_3$-C$_4$ alkynyl, C$_1$-C$_4$ haloalkyl, C$_5$-C$_6$ cycloalkyl, (C$_5$-C$_6$ cycloalkyl)-(C$_1$-C$_4$ alkylene)-, 5-7 membered heterocyclyl, (5-7 membered heterocyclyl)-(C$_1$-C$_4$ alkylene)-, phenyl, phenyl-(C$_1$-C$_4$ alkylene)-, 5-6 membered heteroaryl and (5-6 membered heteroaryl)-(C$_1$-C$_4$ alkylene)-, or $R^a$ and $R^b$ together with the nitrogen atom they are attached to, form a 5-7 membered heterocyclyl; and each $R^c$ and $R^d$ is independently H, C$_1$-C$_4$ alkyl, C$_2$-C$_4$ alkenyl, C$_2$-C$_4$ alkynyl, C$_1$-C$_4$ haloalkyl, C$_5$-C$_6$ cycloalkyl, (C$_5$-C$_6$ cycloalkyl)-(C$_1$-C$_4$ alkylene)-, 5-7 membered heterocyclyl, (5-7 membered heterocyclyl)-(C$_1$-C$_4$ alkylene)-, phenyl, phenyl-(C$_1$-C$_4$ alkylene)-, 5-6 membered heteroaryl and (5-6 membered heteroaryl)-(C$_1$-C$_4$ alkylene)-.

In other embodiments, each $R^a$ and $R^b$ is independently H, methyl, ethyl, -(n-Pr), -(i-Pr), -(t-Bu), —CHF$_2$, —CF$_3$, —CH$_2$CF$_3$, —CF$_2$CHF$_2$, —CHFCF$_3$, —CF$_2$CF$_3$, —CF$_2$CH$_2$CH$_3$, —CF$_2$CH$_2$CF$_3$, —CF$_2$CH$_2$CHF$_2$, —CH$_2$CHFCH$_3$, —CH$_2$CF$_2$CH$_3$, —CH$_2$CF$_2$CF$_3$, —CH$_2$CF$_2$CHF$_2$, —CH$_2$CH$_2$Cl, cyclopentyl, pyrrolidinyl, piperidinyl, morpholinyl or piperazinyl, or $R^a$ and $R^b$, together with the nitrogen atom they are attached to together, form a 5-6 membered heterocyclyl ring; and each $R^c$ and $R^d$ is independently H, methyl, ethyl, -(n-Pr), -(i-Pr), -(t-Bu), —CHF$_2$, —CF$_3$, —CH$_2$CF$_3$, —CF$_2$CHF$_2$, —CHFCF$_3$, —CF$_2$CF$_3$, —CF$_2$CH$_2$CH$_3$, —CF$_2$CH$_2$CF$_3$, —CF$_2$CH$_2$CHF$_2$, —CH$_2$CHFCH$_3$, —CH$_2$CF$_2$CH$_3$, —CH$_2$CF$_2$CF$_3$, —CH$_2$CF$_2$CHF$_2$, —CH$_2$CH$_2$Cl, cyclopentyl, pyrrolidinyl, piperidinyl, morpholinyl or piperazinyl.

In another aspect, the invention provides a pharmaceutical composition comprising the compound disclosed herein and pharmaceutically acceptable excipient, carrier, adjuvant, or any combination thereof.

In some embodiments, the pharmaceutical composition according to the invention, further comprising a drug for treating central nervous system dysfunction, wherein the drug is an antidepressant, an anxiolytic, a lithium salt as an emotional stabilizer, an atypical antipsychotic, an antiepileptic drug, an anti-Parkinson's disease drug, a drug as a selective serotonin reuptake inhibitor and/or a 5-HT$_{1A}$ receptor agonist, a central nervous stimulant, a nicotinic antagonist, or any combination thereof.

In other embodiments, the pharmaceutical composition according to the invention, further comprising a drug for treating central nervous system dysfunction, wherein the drug for treating central nervous system dysfunction of the invention is amitriptyline, desipramine, mirtazapine, bupropion, reboxetine, fluoxetine, trazodone, sertraline, duloxetine, fluvoxamine, milnacipran, levomilnacipran, desvenlafaxine, vilazodone, venlafaxine, dapoxetine, nefazodone, femoxetine, clomipramine, citalopram, escitalopram, paroxetine, lithium carbonate, buspirone, olanzapine, quetiapine, risperidone, ziprasidone, aripiprazole, perospirone, clozapine, modafinil, mecamylamine, cabergoline, adamantane, imipramine, pramipexole, thyroxine, dextromethorphan, quinidine, naltrexone, samidorphan, buprenorphine, melatonin, alprazolam, pipamperone, vestipitant, chlordiazepoxide, perphenazine or any combination thereof.

In another aspect, provided herein is use of the compound or the pharmaceutical composition of the present invention in the manufacture of a medicament for preventing, treating or lessening central nervous system dysfunction.

In some embodiments, the central nervous system dysfunction refers to depression, anxiety, mania, schizophrenia, bipolar disorder, sleep disorder, obsessive-compulsive disorder, panic disorder, post-traumatic stress disorder, dyskinesia, sexual dysfunction, musculoskeletal pain disorder, cognitive impairment, memory impairment, Parkinson's disease, Huntington's disease, phobia, substance abuse or addiction, drug addiction withdrawal symptoms or premenstral syndrome.

In another aspect, provided herein is use of the compound or the pharmaceutical composition of the present invention in the manufacture of a medicament, wherein the medicament is used to inhibit 5-hydroxytryptamine reuptake; and/or the medicament is used to partially activate 5-HT$_{1A}$ receptors.

In another aspect, provided herein is the compound or the pharmaceutical composition of the invention for use in preventing, treating or ameliorating central nervous system dysfunction. In some embodiments, the drug is used to prevent, treat or alleviate central nervous system dysfunction of the mammal, and in other embodiments, the drug is used to prevent, treat or alleviate central nervous system dysfunction of the human.

In some embodiments, the central nervous system dysfunction refers to depression, anxiety, mania, schizophrenia, bipolar disorder, sleep disorder, obsessive-compulsive disorder, panic disorder, post-traumatic stress disorder, dyskinesia, sexual dysfunction, musculoskeletal pain disorder, cognitive impairment, memory impairment, Parkinson's disease, Huntington's disease, phobia, substance abuse or addiction, drug addiction withdrawal symptoms or premenstral syndrome.

In another aspect, provided herein is the compound or the pharmaceutical composition of the invention for use in inhibiting 5-hydroxytryptamine reuptake; and/or partially activating 5-HT$_{1A}$ receptors.

In another aspect, provided herein is a method of preventing, treating or lessening central nervous system dysfunction comprising administering a therapeutically effective amount of the compound or the pharmaceutical composition of the invention to the patient.

In some embodiments, the central nervous system dysfunction refers to depression, anxiety, mania, schizophrenia, bipolar disorder, sleep disorder, obsessive-compulsive disorder, panic disorder, post-traumatic stress disorder, dyskinesia, sexual dysfunction, musculoskeletal pain disorder, cognitive impairment, memory impairment, Parkinson's disease, Huntington's disease, phobia, substance abuse or addiction, drug addiction withdrawal symptoms or premenstral syndrome.

In another aspect, provided herein is a method of inhibiting 5-hydroxytryptamine reuptake; and/or partially activating 5-HT$_{1A}$ receptors comprising administering a therapeutically effective amount of the compound or the pharmaceutical composition of the invention to the patient.

In another aspect, provided herein is use of the compound or the pharmaceutical composition in the preparation of a drug for partially activating 5-HT$_{1A}$ receptors.

In another aspect, provided herein are methods for preparing, separating, and purifying compounds represented by Formula (I), (VI), (VII), (VIII) or (IX).

The results of the biological test indicate that the compound provided herein has strong affinity with human 5-HT transporter (SERT) and strong binding affinity with 5-HT$_{1A}$ receptors; and the compound has good pharmacokinetic properties in rats, dogs or monkeys, and shows some antidepressant activity in forced swimming test and tail suspension test of mice. Therefore, the compound provided herein is used as a preferred selective 5-hydroxytryptamine reuptake inhibitor and/or 5-HT$_{1A}$ receptor agonist.

Any embodiment disclosed herein can be combined with other embodiments as long as they are not contradictory to one another. In addition, any technical feature in one embodiment can be applied to the corresponding technical feature in other embodiments as long as they are not contradictory to one another.

The foregoing merely summarizes certain aspects disclosed herein and is not intended to be limiting in nature. These aspects and other aspects are described more fully below.

DETAILED DESCRIPTION OF THE INVENTION

Definitions and General Terminology

All references referred to herein are incorporated by reference in their entirety. In the event that the meaning expressed in these references is inconsistent with the present invention, the present invention prevails. In addition, the various terms and phrases used herein have the ordinary meanings well known to one skilled in the art to which this invention belongs, and even though the present invention is intended to provide a more detailed description and explanation of the terms and phrases herein. Such terms and phrases are inconsistent with the well-known meaning, the meaning herein prevails. The definitions described herein are applicable no matter whether the terms are discussed individually or in combination.

References will now be made in detail to certain embodiments of the invention, examples of which are illustrated in the accompanying structures and formulas. The invention is intended to cover all alternatives, modifications, and equivalents which may be included within the scope of the present invention. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless defined otherwise, all technical and scientific terms used herein have the same meaning as is commonly understood by one skilled in the art to which this invention belongs. All patents and publications referred to herein are incorporated by reference in their entirety.

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry", Thomas Sorrell, University Science Books, Sausalito: 1999, and "March's Advanced Organic Chemistry", Michael B. Smith and Jerry March, John Wiley & Sons, New York: 2007, the entire contents of which are hereby incorporated by reference.

The grammatical articles "a", "an" and "the", as used herein, are intended to include "at least one" or "one or more" unless otherwise indicated herein or clearly contradicted by the context. Thus, the articles are used herein to refer to one or more than one (i.e. at least one) of the grammatical objects of the article. By way of example, "a component" means one or more components, and thus, possibly, more than one component is contemplated and may be employed or used in an implementation of the described embodiments.

As described herein, compounds disclosed herein may optionally be substituted with one or more substituents, such as the above general compounds, or as exemplified by particular examples, subclasses, and a class of compounds contained in the invention. The term "one or more" means 1, 2, 3, 4, 5 or more depending on the number of sites in which the compound can be substituted with substituents; for example, pyridine is optionally substituted with one or more substituents means that the pyridine is optionally substituted with 1, 2, 3, 4 or 5 substituents.

The term "optional" or "optionally" refers to that a subsequently described event or circumstance may but need not occur, and that the description includes instances where the event or circumstance occurs and instances in which it does not. For example, "optional bond" means that the bond may or may not be present, and that the description includes single, double or triple bonds.

The term "substitution" or "substituted" means that one or more hydrogen atoms in the structure are substituted with specific substituent. Unless otherwise indicated, a substituted group may have a substituent at each substitutable position of the group. When more than one position in a given structure can be substituted with one or more substituents selected from a specified group, the substituent may be either the same or different at each position.

The term "unsubstituted" means that the specified group does not have a substituent.

The term "optionally substituted by . . . " may be used interchangeably with the term "unsubstituted or substituted with . . . ", i.e. the structure is unsubstituted or substituted with one or more substituents of the invention. Substituents herein include, but are not limited to, D, F, Cl, Br, I, azide, nitro, cyano, hydroxy, sulfydryl, amino, —C(=O)amino, —C(=O)O-alkyl, hydroxy-alkylene-, sulfydryl-alkylene-, amino-alkylene-, alkyl, alkenyl, alkynyl, alkoxy, alkoxyalkylene, alkylthio, alkylthioalkylene, alkylamino, alkylaminoalkylene, haloalkyl, haloalkoxy, cycloalkyl, cycloalkylalkylene, carbocyclyl, heterocyclyl, heterocyclealkylene, aryl, arylalkylene, heteroaryl, heteroarylalkylene, and the like.

Furthermore, what need to be explained is that the phrase "each . . . is independently" and "each of . . . and . . . is independently", unless otherwise stated, should be broadly understood. The specific options expressed by the same symbol are independent of each other in different groups; or the specific options expressed by the same symbol are independent of each other in same groups.

The term "unsaturated" refers to a moiety having one or more units of unsaturation.

The term "comprise" is an open expression, it means comprising the contents disclosed herein, but doesn't exclude other contents.

At various places in the present specification, substituents of compounds disclosed herein are disclosed in groups or in ranges. It is specifically intended that the invention include each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "halogen" or "halo" is used interchangeably herein and refers to Fluoro (F), Chloro (Cl), Bromo (Br), or Iodo (I).

The term "alkyl" or "alkyl group" refers to a saturated linear or branched-chain it monovalent hydrocarbon radical of 1-20 carbon atoms. Unless otherwise stated, the alkyl group contains 1-20 carbon atoms. In some embodiments, the alkyl group contains 1-10 carbon atoms. In other embodiments, the alkyl group contains 1-8 carbon atoms. In still other embodiments, the alkyl group contains 1-6 carbon atoms. In still other embodiments, the alkyl group contains 1-4 carbon atoms. In yet other embodiments, the alkyl group contains 1-3 carbon atoms. The aralkyl group is optionally substituted with one or more substituents described herein.

Some non-limiting examples of the alkyl group include, methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_2CH_3$), isobutyl (i-Bu, —$CH_2CH(CH_3)_2$), sec-butyl (s-Bu, —$CH(CH_3)CH_2CH_3$), tert-butyl (t-Bu, —$C(CH_3)_3$), n-pentyl (—$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), n-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, n-heptyl and n-octyl, etc.

The term "alkylene" refers to a saturated divalent hydrocarbon group derived from a saturated straight or branched chain hydrocarbon by the removal of two hydrogen atoms. Unless otherwise stated, the alkyl group contains 1-10 carbon atoms. In some embodiments, the alkenylene group contains 1-6 carbon atoms. In other embodiments, the alkenylene group contains 1-4 carbon atoms. In still other embodiments, the alkenylene group contains 1-2 carbon atoms. Such examples include, but are not limited to methylene (—$CH_2$—), ethylidene (—$CH_2CH_2$—), isopropylene (—$CH(CH_3)CH_2$—), and the like. Wherein the alkylene group is optionally substituted with one or more substitutents described herein.

The term "alkenyl" refers to a linear or branched chain monovalent hydrocarbon radical of 2-12 carbon atoms, with at least one site of unsaturated carbon-carbon, $SP^2$ double bond, and includes radicals having "cis" and "trans" orientations, or alternatively, "E" and "Z" orientations. In some embodiments, the alkenyl contains 2-8 carbon atoms. In other embodiments, the alkenyl contains 2-6 carbon atoms. In still other embodiments, the alkenyl contains 2-4 carbon atoms. Examples of alkenyl groups include, but are not limited to, vinyl (—CH=$CH_2$), allyl (—$CH_2$CH=$CH_2$), and the like. The alkenyl group is optionally substituted with one or more substituents described herein.

The term "alkynyl" refers to a linear or branched chain monovalent hydrocarbon radical of 2-12 carbon atoms, with at least one site of unsaturated carbon-carbon, SP triple bond. In some embodiments, the alkynyl group contains 2-8 carbon atoms. In other embodiments, the alkynyl contains 2-6 carbon atoms. In still other embodiments, the alkynyl contains 2-4 carbon atoms. Examples of the alkynyl group include, but are not limited to, ethynyl (—C≡CH), propargyl (—$CH_2$C≡CH), 1-propynyl (—C≡C—$CH_3$), and the like. The alkynyl group is optionally substituted with one or more substituents described herein.

The term "alkoxy" refers to an alkyl group, as previously defined, attached to the parent molecular moiety via an oxygen atom. Unless otherwise stated, the alkoxy group contains 1-12 carbon atoms. In some embodiments, the alkoxy group contains 1-6 carbon atoms. In other embodiments, the alkoxy group contains 1-4 carbon atoms. In still other embodiments, the alkoxy group contains 1-3 carbon atoms. The alkoxy radicals are optionally substituted with one or more substituents described herein.

Some non-limiting examples of the alkoxy group include, methoxy (MeO, —$OCH_3$), ethoxy (EtO, —$OCH_2CH_3$), 1-propoxy (n-PrO, n-propoxy, —$OCH_2CH_2CH_3$), 2-propoxy (i-PrO, i-propoxy, —$OCH(CH_3)_2$), 1-butoxy (n-BuO, n-butoxy, —$OCH_2CH_2CH_2CH_3$), 2-methyl-1-propoxy (i-BuO, i-butoxy, —$OCH_2CH(CH_3)_2$), 2-butoxy (s-BuO, s-butoxy, —$OCH(CH_3)CH_2CH_3$), 2-methyl-2- propoxy (t-BuO, t-butoxy, —OC(CH$_3$)$_3$), 1-pentoxy (n-pentoxy, —OCH$_2$CH$_2$CH$_2$CH$_2$CH$_3$), 2-pentoxy (—OCH(CH$_3$)CH$_2$CH$_2$CH$_3$), 3-pentoxy (—OCH(CH$_2$CH$_3$)$_2$), 2-methyl-2-butoxy (—OC(CH$_3$)$_2$CH$_2$CH$_3$), 3-methyl-2-butoxy (—OCH(CH$_3$)CH(CH$_3$)$_2$), 3-methyl-1-butoxy (—OCH$_2$CH$_2$CH(CH$_3$)$_2$), 2-methyl-1-butoxy (—OCH$_2$CH(CH$_3$)CH$_2$CH$_3$), and the like.

The term "haloalkyl" or "haloalkoxy" refers to an alkyl or alkoxy group which is substituted with one or more halogen atoms, and wherein each of the alkyl and alkoxy is as defined described herein. Examples of such groups include, but are not limited to, chloromethyl, trifluoromethyl, trifluoroethyl, trifluoromethoxy, and the like. And wherein optionally each of the haloalkyl or haloalkoxy may be substituted with one or more substituents described herein.

The term "alkylamino" or "alkyl amino group" refers to "N-alkyl amino" and "N,N-dialkylamino" wherein amino groups are independently substituted with one or two alkyl radicals. In some embodiments, the alkyl amino is a lower alkyl amino radical having one or two C$_1$-C$_6$ alkyl radicals attached to a nitrogen atom. In other embodiments, the alkyl amino is a lower alkyl amino radical having one or two C$_1$-C$_4$ alkyl radicals attached to a nitrogen atom. Some examples of suitable alkylamino radical include mono or dialkylamino, but are not limited to, N-methylamino, N-ethylamino, N,N-dimethylamino and N,N-diethylamino, and the like. And wherein the alkylamino radical is optionally substituted with one or more substituents described herein.

The term "alkylthio" refers to a group in which a C$_1$-C$_{10}$ straight or branched alkyl group attached to a divalent sulfur atom. In some embodiments, the alkylthiol group is a lower C$_1$-C$_4$ alkylthio group. Such examples include, but are not limited to, methylthio (—SCH$_3$). Wherein the alkylthio radical is optionally substituted with one or more substitutents described herein.

The term "consisting of w atoms" or "w-membered", wherein w is an integer, typically describes the number of atoms in the molecule that make up the ring, and the number of atoms that form a ring in the molecule is w. For example, piperidyl is heterocyclyl consisting of 6 atoms or 6-membered heterocyclyl, and cyclohexyl is cycloalkyl consisting of 6 atoms or 6-membered cycloalkyl.

The term "carbocycle", "carbocyclyl" or "cyclic aliphatics" denotes a monocyclic, bicyclic or tricyclic ring system containing 3-12 carbon atoms with one or more junctions connected to the rest of the molecule. The ring may be fully saturated or contain one or more unsaturations, but none of the aromatic rings may be present. Suitable carbocyclyl groups include, but are not limited to, cycloalkyl, cycloalkenyl and cycloalkynyl. Further examples of the carbocyclyl groups include, but are not limited to, cyclopropyl, cyclobutyl, cyclopentyl, 1-cyclopentyl-1-enyl, l-cyclopentyl-2-enyl, l-cyclopentyl-3-enyl, cyclohexyl, 1-cyclohexyl-1-enyl, l-cyclohexyl-2-enyl, l-cyclohexyl-3-enyl, cyclohexadienyl, cycloheptyl, cyclooctyl, cyclodecyl, and the like. Wherein the carbocyclyl group is optionally substituted with one or more substituents described herein.

The term "cycloalkyl" denotes a monovalent or polyvalent saturated monocyclic, bicyclic or tricyclic system containing 3-12 carbon atoms. Wherein the bicyclic or tricyclic ring system may include fused ring, bridged ring and spiro ring. In some embodiments, the cycloalkyl contains 3-10 carbon atoms. In still other embodiments, the cycloalkyl contains 3-8 carbon atoms. In still other embodiments, the cycloalkyl contains 3-6 carbon atoms. The cycloalkyl radical is optionally substituted with ne or more substituents described herein.

The term "cycloalkyl alkylene" means that a cycloalkyl group is attached to the remainder of the molecule through an alkylene group, wherein the alkylene and cycloalkyl group are as described herein. In some embodiments, a cycloalkyl alkylene group refers to a "lower cycloalkyl alkylene" group, i.e., a cycloalkyl group is attached to a C$_1$-C$_6$ alkylene group. In other embodiments, a cycloalkyl group is attached to a C$_1$-C$_4$ alkylene group. In still other embodiments, a cycloalkyl group is attached to a C$_1$-C$_3$ alkylene group. The cycloalkyl alkylene group is optionally substituted with one or more substituents described herein.

The term "heteroatom" refers to one or more of oxygen (O), sulfur (S), nitrogen (N), phosphorus (P), or silicon (Si), including any oxidized form of nitrogen (N), sulfur (S), or phosphorus (P); forms of primary, secondary, tertiary amines and quaternary ammonium salts; or forms in which hydrogen on nitrogen atoms in heterocycles is substituted, such as N (like N in a 3,4-dihydro-2H-pyrrolyl group), NH (like NH in pyrrolidinyl) or NR (like NR in N-substituted pyrrolidinyl).

The term "heterocycle", "heterocyclyl" or "heterocyclic", as used interchangeably herein refers to a monovalent or multivalent monocyclic, bicyclic or tricyclic system containing 3-14 ring atoms, wherein one or more atoms on the ring are independently substituted with a hetero atom as defined herein, the ring may be fully saturated or contain one or more unsaturations, but none of the aromatic rings may be present. In some embodiments, the "heterocycle", "heterocyclyl" or "heterocyclic" group is a monocycle having 3-8 members (e.g., 2-6 carbon atoms and 1-3 heteroatoms selected from N, O, P and S, wherein the S or P is optionally substituted with one or more oxygen atoms to provide groups like SO, SO$_2$, PO, PO$_2$) or a bicyclo having 7-12 members (e.g., 4-9 carbon atoms and 1-3 heteroatoms selected from N, O, P and S, wherein the S or P is optionally substituted with one or more oxygen atoms to provide groups like SO, SO$_2$, PO, PO$_2$). Wherein the heterocyclic group is optionally substituted with one or more substituents described herein.

The ring atom of the heterocyclyl may be a carbon radical or hetero atom radical. Wherein the —CH$_2$— group can optionally be substituted with a —C(=O)— group. The sulfur atom of the ring may be optionally oxidized to form S-oxides, and the nitrogen atom of the ring may be optionally oxidized to form N-oxides. Examples of heterocyclic group include, but are not limited to oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl, 2-oxa-5-azabicyclo[2.2.1]hept-5-yl, and the like. Some non-limiting examples of heterocyclyl wherein —CH$_2$— group is replaced by —C(=O)— moiety include 2-oxopyrrolidinyl, oxo-1,3-thiazolidinyl, 2-piperidinonyl, 3,5-dioxopiperidinyl, pyrimidinedione-yl, and the like. Some non-limiting examples of the heterocyclyl group of which the sulfur atom is oxidized include sulfolanyl, 1,1-dioxo-thiomorpholinyl, and the like. Wherein the heterocyclic group is optionally substituted with one or more substituents described herein.

The term "heterocyclyl alkylene" means that a heterocyclyl group is attached to the remainder of the molecule through an alkylene group, wherein the alkylene and heterocyclyl groups are as defined herein. In some embodiments, a heterocyclyl alkylene group refers to a "lower heterocyclyl alkylene" group, i.e., a heterocyclyl group is attached to a $C_1$-$C_6$ alkylene group. In other embodiments, a heterocyclyl group is attached to a $C_1$-$C_4$ alkylene group. Such examples include, but are not limited to, pyrrolidin-2-yl methylene-, 2-(pyrrolidin-2-yl) ethylidene-, and the like. And the heterocyclyl alkylene group is optionally substituted with one or more substituents described herein.

The term "aryl" refers to a monovalent or polyvalent monocyclic, bicyclic or tricyclic carbocyclic ring system containing 6 to 14 ring atoms, or 6 to 10 ring atoms, or 6 ring atoms, wherein at least one ring is aromatic. The aryl group is generally, but not necessarily bonded to the parent molecule through an aromatic ring of the aryl group. The term "aryl" and "aromatic ring" can be used interchangeably herein. Examples of the aryl group may include phenyl, naphthyl, anthryl, and the like. The aryl group is optionally substituted with one or more substituents described herein.

The term "aryl alkylene" denotes that an aryl group is attached to the remainder of the molecule through an alkylene, wherein the alkylene and aryl groups are as defined herein, and in some embodiments, an aryl alkylene group refers to a "lower arylalkylene" group, i.e., an aryl group attached to a $C_1$-$C_6$ alkylene group. In other embodiments, an arylalkylene group refers to a "phenylene group" containing a $C_1$-$C_4$ alkylene group. Specific examples include benzyl, 2-phenylethylene-, and the like. And the aryl alkylene group is optionally substituted with one or more substituents described herein.

The term "heteroaryl" or "heteroaromatic ring" refers to a monovalent or multivalent monocyclic, bicyclic, or tricyclic system having 5 to 14 ring atoms, or 5 to 10 ring atoms, or 5 to 6 ring atoms, wherein at least one ring in the system is aromatic and at least one ring comprises one or more heteroatoms. The heteroaryl group is generally, but not necessarily bonded to the parent molecule through an aromatic ring of the heteroaryl group. The term "hetreroaryl" and "heteroaromatic ring" or "heteroaromatic compound" can be used interchangeably herein. The heteroaryl group is optionally substituted with one or more substituents disclosed herein. In some embodiments, 5-10 membered heteroaryl comprises 1, 2, 3 or 4 heteroatoms independently selected from O, S and N; in other embodiments, 5-6 membered heteroaryl is a monocyclic system and contains 1, 2, 3 or 4 heteroatoms independently selected from O, S and N.

Some non-limiting examples of heteroaryl group include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the like; and also include, but are not limited to the following bicyclo: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl or 4-isoquinolinyl), imidazo[1,2-a]pyridyl, pyrazolo[1,5-a]pyridyl, pyrazolo[1,5-a]pyrimidyl, imidazo[1,2-b]pyridazinyl, triazolo[4,3-b]pyridazinyl, [1,2,4]triazolo[1,5-a]pyrimidinyl, or [1,2,4]triazolo[1,5-a]pyridyl, and the like.

The term "heteroaryl alkylene" denotes a heteroaryl group attached to the remainder of the molecule through an alkylene group, wherein the alkylene and heteroaryl group are as described herein, in some embodiments, a heteroarylalkylene group refers to a "lower heteroarylalkylene" group, i.e., a heteroaryl group is attached to a $C_1$-$C_6$ alkylene group. In other embodiments, a heteroaryl group is attached to a $C_1$-$C_4$ alkylene group. Specific examples include pyridin-2-yl methylene-, 2-(furan-3-yl)ethylene-, and the like. The heteroarylalkylene group is optionally substituted with one or more substituents described herein.

The term "carbonyl", denotes —C(=O)—, may be used alone or in conjunction with other terms; the term "acyl" means —C(=O)—R; the term "amido" means —NH—C(=O)—R; the term "carbamoyl" means —C(=O)NH$_2$.

As described herein, a ring system formed by substituent R connect to a double ring central through a bond (as shown in formula a) represents that substituent R may replace hydrogen at any reasonable or substitutable position on the ring it attached to (such as ring B of formula a). For example, Formula a represents that any substitutable position on ring B may be substituted with R, as shown in Formulae a$^{1-3}$.

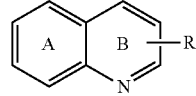

Formula a

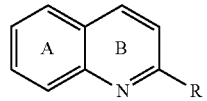

Formula a$^1$

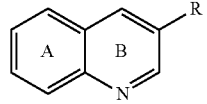

Formula a$^2$

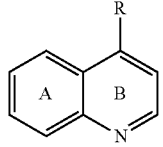

Formula a$^3$

As described herein, a ring system formed by $(R^e)_f$ which are connected to a ring central through a bond represents that f substituent $R^e$ may replace hydrogen at any reasonable or substitutable position on the ring. For example, Formula b represents that ring G may be substituted with f $R^e$, and when f is greater than 1, each $R^e$ may be independently selected from the same or different substituents.

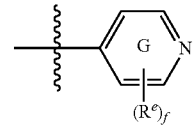

Formula b

As used herein, the term "subject" refers to animal. Typically the animal is mammal, including human. Subject, for example, also refers to primates (e.g., humans, males or females), cows, sheep, goats, horses, dogs, cats, rabbits, rats, mice, fish, birds, and the like. In some embodiments, the subject is a primate. In yet other embodiments, the subject is a human.

As used herein, the term "patient" refers to human (including adults and children) or other animal. In some embodiments, "patient" refers to human.

The term "stereoisomers" refers to compounds which have identical chemical constitution, but differ with regard to the arrangement of the atoms or groups in space. Stereoisomers include enantiomers, diastereomers, conformers (rotamers), geometric (cis/trans) isomers, atropisomers, and the like.

The term "chiral molecule" refers to molecules which have the property of non-superimposability with their mirror image partner, while the term "achiral molecule" refers to molecules which are superimposable with their mirror image partner.

The term "racemates" or "racemic mixtures" refers to an equimolar mixture of two enantiomers which lacks optical activity.

The term "enantiomers" refers to two isomers of a compound which are non-superimposable but mirror images of one another.

The term "diastereomers" refers to a stereoisomer with two or more chiral centers and whose molecules are not mirror images of one another. Diastereomers have different physical properties, e.g. melting points, boiling points, spectral properties or reactivity. Mixture of diastereomers may be separated under high resolution analytical procedures such as electrophoresis and chromatography such as HPLC.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. A specific stereoisomer may be referred to as an enantiomer, and a mixture of such stereoisomers is called an enantiomeric mixture. A 50:50 mixture of enantiomers is referred to as a racemic mixture or a racemate, which may occur where there has been no stereo selection or stereo specificity in a chemical reaction or process.

Any asymmetric atom (e.g., carbon or the like) of the compound(s) disclosed herein can be present in racemic or enantiomerically enriched, for example the (R)-, (S)- or (R,S)-configuration. In some embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

Any resulting mixtures of stereoisomers can be separated on the basis of the physicochemical differences of the constituents, into the pure or substantially pure geometric isomers, enantiomers, diastereomers, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Particularly enantiomers can also be prepared by asymmetric syntheses. See, for example, Jacques, et al., Enantiomers, Racemates and Resolutions (Wiley Interscience, New York, 1981); Principles of Asymmetric Synthesis (2nd Ed. Robert E. Gawley, Jeffrey Aube, Elsevier, Oxford, U K, 2012); Eliel, E. L. Stereochemistry of Carbon Compounds (McGraw-Hill, N Y, 1962); Wilen, S. H. Tables of Resolving Agents and Optical Resolutions p. 268 (E. L. Eliel, Ed., Univ. of Notre Dame Press, Notre Dame, Ind. 1972); Chiral Separation Techniques: A Practical Approach (Subramanian, G. Ed., Wiley-VCH Verlag GmbH & Co. KGaA, Weinheim, Germany, 2007).

The term "tautomer" or "tautomeric form" refers to structural isomers of different energies which are interconvertible via a low energy barrier. In the event that tautomerization is possible (e.g. in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2, 4-dione and 4-hydroxypent-3-en-2-one tautomers. Another example of tautomerization is phenol-keto tautomerization. The specific example of phenol-keto tautomerisms is pyridin-4-ol and pyridin-4 (1H)-one tautomerism. Unless otherwise stated, all tautomeric forms of the compounds disclosed herein are within the scope of the invention.

Unless otherwise stated, structures depicted herein are also meant to include all isomeric (e.g., enantiomeric, diastereomeric, and geometric) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric mixtures of the present compounds are within the scope disclosed herein.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

The term "pharmaceutically acceptable" as used herein, refers to those compounds, materials, compositions, and/or dosage forms which are, within the scope of sound medical judgment, suitable for use in contacting with the tissues of patients without excessive toxicity, irritation, allergic response, or other problem or complication commensurate with a reasonable benefit/risk ratio, and are effective for their intended use.

The term "prodrug" refers to a compound that is transformed in vivo into a compound of Formula (I) to Formula (IX). Such a transformation can be affected, for example, by hydrolysis of the prodrug form in blood or enzymatic transformation to the parent form in blood or tissue. Prodrugs of the compounds disclosed herein may be, for example, esters. Esters that may be utilized as prodrugs in the present invention are phenyl esters, aliphatic ($C_1$-$C_{24}$) esters, acyloxymethyl esters, carbonates, carbamates, and amino acid esters. For example, a compound disclosed herein that contains hydroxy may be acylated at this position in its prodrug form. Other prodrug forms include phosphates, such as, those phosphate compounds derived from the phosphonation of a hydroxy group on the parent compound. A thorough discussion of prodrugs is provided in the following literature: Higuchi et al., Pro-drugs as Novel Delivery Systems, Vol. 14 of the A.C.S. Symposium Series, Roche et al., ed., Bioreversible Carriers in Drug Design, American Pharmaceutical Association and Pergamon Press, 1987; Rautio et al., Prodrugs: Design and Clinical Applications, Nature Reviews Drug Discovery, 2008, 7, 255-270, and Hecker et al., Prodrugs of Phosphates and Phosphonates, Journal of Medicinal Chemistry, 2008, 51, 2328-2345, each of which is incorporated herein by reference.

The term "protecting group" or "PG" refers to a substituent that is commonly employed to block or protect a particular functionality while reacting with other functional groups on the compound. For example, an "amino-protecting group" is a substituent attached to an amino group that blocks or protects the amino functionality in the compound. Suitable amino-protecting groups include acetyl, trifluoroacetyl, t-butoxy-carbonyl (BOC, Boc), benzyloxy-carbonyl (CBZ, Cbz) and 9-fluorenylmethylenoxy-carbonyl (Fmoc). Similarly, a "hydroxy-protecting group" refers to a substituent of hydroxy that blocks or protects the hydroxy functionality. Some non-limiting examples of suitable hydroxy-protecting groups include trialkylsilyl, acetyl, benzoyl, and benzyl. A "carboxy-protecting group" refers to a substituent of carboxy that blocks or protects the carboxy functionality. Common carboxy-protecting groups include —$CH_2CH_2SO_2Ph$, cyanoethyl, 2-(trimethylsilyl)ethyl, 2-(trimethylsilyl)ethoxy-methyl, 2-(p-toluenesulfonyl)ethyl, 2-(p-nitrophenylsulfonyl)-ethyl, 2-(diphenylphosphino)-ethyl, nitroethyl and the like. For a general description of protecting groups and their use, see Greene et al., Protective Groups in Organic Synthesis, John Wiley & Sons, New York, 1991 and Kocienski et al., Protecting Groups, Thieme, Stuttgart, 2005.

The term "pharmaceutically acceptable salts" refers to organic or inorganic salts of a compound disclosed herein. Pharmaceutically acceptable salts are well known in the art. For example, S. M. Berge et al., describe pharmaceutically acceptable salts in detail in J. Pharmaceutical Sciences, 1977, 66: 1-19, which is incorporated herein by reference. Pharmaceutically acceptable salts formed by non-toxic acids include, but are not limited to salts of inorganic acids such as hydrochloric acid, hydrobromic acid, phosphoric acid, sulfuric acid, nitric acid and perchloric acid or with salts of organic acids such as acetic acid, oxalic acid, maleic acid, fumaric acid, tartaric acid, citric acid, succinic acid and malonic acid or by using other methods described in the literature such as ion exchange. Other pharmaceutically acceptable salts include, but are not limited to, adipate, benzene sulfonate, benzoate, butyrate, camphorate, camphorsulfonate, ethanesulfonate, formate, fumarate, gluconate, heptanoate, hexanoate, malate, methanesulfonate, 2-naphthalenesulfonate, propionate, p-toluenesulfonate, and the like. Pharmaceutically acceptable salts formed by suitable bases include, but are not limited to, salts of inorganic base including alkali metal, alkaline earth metal salts and ammonium salts. The alkali metal salts or alkaline earth metal salts include sodium salts, lithium salts, potassium salts, calcium salts, magnesium salts, and the like. And organic base salts include primary, secondary, tertiary, and $N^+(C_{1-4}alkyl)_4$ salts, substituted amines salt (including naturally occurring substituted amines, cyclic amines, basic ion exchange resins), and the like. Certain organic amine salts include, such as isopropylamine salts, benzathine salts, cholinates, diethanolamine salts, diethylamine salts, lysine salts, meglumine salts, piperazine salts and tromethamine salts. This invention also envisions the quaternization of any basic nitrogen-containing groups of the compounds disclosed herein. Water or oil soluble or dispersable products may be obtained by such quaternization. Further pharmaceutically acceptable salts include appropriate, nontoxic ammonium, quaternary ammonium, and amine cations formed by using counterions such as halide, hydroxide, carboxylate, sulfate, phosphate, nitrate, $C_1$-$C_8$ sulfonate or aryl sulfonate.

The term "solvate" refers to an association or complex of one or more solvent molecules and a compound disclosed herein. Some non-limiting examples of the solvent that form solvates include water, isopropanol, ethanol, methanol, dimethylsulfoxide (DMSO), ethyl acetate, acetic acid and ethanolamine or mixtures thereof.

The term "hydrate" can be used when said solvent is water. In some embodiments, one molecule of the compounds disclosed herein is associated with a water molecule, such as a hydrate. In other embodiments, one molecule of the compounds disclosed herein may be associated with more than one water molecules, such as a dihydrate. In still other embodiments, one molecule of the compounds disclosed herein may be associated with less than one solvent molecule, such as a hemihydrate. Furthermore, all the hydrates of the invention retain the biological effectiveness of the non-hydrate form of the compounds disclosed herein.

The term "preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

The term "therapeutically effective amount" means that when administered to a subject to treat a disease, the amount of the compound is sufficient to effect treatment of the disease. The "therapeutically effective amount" can vary with the compound, the disease and severity, and the condition, age, weight, sex, etc. of the subject to be treated.

"Treatment" of a disease state includes: (i) preventing a disease state, i.e., clinical symptoms of a disease state of a subject who may be exposed to or susceptible to a disease state but have not experienced or showed symptoms of the disease state are no longer developed; (ii) inhibiting the disease state, i.e., preventing the progression of the disease state or its clinical symptoms, or (iii) relieving the disease state, i.e., temporarily or permanently resolving the disease state or its clinical symptoms.

DESCRIPTION OF COMPOUNDS OF THE INVENTION

The present invention relates to a substituted pyrimidine piperazine compound, a pharmaceutically acceptable salt thereof, a pharmaceutical formulation and a composition thereof, which can be used as a selective 5-hydroxytryptamine reuptake inhibitor and/or a 5-HT$_{1A}$ receptor agonist, and have potential use in the treatment of central nervous system dysfunction, such as depression, anxiety, bipolar disorder.

In one aspect, the present invention provides a compound having Formula (I) or a stereoisomer, a geometric isomer, a tautomer, an N-oxide, a hydrate, a solvate, a metabolite, a pharmaceutically acceptable salt or a prodrug thereof,

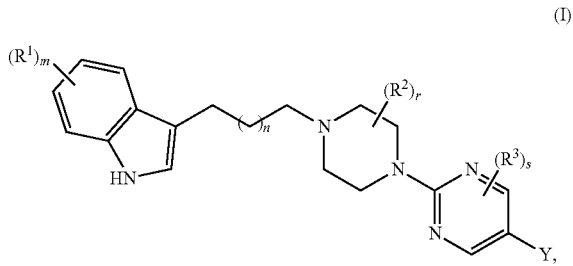

(I)

wherein each $R^1$, $R^2$, $R^3$, Y, m, n, r and s is as defined herein.

In some embodiments, Y is cycloalkyl, heterocyclyl or heteroaryl, wherein optionally each cycloalkyl, heterocyclyl, and heteroaryl is independently substituted with one or more $R^x$; and each $R^x$ is as defined herein.

In some embodiments, each $R^x$ is independently H, D, F, Cl, Br, I, nitro, cyano, —NR$^a$R$^b$, —OR$^c$, —SR$^c$, —C(=O)R$^d$, —C(=O)OR$^c$, —C(=O)NR$^a$R$^b$, —OC(=O)R$^d$, —N(R$^a$)C(=O)R$^d$, —S(=O)R$^d$, —S(=O)$_2$R$^d$, —S(=O)$_2$OR$^c$, —S(=O)$_2$NR$^a$R$^b$, —N(R$^a$)S(=O)$_2$R$^d$, —N(R$^a$)C(=O)OR$^c$, —N(R$^a$)C(=O)NR$^a$R$^b$, alkyl, alkenyl, alkynyl, haloalkyl, cycloalkyl, cycloalkylalkylene, heterocyclyl, heterocyclylalkylene, aryl, arylalkylene, hetaryl or heterarylalkylene, wherein optionally the —NR$^a$R$^b$, —OR$^c$, —SR$^c$, —C(=O)R$^d$, —C(=O)OR$^c$, —C(=O)NR$^a$R$^b$, —OC(=O)R$^d$, —N(R$^a$)C(=O)R$^d$, —S(=O)R$^d$, —S(=O)$_2$R$^d$, —S(=O)$_2$OR$^c$, —S(=O)$_2$NR$^a$R$^b$, —N(R$^a$)S(=O)$_2$R$^d$, —N(R$^a$)C(=O)OR$^c$, —N(R$^a$)C(=O)NR$^a$R$^b$, alkyl, alkenyl, alkynyl, haloalkyl, cycloalkyl, cycloalkylalkylene, heterocyclyl, heterocyclylalkylene, aryl, arylalkylene, heteroaryl and heteroarylalkylene is independently substituted with one or more $R^4$; and each $R^a$, $R^b$, $R^c$, $R^d$ and $R^4$ is as defined herein.

In some embodiments, each $R^4$ is independently F, Cl, Br, I, nitro, cyano, azido, amino, hydroxy, sulfydryl, $C_1$-$C_4$ alkyl, $C_2$-$C_6$ alkenyl, $C_2$-$C_6$ alkynyl, $C_1$-$C_4$ haloalkyl, $C_1$-$C_4$ alkoxy, $C_1$-$C_4$ haloalkoxy, $C_1$-$C_4$ alkylamino, $C_1$-$C_4$ alkylthio, amino-($C_1$-$C_4$ alkylene)-, hydroxy-($C_1$-$C_4$ alkylene)-, sulfydryl-($C_1$-$C_4$ alkylene)-, ($C_1$-$C_4$ alkylamino)-($C_1$-$C_4$ alkylene)-, ($C_1$-$C_4$ alkoxy)-($C_1$-$C_4$ alkylene)-, ($C_1$-$C_4$ alkylthio)-($C_1$-$C_4$ alkylene)-, $C_3$-$C_6$ cycloalkyl, ($C_3$-$C_6$ cycloalkyl)-($C_1$-$C_4$ alkylene)-, 3-7 membered heterocyclyl, (3-7 membered heterocyclyl)-($C_1$-$C_4$ alkylene)-, phenyl, phenyl-($C_1$-$C_4$ alkylene)-, 5-6 membered heteroaryl or (5-6 membered heteroaryl)-($C_1$-$C_4$ alkylene)-;

In some embodiments, each $R^1$ is independently H, D, F, Cl, Br, I, nitro, cyano, amino, hydroxy, sulfydryl, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, ($C_1$-$C_6$ alkoxy)-($C_1$-$C_4$ alkylene)-, $C_1$-$C_6$ alkylamino, ($C_1$-$C_6$ alkylamino)-($C_1$-$C_4$ alkylene)-, $C_1$-$C_6$ alkylthio or ($C_1$-$C_6$ alkylthio)-($C_1$-$C_4$ alkylene)-.

In some embodiments, each $R^2$ is independently H, D, F, Cl, Br, I, $C_1$-$C_6$ alkyl, $C_1$-$C_6$ haloalkyl, —NR$^a$R$^b$, —OR$^c$, —C(=O)R$^d$, —C(=O)OR$^c$, —C(=O)NR$^a$R$^b$ or ($C_6$-$C_{10}$ aryl)-($C_1$-$C_6$ alkylene)-, or two $R^2$ of adjacent carbon atoms, together with the carbon atoms they are attached to, form a $C_3$-$C_6$ carbocycle, a benzene ring, a 3-7 membered heterocyclyl ring or a 5-6 membered heteroaryl ring; or two $R^2$ of the same carbon atom, together with the carbon atom they are attached to, form a $C_3$-$C_6$ carbocycle, a 3-7 membered heterocyclyl ring; and wherein each $R^a$, $R^b$, $R^c$ and $R^d$ is as defined herein.

In some embodiments, each $R^3$ is independently H, D, F, Cl, Br, I, nitro, cyano, amino, hydroxy, sulfydryl, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, ($C_1$-$C_6$ alkoxy)-($C_1$-$C_4$ alkylene)-, $C_1$-$C_6$ alkylamino, ($C_1$-$C_6$ alkylamino)-($C_1$-$C_4$ alkylene)-, $C_1$-$C_6$ alkylthio or ($C_1$-$C_6$ alkylthio)-($C_1$-$C_4$ alkylene)-.

In some embodiments, each $R^a$ and $R^b$ is independently H, $C_1$-$C_6$ alkyl, $C_3$-$C_6$ alkenyl, $C_3$-$C_6$ alkynyl, $C_1$-$C_6$ haloalkyl, $C_3$-$C_6$ cycloalkyl, ($C_3$-$C_6$ cycloalkyl)-($C_1$-$C_4$ alkylene)-, 3-7 membered heterocyclyl, (3-7 membered heterocyclyl)-($C_1$-$C_4$ alkylene)-, phenyl, phenyl-($C_1$-$C_4$ alkylene)-, 5-6 membered heteroaryl and (5-6 membered heteroaryl)-($C_1$-$C_4$ alkylene)-, or $R^a$ and $R^b$ together with the nitrogen atom they are attached to, form a 3-7 membered heterocyclyl ring; and each $R^c$ and $R^d$ is independently H, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, ($C_3$-$C_6$ cycloalkyl)-($C_1$-$C_4$ alkylene)-, 3-7 membered heterocyclyl, (3-7 membered heterocyclyl)-($C_1$-$C_4$ alkylene)-, phenyl, phenyl-($C_1$-$C_4$ alkylene)-, 5-6 membered heteroaryl and (5-6 membered heteroaryl)-($C_1$-$C_4$ alkylene)-.

In some embodiments, each m is independently 0, 1, 2, 3 or 4.

In some embodiments, each n is independently 0, 1, 2, 3 or 4.

In some embodiments, each r is independently 0, 1, 2, 3, 4, 5 or 6.

In some embodiments, each s is independently 0, 1, or 2.

In some embodiments, Y is $C_3$-$C_{10}$ cycloalkyl, 3-10 membered heterocyclyl or 5-10 membered heteroaryl, wherein optionally each of the $C_3$-$C_{10}$ cycloalkyl, 3-10 membered heterocyclyl, and 5-10 membered heteroaryl is independently substituted with one or more $R^x$; and each $R^x$ is as defined herein.

In other embodiments, Y is $C_3$-$C_6$ cycloalkyl, 3-6 membered heterocyclyl or 5-6 membered heteroaryl, wherein optionally each of the $C_3$-$C_6$ cycloalkyl, 3-6 membered heterocyclyl, and 5-6 membered heteroaryl is independently substituted with one or more $R^x$;

each $R^x$ is as defined herein.

In other embodiments, Y is one of the substructures of Formulae (Y-1) to (Y-15):

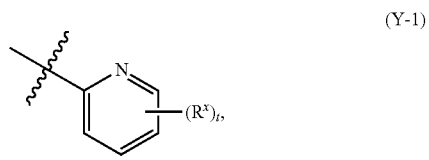

(Y-1)

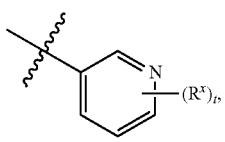 (Y-2)

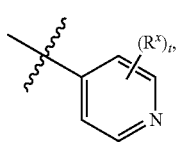 (Y-3)

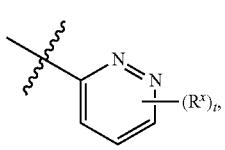 (Y-4)

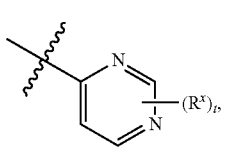 (Y-5)

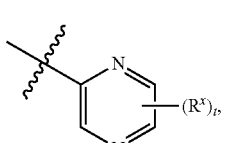 (Y-6)

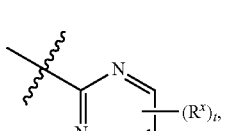 (Y-7)

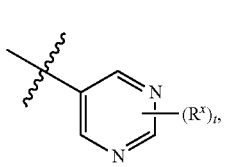 (Y-8)

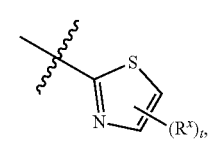 (Y-9)

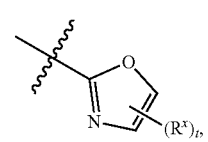 (Y-10)

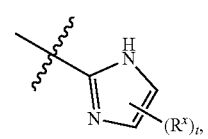 (Y-11)

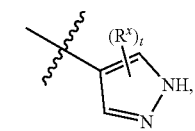 (Y-12)

(Y-13)

(Y-14) or (Y-15)

wherein each t is independently 1, 2, 3 or 4; and
each $R^x$ is as defined herein.

In some embodiments, the present invention provides a compound having Formula (II) or a stereoisomer, a geometric isomer, a tautomer, an N-oxide, a hydrate, a solvate, a metabolite, a pharmaceutically acceptable salt or a prodrug thereof,

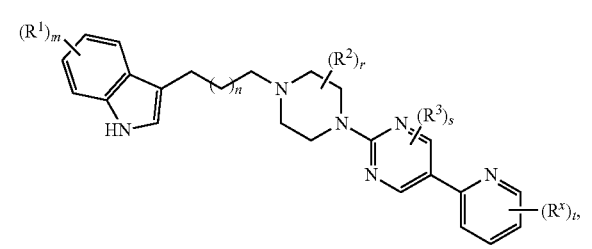

(II)

wherein each t is independently 1, 2, 3 or 4; and
wherein each $R^1$, $R^2$, $R^3$, $R^x$, m, n, r and s is as defined herein.

In some embodiments, the present invention provides a compound having Formula (III) or a stereoisomer, a geometric isomer, a tautomer, an N-oxide, a hydrate, a solvate, a metabolite, a pharmaceutically acceptable salt or a prodrug thereof,

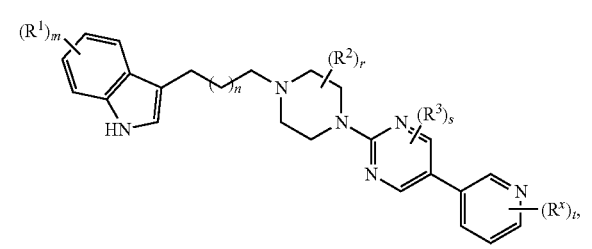

(III)

wherein each t is independently 1, 2, 3 or 4; and
wherein each $R^1$, $R^2$, $R^3$, $R^x$, m, n, r and s is as defined herein.

In some embodiments, the present invention provides a compound having Formula (IV) or a stereoisomer, a geometric isomer, a tautomer, an N-oxide, a hydrate, a solvate, a metabolite, a pharmaceutically acceptable salt or a prodrug thereof,

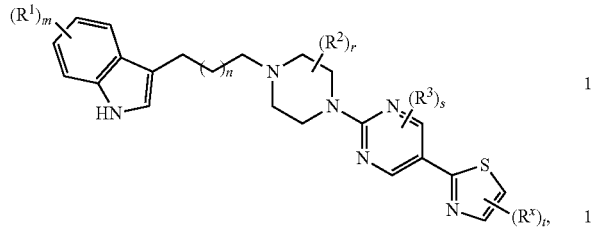

(IV)

wherein each t is independently 1, 2, 3 or 4; and wherein each $R^1$, $R^2$, $R^3$, $R^x$, m, n, r and s is as defined herein.

In some embodiments, the present invention provides a compound having Formula (V) or a stereoisomer, a geometric isomer, a tautomer, an N-oxide, a hydrate, a solvate, a metabolite, a pharmaceutically acceptable salt or a prodrug thereof,

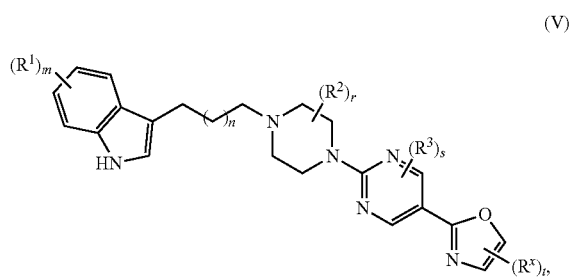

(V)

wherein each t is independently 1, 2, 3 or 4; and wherein each $R^1$, $R^2$, $R^3$, $R^x$, m, n, r and s is as defined herein.

In other embodiments, the present invention provides a compound having Formula (VI) or a stereoisomer, a geometric isomer, a tautomer, an N-oxide, a hydrate, a solvate, a metabolite, a pharmaceutically acceptable salt or a prodrug thereof,

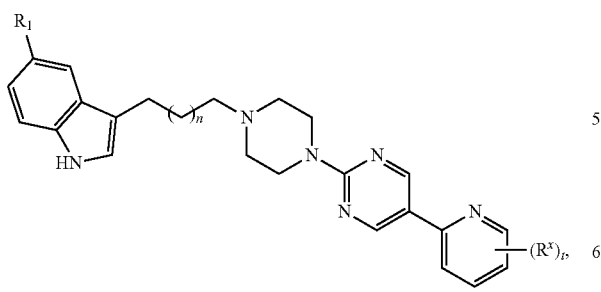

(VI)

wherein each t is independently 1, 2, 3 or 4; and each $R^1$, $R^x$ and n is as defined herein.

In other embodiments, the present invention provides a compound having Formula (VII) or a stereoisomer, a geometric isomer, a tautomer, an N-oxide, a hydrate, a solvate, a metabolite, a pharmaceutically acceptable salt or a prodrug thereof,

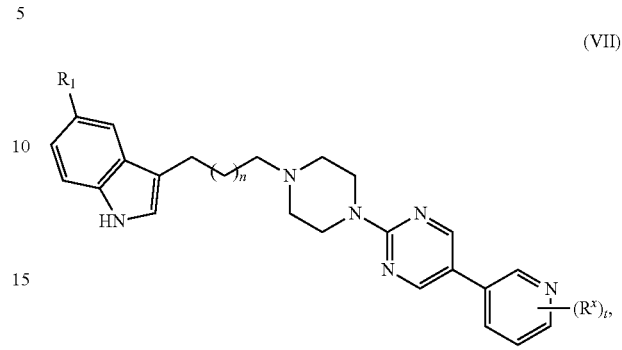

(VII)

wherein each t is independently 1, 2, 3 or 4; and each $R^1$, $R^x$ and n is as defined herein.

In other embodiments, the present invention provides a compound having Formula (VIII) or a stereoisomer, a geometric isomer, a tautomer, an N-oxide, a hydrate, a solvate, a metabolite, a pharmaceutically acceptable salt or a prodrug thereof,

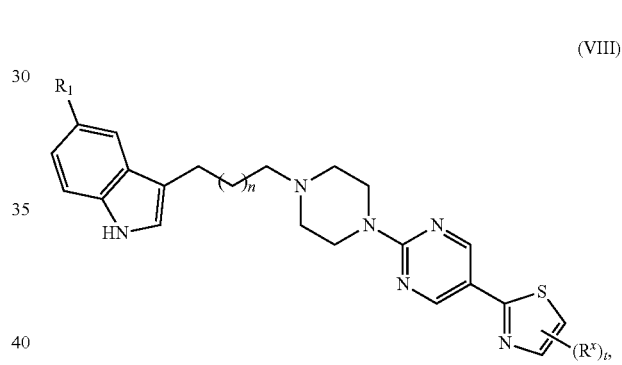

(VIII)

wherein each t is independently 1, 2, 3 or 4; and each $R^1$, $R^x$ and n is as defined herein.

In other embodiments, the present invention provides a compound having Formula (IX) or a stereoisomer, a geometric isomer, a tautomer, an N-oxide, a hydrate, a solvate, a metabolite, a pharmaceutically acceptable salt or a prodrug thereof,

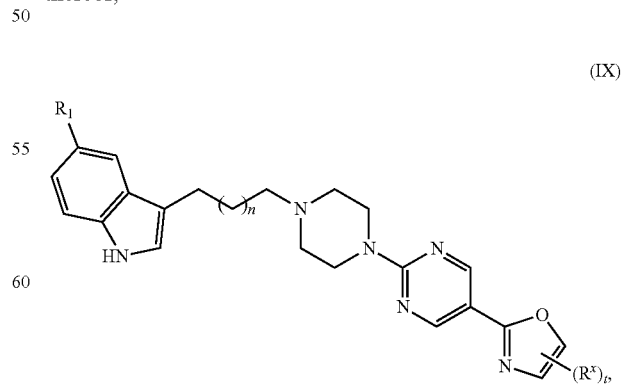

(IX)

wherein each t is independently 1, 2, 3 or 4; and each $R^1$, $R^x$ and n is as defined herein.

In some embodiments, each $R^1$ is independently H, D, F, Cl, Br, I, nitro, cyano, amino, hydroxy, sulfydryl, $C_1$-$C_4$ alkyl, $C_2$-$C_4$ alkenyl, $C_2$-$C_4$ alkynyl, $C_1$-$C_4$ haloalkyl, $C_1$-$C_4$ alkoxy, $C_1$-$C_4$ haloalkoxy, ($C_1$-$C_4$ alkoxy)-($C_1$-$C_4$ alkylene)-, $C_1$-$C_4$ alkylamino, ($C_1$-$C_4$ alkylamino)-($C_1$-$C_4$ alkylene)-, $C_1$-$C_4$ alkylthio or ($C_1$-$C_4$ alkylthio)-($C_1$-$C_4$ alkylene)-.

In some embodiments, each $R^1$ is independently H, D, F, Cl, Br, I, cyano, nitro, amino, —NMe$_2$, hydroxy, —OMe, —OEt, —O(i-Pr), —O(t-Bu), methyl, ethyl, -(n-Pr), -(i-Pr), -(t-Bu) or —CF$_3$.

In some embodiments, each $R^2$ is independently H, D, F, Cl, Br, I, amino, hydroxy, methyl, ethyl, -(n-Pr), -(i-Pr), -(t-Bu) or —CF$_3$, —OMe, —OEt, —O(i-Pr) or —O(t-Bu).

In some embodiments, each $R^3$ is independently H, D, F, Cl, Br, I, cyano, nitro, amino, —NMe$_2$, hydroxy, —OMe, —OEt, —O(i-Pr), —O(t-Bu), methyl, ethyl, -(n-Pr), -(i-Pr), -(t-Bu) or —CF$_3$.

In some embodiments, each $R^x$ is independently H, D, F, Cl, Br, I, nitro, cyano, —NR$^a$R$^b$, —OR$^c$, —SR$^c$, —C(=O)R$^d$, —C(=O)OR$^c$, —C(=O)NR$^a$R$^b$, —OC(=O)R$^d$, —N(R$^a$)C(=O)R$^d$, —S(=O)R$^d$, —S(=O)$_2$R$^d$, —S(=O)$_2$OR$^c$, —S(=O)$_2$NR$^a$R$^b$, —N(R$^a$)S(=O)$_2$R$^d$, —N(R$^a$)C(=O)OR$^c$, —N(R$^a$)C(=O)NR$^a$R$^b$, $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, ($C_3$-$C_{10}$ cycloalkyl)-($C_1$-$C_6$ alkylene)-, 3-10 membered heterocyclyl, (3-10 membered heterocyclyl)-($C_1$-$C_6$ alkylene)-, $C_6$-$C_{10}$ aryl, ($C_6$-$C_{10}$ aryl)-($C_1$-$C_6$ alkylene)-, 5-10 membered heteroaryl or (5-10 membered heteroaryl)-($C_1$-$C_6$ alkylene)-, wherein optionally each of the —NR$^a$R$^b$, —OR$^c$, —SR$^c$, —C(=O)R$^d$, —C(=O)OR$^c$, —C(=O)NR$^a$R$^b$, —OC(=O)R$^d$, —N(R$^a$)C(=O)R$^d$, —S(=O)R$^d$, —S(=O)$_2$R$^d$, —S(=O)$_2$OR$^c$, —S(=O)$_2$NR$^a$R$^b$, —N(R$^a$)S(=O)$_2$R$^d$, —N(R$^a$)C(=O)OR$^c$, —N(R$^a$)C(=O)NR$^a$R$^b$, $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, ($C_3$-$C_{10}$ cycloalkyl)-($C_1$-$C_6$ alkylene)-, 3-10 membered heterocyclyl, (3-10 membered heterocyclyl)-($C_1$-$C_6$ alkylene)-, $C_6$-$C_{10}$ aryl, ($C_6$-$C_{10}$ aryl)-($C_1$-$C_6$ alkylene)-, 5-10 membered heteroaryl or (5-10 membered heteroaryl)-($C_1$-$C_6$ alkylene)- is independently substituted with one or more $R^4$; and each $R^a$, $R^b$, $R^c$, $R^d$ and $R^4$ is as defined herein.

In some embodiments, each $R^x$ is independently H, D, F, Cl, Br, I, nitro, cyano, —NR$^a$R$^b$, —OR$^c$, —SR$^c$, —C(=O)R$^d$, —C(=O)OR$^c$, —C(=O)NR$^a$R$^b$, —OC(=O)R$^d$, —N(R$^a$)C(=O)R$^d$, —S(=O)R$^d$, —S(=O)$_2$R$^d$, —S(=O)$_2$OR$^c$, —S(=O)$_2$NR$^a$R$^b$, —N(R$^a$)S(=O)$_2$R$^d$, —N(R$^a$)C(=O)OR$^c$, —N(R$^a$)C(=O)NR$^a$R$^b$, $C_1$-$C_4$ alkyl, $C_2$-$C_4$ alkenyl, $C_2$-$C_4$ alkynyl, $C_1$-$C_4$ haloalkyl, $C_3$-$C_6$ cycloalkyl, ($C_3$-$C_6$ cycloalkyl)-($C_1$-$C_4$ alkylene)-, 3-7 membered heterocyclyl, (3-7 membered heterocyclyl)-($C_1$-$C_4$ alkylene)-, phenyl, phenyl-($C_1$-$C_4$ alkylene)-, 5-6 membered heteroaryl or (5-6 membered heteroaryl)-($C_1$-$C_4$ alkylene)-, wherein optionally each of the —NR$^a$R$^b$, —OR$^c$, —SR$^c$, —C(=O)R$^d$, —C(=O)OR$^c$, —C(=O)NR$^a$R$^b$, —OC(=O)R$^d$, —N(R$^a$)C(=O)R$^d$, —S(=O)R$^d$, —S(=O)$_2$R$^d$, —S(=O)$_2$OR$^c$, —S(=O)$_2$NR$^a$R$^b$, —N(R$^a$)S(=O)$_2$R$^d$, —N(R$^a$)C(=O)OR$^c$, —N(R$^a$)C(=O)NR$^a$R$^b$, $C_1$-$C_4$ alkyl, $C_2$-$C_4$ alkenyl, $C_2$-$C_4$ alkynyl, $C_1$-$C_4$ haloalkyl, $C_3$-$C_6$ cycloalkyl, ($C_3$-$C_6$ cycloalkyl)-($C_1$-$C_4$ alkylene)-, 3-7 membered heterocyclyl, (3-7 membered heterocyclyl)-($C_1$-$C_4$ alkylene)-, phenyl, phenyl-($C_1$-$C_4$ alkylene)-, 5-6 membered heteroaryl or (5-6 membered heteroaryl)-($C_1$-$C_4$ alkylene)- is independently substituted with one or more $R^4$; and each $R^a$, $R^b$, $R^c$, $R^d$ and $R^4$ is as defined herein.

In other embodiments, each $R^x$ is independently H, D, F, Cl, Br, I, cyano, nitro, amino, —NMe$_2$, —NHEt, —NEt$_2$, hydroxy, —OMe, —OEt, —O(n-Pr), —O(i-Pr), —O(t-Bu), methyl, ethyl, -(n-Pr), -(i-Pr), -(t-Bu), —CF$_3$, —CH$_2$CH$_2$Cl, —OCHF$_2$, —OCF$_3$, —OCH$_2$CF$_3$, —OCF$_2$CHF$_2$, —OCHFCF$_3$, —OCF$_2$CF$_3$, —OCF$_2$CH$_2$CH$_3$, —OCF$_2$CH$_2$CF$_3$, —OCF$_2$CH$_2$CHF$_2$, —OCH$_2$CHFCH$_3$, —OCH$_2$CF$_2$CH$_3$, —OCH$_2$CF$_2$CF$_3$, —OCH$_2$CF$_2$CHF$_2$, —CONH$_2$, —CONHMe, —CONMe$_2$, —C(=O)OMe, —C(=O)OEt, —NHC(=O)H, —NHC(=O)CH$_3$, —NHC(=O)OMe or phenyl.

In some embodiments, each $R^a$ and $R^b$ is independently H, $C_1$-$C_4$ alkyl, $C_3$-$C_4$ alkenyl, $C_3$-$C_4$ alkynyl, $C_1$-$C_4$ haloalkyl, $C_5$-$C_6$ cycloalkyl, ($C_5$-$C_6$ cycloalkyl)-($C_1$-$C_4$ alkylene)-, 5-7 membered heterocyclyl, (5-7 membered heterocyclyl)-($C_1$-$C_4$ alkylene)-, phenyl, phenyl —($C_1$-$C_4$ alkylene)-, 5-6 membered heteroaryl and (5-6 membered heteroaryl)-($C_1$-$C_4$ alkylene)-, or $R^a$ and $R^b$ together with the nitrogen atom they are attached to, form a 5-7 membered heterocyclyl ring; and each $R^c$ and $R^d$ is independently H, $C_1$-$C_4$ alkyl, $C_2$-$C_4$ alkenyl, $C_2$-$C_4$ alkynyl, $C_1$-$C_4$ haloalkyl, $C_5$-$C_6$ cycloalkyl, ($C_5$-$C_6$ cycloalkyl)-($C_1$-$C_4$ alkylene)-, 5-7 membered heterocyclyl, (5-7 membered heterocyclyl)-($C_1$-$C_4$ alkylene)-, phenyl, phenyl-($C_1$-$C_4$ alkylene)-, 5-6 membered heteroaryl and (5-6 membered heteroaryl)-($C_1$-$C_4$ alkylene)-.

In other embodiments, each $R^a$ and $R^b$ is independently H, methyl, ethyl, -(n-Pr), -(i-Pr), -(t-Bu), —CHF$_2$, —CF$_3$, —CH$_2$CF$_3$, —CF$_2$CHF$_2$, —CHFCF$_3$, —CF$_2$CF$_3$, —CF$_2$CH$_2$CH$_3$, —CF$_2$CH$_2$CF$_3$, —CF$_2$CH$_2$CHF$_2$, —CH$_2$CHFCH$_3$, —CH$_2$CF$_2$CH$_3$, —CH$_2$CF$_2$CF$_3$, —CH$_2$CF$_2$CHF$_2$, —CH$_2$CH$_2$Cl, cyclopentyl, pyrrolidinyl, piperidinyl, morpholinyl or piperazinyl, or $R^a$ and $R^b$, together with the nitrogen atom they are attached to, form a 5-7 membered heterocyclyl ring; and each $R^c$ and $R^d$ is independently H, methyl, ethyl, -(n-Pr), -(i-Pr), -(t-Bu), —CHF$_2$, —CF$_3$, —CH$_2$CF$_3$, —CF$_2$CHF$_2$, —CHFCF$_3$, —CF$_2$CF$_3$, —CF$_2$CH$_2$CH$_3$, —CF$_2$CH$_2$CF$_3$, —CF$_2$CH$_2$CHF$_2$, —CH$_2$CHFCH$_3$, —CH$_2$CF$_2$CH$_3$, —CH$_2$CF$_2$CF$_3$, —CH$_2$CF$_2$CF$_3$, —CH$_2$CF$_2$CHF$_2$, —CH$_2$CH$_2$Cl, cyclopentyl, pyrrolidinyl, piperidinyl, morpholinyl or piperazinyl.

In some embodiments, the compound of the invention having one of the following structures or a stereoisomer, a geometric isomer, a tautomer, an N-oxide, a hydrate, a solvate, a metabolite, a pharmaceutically acceptable salt or a prodrug thereof:

(1)

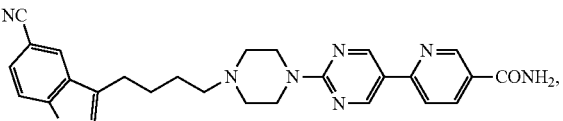

(2)

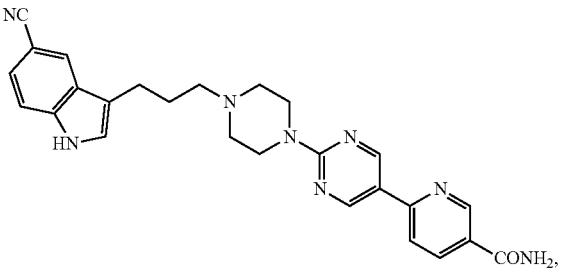

-continued

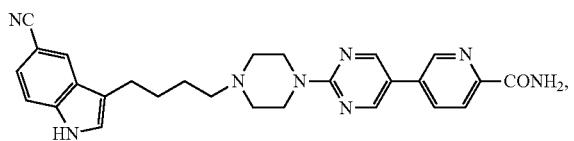
(3)

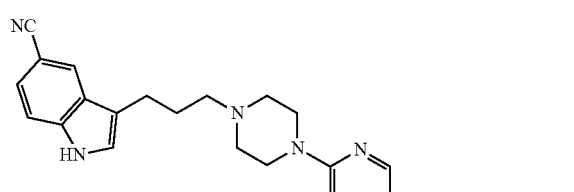
(4)

(5)

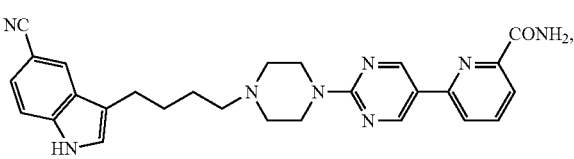
(6)

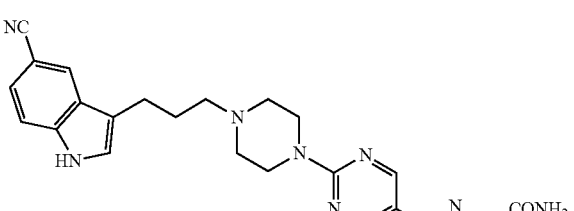
(7)

(8)

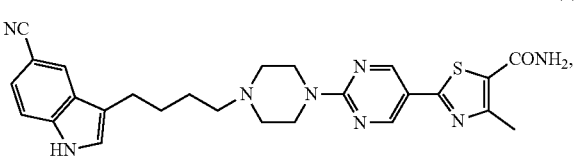
(9)

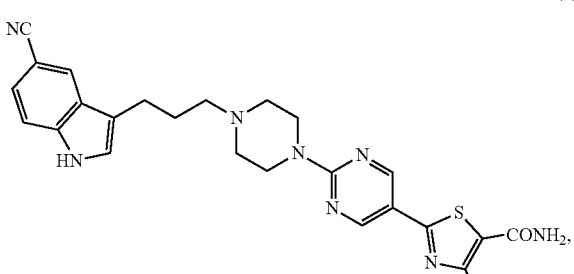

-continued
(10)

(11)

(12)

(13)

or (14)

Unless otherwise stated, all suitable isotope changes, stereoisomers, geometric isomers, tautomers, solvates, metabolites, salts and pharmaceutically acceptable prodrugs of the compounds disclosed herein are within the scope of the invention.

The compound of the present invention may contain asymmetric or chiral centers and therefore may exist in different stereoisomeric forms. It is intended that all stereoisomeric forms of the compounds of Formula (I) to formula (IX) disclosed herein, including, but are not limited to diastereomers, enantiomers, atropisomers, geometries (or conformational) isomers, as well as mixtures thereof such as racemic mixtures, form part of the present invention.

In the structures disclosed herein, when stereochemistry of any particular chiral atom is not indicated, all stereoisomers of the structure are contemplated within the invention, and are included as compound disclosed herein. With the proviso that when stereochemistry is indicated by a solid wedge or dashed line which represents a specific configuration, the stereoisomer of the structure is defined.

The compound of the Formula (I) to (IX) may exist in different tautomeric forms, and all these tautomers are included in the scope of the invention.

Nitrogen oxides of the compound herein are also included in the scope of the invention. The oxynitride of the compound of the invention is prepared by oxidizing the corresponding nitrogen-containing basic substance by using a usual oxidizing agent (for example, hydrogen peroxide) at elevated temperature in the presence of an acid such as acetic acid, or by reacting with a peracid in a suitable solvent, such as dichloromethane, ethyl acetate or methyl acetate, or by reacting with 3-chloroperoxybenzoic acid in chloroform or dichloromethane.

The compound shown in the Formula (I) to (IX) can exist in the form of a salt. In some embodiments, the salt refers to a pharmaceutically acceptable salt. The term "pharmaceutically acceptable" means that the substance or composition must be chemically and/or toxicologically compatible with the other ingredients containing the formulation and/or the mammal treated therewith. In other embodiments, the salt is not necessarily a pharmaceutically acceptable salt, and may be used to prepare and/or purify the compound of Formula (I) to (IX) and/or for separating an intermediate of enantiomer of the compound of Formula (I) to (IX).

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as hydroxide of Na, Ca, Mg, or K, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Furthermore, the compound disclosed herein, including their salts, can also be obtained in the form of their hydrates, or include other solvents such as ethanol, DMSO, and the like, used for their crystallization. The compounds of the present invention may inherently or by design form solvates with pharmaceutically acceptable solvents (including water); therefore, the compounds of the invention include both solvated and unsolvated forms.

Any formula given herein is also intended to represent isotopically unenriched forms as well as isotopically enriched forms of the compounds. Isotopically enriched compounds have the structure depicted by the general formula given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{17}O$, $^{18}O$, $^{18}F$, $^{31}P$, $^{32}P$, $^{35}S$, $^{36}Cl$ and $^{125}I$.

In another aspect, the compound of the invention include isotopically enriched compound as defined herein, for example those into which radioactive isotopes, such as $^3H$, $^{14}C$ and $^{18}F$, or those into which non-radioactive isotopes, such as H and C are present. Such isotopically enriched compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$-enriched compound may be particularly desirable for PET or SPECT studies. Isotopically-enriched compounds of Formula (I) to (IX) can generally be prepared by conventional techniques known to those skilled in the art or by processes analogous to those described in the accompanying examples and preparations using an appropriate isotopically-labeled reagent in place of the non-labeled reagent previously employed.

Further, substitution with heavier isotopes, particularly deuterium (i.e., $^2H$ or D) may afford certain therapeutic advantages resulting from greater metabolic stability. For example, increase in vivo half-life or decrease in dosage requirements or an improvement in therapeutic index. It is understood that deuterium in this context is regarded as a substituent of a compound of Formula (I) to (IX). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g. $D_2O$, $d_6$-acetone, DMSO-$d_6$.

In other aspect, provided herein is an intermediate for preparing the compound of Formula (I) to (IX).

In other aspect, provided herein are methods for preparing, separating, and purifying compounds of Formula (I) to (IX).

In other aspect, provided herein is a pharmaceutical composition comprising the compound disclosed herein. In some embodiments, the pharmaceutical composition disclosed herein further comprises a pharmaceutically acceptable carrier, excipient, diluent, adjuvant and vehicle or any combination thereof. In other embodiments, the pharmaceutical composition can be in the form of a liquid, solid, semi-solid, gel or spray.

Pharmaceutical Composition of the Compound of the Invention and Preparations and Administration The present invention provides a pharmaceutical composition comprising a compound of Formula (I) to (IX) or a single stereoisomer thereof, a racemic or non-racemic mixture of isomer or a pharmaceutically acceptable salt or solvate thereof. In some embodiments of the invention, the pharmaceutical composition further comprises at least one pharmaceutically acceptable carrier, adjuvant, or excipient, and, optionally, other therapeutic and/or prophylactic ingredients.

Suitable carriers, adjuvants and excipients are well known to those skilled in the art and are described in detail, such as Ansel H C et al., Ansel's Pharmaceutical Dosage Forms and Drug Delivery Systems (2004) Lippincott, Williams & Wilkins, Philadelphia; Gennaro A R. Et al., Remington: The Science and Practice of Pharmacy (2000) Lippincott, Williams & Wilkins, Philadelphia; and Rowe R C, Handbook of Pharmaceutical Excipients (2005) Pharmaceutical Press, Chicago.

It will also be appreciated that certain of the compounds of present invention can exist in free form for treatment, or where appropriate, as a pharmaceutically acceptable derivative or a prodrug thereof. Some non-limiting embodiments of pharmaceutically acceptable prodrugs, salts, esters, salts of such esters, or any other adduct or derivative which upon administration to a patient in need thereof is capable of providing, directly or indirectly, a compound as otherwise described herein, or a metabolite or residue thereof.

The pharmaceutical compositions of the invention may be prepared and packaged in bulk form wherein a safe and effective amount of a compound disclosed herein can be extracted and then given to the patient, such as with powders or syrups. Alternatively, the pharmaceutical compositions of the invention may be prepared and packaged in unit dosage form wherein each physically discrete unit contains a safe and effective amount of a compound disclosed herein. When prepared in unit dosage form, the pharmaceutical compositions of the invention commonly contain 0.5 mg to 1 g, or 1 mg to 700 mg, or 5 mg to 100 mg of the compound of the invention.

"Pharmaceutically acceptable excipient" as used herein means a pharmaceutically acceptable material, composition or vehicle involved in dosage form or consistency to the pharmaceutical composition. Each excipient must be compatible with the other ingredients of the pharmaceutical composition when commingled, such that interactions which would substantially reduce the efficacy of the compound of the invention when administered to a patient and would result in pharmaceutically unacceptable compositions are avoided. In addition, each excipient must be pharmaceutically acceptable, for example, with high purity.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound of the present invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

In Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

The pharmaceutical compositions of the invention are prepared by using techniques and methods known to those skilled in the art. Some of the methods commonly used in the art are described in Remington's Pharmaceutical Sciences (Mack Publishing Company).

Therefore, another aspect of the present invention is related to a method for preparing a pharmaceutical composition, the pharmaceutical composition contains the compound disclosed herein and pharmaceutically acceptable excipient, carrier, adjuvant, vehicle or a combination thereof, the method comprises mixing various ingredients. The pharmaceutical composition containing the compound disclosed herein can be prepared by mixing environment temperature and barometric pressure, for example.

The compound of the invention will typically be formulated into a dosage form adapted for administration to the patient by the desired route of administration. For example, dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

In some embodiments, the compound disclosed herein can be prepared to oral administration. In other embodiments, the compound disclosed herein can be prepared to inhalation. In other embodiments, the compound disclosed herein can be prepared to nasal administration. In the yet other embodiments, the compound disclosed herein can be prepared to transdermal administration. In the still yet other embodiments, the compound disclosed herein can be prepared to topical administration.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chew able tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methylparaben and propylparaben, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a diacetal (lower alkyl) of a lower alkyl aldehyde, e.g., acetaldehyde diethyl acetal; and a water-miscible solvent having one or more hydroxy groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or polyalkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

Where appropriate, dosage unit formulations for oral administration can be microencapsulated. The formulation can also be prepared to prolong or sustain the release as for example by coating or embedding particulate material in polymers, wax, or the like.

The pharmaceutical compositions provided herein for oral administration may be also provided in the forms of liposomes, micelles, microspheres, or nanosystems. Micellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The compounds disclosed herein can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine substituted with palmitoyl radicals. The compounds may furthermore be coupled to a class of biodegradable polymers which are suitable for achieving controlled release of a medicament, for example polylactic acid, poly-s-caprolactone, polyhydroxybutyric acid, polyorthoesters, polyacetals, polydihydroxypyrans, polycyanoacrylates and crosslinked or amphipathic block copolymers of hydrogels.

The pharmaceutical compositions provided herein may be formulated as immediate or modified release dosage forms, including delayed-, sustained-, pulsed-, controlled-, targeted-, and programmed-release forms.

The pharmaceutical compositions provided herein may be co-formulated with other active ingredients which do not impair the desired therapeutic action, or with substances that supplement the desired action.

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene dehydrated sorbitol monooleate 80 and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein may be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In some embodiments, the pharmaceutical compositions are provided as ready-to-use sterile solutions. In other embodiments, the pharmaceutical compositions are provided as sterile dry soluble products, including lyophilized powders and hypodermic tablets, to be reconstituted with a vehicle prior to use. In yet other embodiments, the pharmaceutical compositions are provided as ready-to-use sterile suspensions. In yet other embodiments, the pharmaceutical compositions are provided as sterile dry insoluble products to be reconstituted with a vehicle prior to use. In still other embodiments, the pharmaceutical compositions are provided as ready-to-use sterile emulsions.

The pharmaceutical compositions may be formulated as a suspension, solid, semi-solid, or thixotropic liquid, for administration as an implanted depot. In some embodiments, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

In another aspect, the pharmaceutical composition of the invention is prepared to a dosage form adapted for administration to a patient by inhalation, for example as a dry powder, an aerosol, a suspension, or a solution composition. In some embodiments, the pharmaceutical composition of the invention is directed to a dosage form adapted for administration to a patient by inhalation with a dry powder. In other embodiments, the pharmaceutical composition of the invention is directed to a dosage form adapted for administration to a patient by inhalation with a nebulizer. Dry powder compositions for delivery to the lung by inhalation typically comprise a compound disclosed herein or a pharmaceutically acceptable salt thereof as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (e.g. micronised) compound can be defined by a $D_{50}$ value of about 1 to about 10 microns (for example as measured using laser diffraction).

Aerosols may be formed by suspending or dissolving a compound disclosed herein in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound disclosed herein will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 318(1986), 3(6).

Pharmaceutical compositions adapted for topical administration may be formulated as ointments, creams, suspensions, lotions, powders, solutions, pastes, gels, sprays, aerosols or oils. Ointments, creams and gels, may, for example, be formulated with an aqueous or oily base with the addition of suitable thickening and/or gelling agent and/or solvents. Such bases may thus, for example, include water and/or oil such as liquid paraffin or a vegetable oil such as *arachis* oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Topical preparations may be administered by one or more applications per day to the affected area; over skin areas occlusive dressings may advantageously be used. Continuous or prolonged delivery may be achieved by an adhesive reservoir system.

For treatments of the eye or other organs, for example mouth and skin, the compositions may be applied as a topical ointment or cream. When formulated as an ointment, the compound disclosed herein may be employed with either a paraffinic or a water-miscible ointment base. Alternatively, the compound disclosed herein may be formulated as a cream with an oil-in-water cream base or an oil-in-water base.

In some embodiments, the therapeutic method disclosed herein comprises administrating to a patient in need of the treatment a safe and effective amount of the compound of the invention or the pharmaceutical composition containing the compound of the invention. Each example disclosed herein includes the method of treating diseases disclosed herein by administrating to a patient in need of the treatment a safe and effective amount of the compound of the invention or the pharmaceutical composition thereof.

In some embodiments, the compound of the invention or the pharmaceutical composition thereof may be administered by any suitable route of administration, including both systemic administration and topical administration. Systemic administration includes oral administration, parenteral administration, transdermal administration and rectal administration. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, otic, intravaginal, inhaled and intranasal administration. In some embodiments, the compound of the invention or the pharmaceutical composition thereof may be administered orally. In other embodiments, the compound of the invention or the pharmaceutical composition thereof may be administered by inhalation. In still other embodiments, the compound of the invention or the pharmaceutical composition thereof may be administered intranasally.

In some embodiments, the compound of the invention or the pharmaceutical composition thereof may be administered once or according to a dosing regimen wherein a number of doses are administered at varying intervals of time for a given period of time. For example, doses may be administered one, two, three, or four times per day. In some embodiments, a dose is administered once per day. In still other embodiments, a dose is administered twice per day. Doses may be administered until the desired therapeutic effect is achieved or indefinitely to maintain the desired therapeutic effect. Suitable dosing regimens for the compound of the invention or the pharmaceutical composition thereof depend on the pharmacokinetic properties of that compound, such as absorption, distribution, and half-life, which can be determined by the skilled artisan. In addition, suitable dosing regimens, including the duration such regimens are administered, for the compound of the invention or the pharmaceutical composition thereof depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

The compound of the present invention may be administered either simultaneously with, or before or after, one or more other therapeutic agents. The compound of the present invention may be administered separately by the same or different routes of administration with other agents, or in the same pharmaceutical composition.

The pharmaceutical composition or combination of the present invention can be in unit dosage of about 1-1000 mg of active ingredients for a subject of about 50-70 kg, preferably about 1-500 mg or about 1-250 mg or about 1-150 mg or about 0.5-100 mg or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and specimens thereof. The compound of the invention can be applied in vitro in the form of solutions, e.g., preferably aqueous solutions, and in vivo either enterally, parenterally, advantageously intravenously, e.g., as a suspension or in aqueous solution.

In some embodiments, a therapeutically effective dosage of the compound disclosed herein from about 0.1 mg to about 2,000 mg per day. The pharmaceutical composition should provide a dosage of from about 0.1 mg to about 2,000 mg of the compound. In a special embodiment, pharmaceutical dosage unit forms are prepared to provide from about 1 mg to about 2,000 mg, about 10 mg to about 1,000 mg, about 20 mg to about 500 mg, or about 25 mg to about 250 mg of the active ingredient or a combination of essential ingredients per dosage unit form. In a special embodiment, pharmaceutical dosage unit forms are prepared to provide about 10 mg, 20 mg, 25 mg, 50 mg, 100 mg, 250 mg, 500 mg, 1,000 mg or 2,000 mg of the active ingredient.

Additionally, the compound of the invention may be administered as a prodrug. As used herein, a "prodrug" of the compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of action of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

Use of the Compounds and Pharmaceutical Compositions

The compound and pharmaceutical composition provided herein can be used for preparing drugs for preventing, treating or ameliorating central nervous system dysfunction in mammals, including human, and for preparing drugs for inhibiting the reuptake of 5-hydroxytryptamine and/or activating $5\text{-HT}_{1A}$ receptors.

Specifically, the amount of the compound in the composition of the present invention can effectively and detectably inhibit the reuptake of 5-hydroxytryptamine selectively and active the $5\text{-HT}_{1A}$ receptors, and the compound of the present invention can be used as a drug for treating human central nervous system (CNS) dysfunction such as depression and anxiety disorder.

The compound of the invention can be applied, but are not limited to preventing, treating or ameliorating central nervous system dysfunction by administering to the patient in an effective amount of the compound or composition disclosed herein. The central nervous system dysfunction disease that respond to the regulation of 5-hydroxytryptamine receptors further include, but are not limited to, depression, anxiety, mania, schizophrenia, sleep disorder, bipolar disorder, obsessive-compulsive and behavioral disorder, panic disorder, post-traumatic stress disorder, motor disorder, sexual dysfunction, musculoskeletal pain disorder, cognitive impairment, memory impairment, Parkinson's disease, Huntington's disease, phobia, substance abuse or addiction, drug addiction withdrawal symptoms and premenstrual stress syndrome.

Besides being useful for human treatment, the compound and pharmaceutical composition of the present invention are also useful for veterinary treatment of pets, introduced species of animals, and mammals in farm animals. In other embodiments, the animals disclosed herein include horses, dogs, and cats. As used herein, the compound disclosed herein include the pharmaceutically acceptable derivatives thereof.

General Synthetic Methods of the Compounds of the Invention

For the purpose of describing the invention, the examples are listed below. It is to be understood that the invention is not limited to the embodiments, merely provides a method of practicing the invention.

Generally, the compound disclosed herein may be prepared by methods described herein, wherein the substituents are as defined for Formula (I) to (IX) above, except where further stated. The following schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin Yu Yu Fine Chemical Ltd., Tianjin Fuchen Reagent Chemical Factory, Wuhan Xinhuayuan Technology Development Co., Ltd., Qingdao Tenglong Reagent Chemical Ltd., and Qingdao Ocean Chemical Factory.

Anhydrous THF, dioxane, toluene, and ether were obtained by refluxing the solvent with sodium. Anhydrous CH$_2$Cl$_2$ and CHCl$_3$ were obtained by refluxing the solvent with CaH$_2$. Ethyl acetate, petroleum ether, n-hexane, N,N-dimethylacetamide and N,N-dimethylformamide were treated with anhydrous Na$_2$SO$_4$ prior to use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory.

$^1$H NMR spectrums were recorded on a Bruker 400 MHz or 600 MHz NMR spectrometer. $^1$H NMR spectrums were obtained by using CDCl$_3$, d$_6$-DMSO, CD$_3$OD or d$_6$-acetone as solvents (reported in ppm), with TMS (0 ppm) or chloroform (7.26 ppm) as the reference standard. When peak multiplicities were reported, the following abbreviations are used: s (singlet), d (doublet), t (triplet), q (quartet), m (multiplet), br (broadened), brs (broadened singlet), dd (doublet of doublets), dt (doublet of triplets). Coupling constants J were reported in Hertz (Hz).

The determination conditions for the low resolution mass spectrometry (MS) data were: Agilent 6120 quadrupole HPLC-MS (column model: Zorbax SB-C18, 2.1×30 mm, 3.5 microns, 6 min, 0.6 mL/min of flow rate). The mobile phase: 5%-95% (CH$_3$CN containing 0.1% formic acid) in a ratio of (H$_2$O containing 0.1% formic acid) by electrospray ionization (ESI) and UV detection at 210 nm/254 nm.

Pure compounds were detected by UV using an Agilent 1260 pre-HPLC or Calesep pump 250 pre-HPLC (column model: NOVASEP 50/80 mm DAC) at 210 nm/254 nm.

The following abbreviations are used throughout the specification:
CDCl$_3$ chloroform-d
DMSO dimethylsulfoxide
DMSO-d$_6$ deuterated dimethylsulfoxide
CH$_3$CN acetonitrile
H$_2$O water
Boc, BOC t-Butyloxy carbonyl
mmol millimole
mg milligram
g gram
min minute
h hour
MgSO$_4$ magnesium sulfate
NaCl sodium chloride
KCl potassium chloride
EDTA ethylenediamine tetraacetic acid
HCl hydrochloric acid
H$_3$PO$_4$ phosphoric acid
μL, μl microlitres
mL, ml milliliter
mM millimole per liter
μM micromolar per liter
nM nanomer per liter
PEI polyethylenimine
BSA bovine serum albumin
Tris-HCl Tris(hydroxymethyl)aminomethane-hydrochloric acid
Saline normal saline
aprotinine aprotinin
HP-β-CD hydroxypropyl-β-cyclodextrin The following synthetic schemes describe the steps for preparing the compound of the invention. Unless otherwise stated, n, Y and R$^1$ have the definitions as described herein.

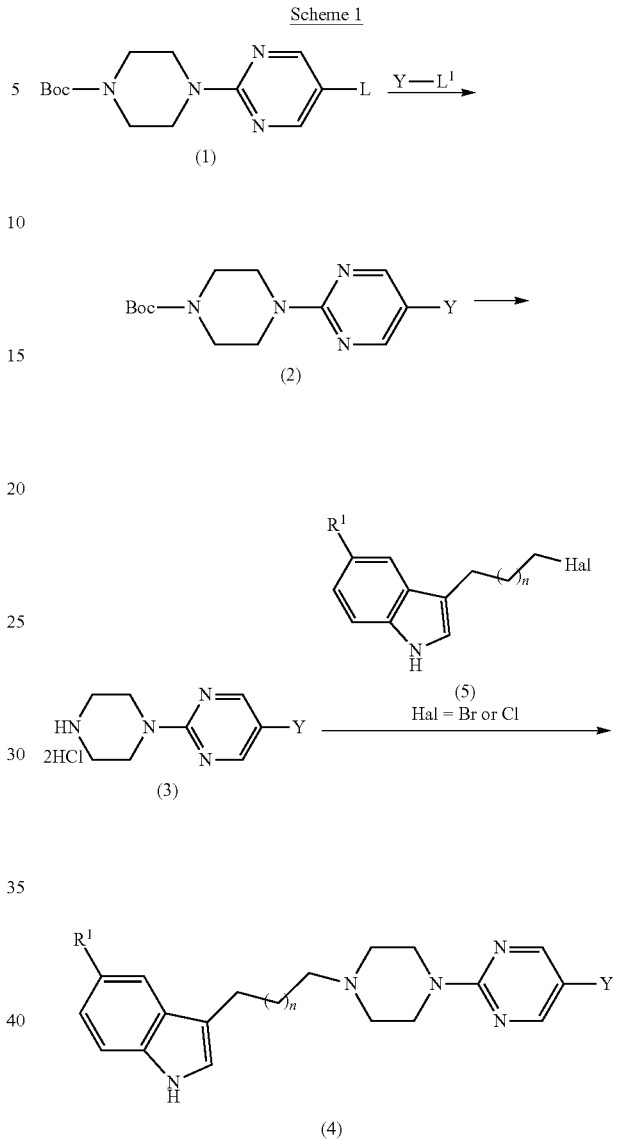

Wherein, when L is a halogen group such as Br or Cl, L$^1$ is a boric acid or a boronic acid pinacol ester; or, when L is a boric acid or a boronic acid pinacol ester, L$^1$ is a halogen group such as Br or Cl.

Compound (4) can be obtained by the general synthetic method illustrated in Scheme 1, and which was described in detail in embodiments: Firstly, reaction of compound (1) and compound Y-L$^1$ under a condition of palladium analysis can give compound (2); and then compound (2) can be suffered from deprotection of the Boc protecting group under acidic conditions to give compound (3); finally, reaction of compound (3) and compound (5) under basic conditions can give the objective compound (4).

The compounds, pharmaceutical compositions, and uses thereof provided by the present invention are further illustrated below in conjunction with the embodiments.

EXAMPLES

Example 1 Synthesis of 6-(2-(4-(4-(5-cyano-1H-indol-3-yl)butyl)piperazin-1-yl) pyrimidin-5-yl)nicotinamide

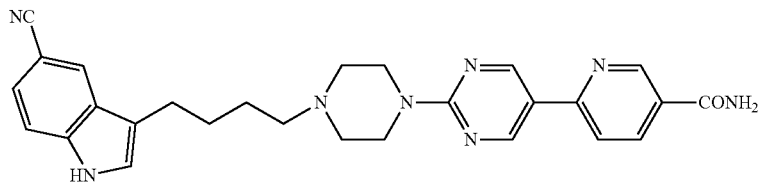 [SMILES: N#Cc1ccc2[nH]cc(CCCCN3CCN(c4ncc(-c5ccc(C(N)=O)cn5)cn4)CC3)c2c1]

Step 1) Synthesis of t-butyl 4-(5-(5-carbamoylpyridin-2-yl)pyrimidin-2-yl)piperazine-1-formate 2-[4-(Boc)piperazin-1-yl]pyrimidine-5-boronic acid pinacol ester (1.00 g, 2.56 mmol), 6-bromopyridine-3-carboxamide (0.62 g, 3.08 mmol), Tricyclohexylphosphine (0.11 g, 0.38 mmol), tris(dibenzylideneacetone)palladium(0) (0.12 g, 0.13 mmol) and potassium phosphate (1.73 g, 5.11 mmol) were added into a mixture of 1,4-dioxane (10 mL) and water (1 mL) in turn. The reaction mixture was heated to 100° C. overnight under $N_2$. The reaction was stopped, and the mixture was cooled to room temperature. The solvent was evaporated under reduced pressure. The residue was separated and purified by column chromatography (methylene chloride/methanol (v/v)=40/1) to give the title compound as a white solid (0.77 g, 78.2%).

MS (ESI, pos. ion) m/z: 385.60 [M+H]$^+$.

$^1$H NMR (400 MHz, DMSO-d$_6$) δ (ppm): 9.12 (s, 2H), 9.05 (d, J=1.8 Hz, 1H), 8.25 (dd, J=8.4, 2.2 Hz, 1H), 8.15 (s, 1H), 8.01 (d, J=8.3 Hz, 1H), 7.58 (s, 1H), 3.91~3.76 (m, 4H), 3.43 (dd, J=14.9, 10.1 Hz, 4H), 1.44 (s, 9H).

Step 2) Synthesis of 6-(2-(piperazin-1-yl)pyrimidin-5-yl)nicotinamide dihydrochloride t-Butyl 4-(5-(5-carbamoylpyridin-2-yl)pyrimidin-2-yl)piperazine-1-formate (0.77 g, 2.0 mmol) was added to dichloromethane (10 mL). And then a solution of hydrogen chloride in ethyl acetate (6 mL, 3.2 mol/L) was added. After the end of addition, the mixture was reacted for 4 hours at room temperature. The reaction was stopped. The solvent was evaporated under reduced pressure to give the title compound as a faint yellow solid (0.72 g, 99.9%).

MS (ESI, pos. ion) m/z: 285.50 [M+H]$^+$.

Step 3) Synthesis of 6-(2-(4-(4-(5-cyano-1H-indol-3-yl)butyl)piperazin-1-yl)pyrimidin-5-yl) nicotinamide 6-(2-(Piperazin-1-yl)pyrimidin-5-yl)nicotinamide dihydrochloride (400 mg, 1.12 mmol), 3-(4-chlorobutyl)-1H-indole-5-nitrile (312 mg, 1.34 mmol), anhydrous sodium carbonate (712 mg, 6.72 mmol) and sodium iodide (50 mg, 0.33 mmol) were added into anhydrous acetonitrile (15 mL) in turn. The solution was heated to 90° C. and reacted for 36 hours. The reaction was stopped, and the mixture was cooled to room temperature. The solvent was evaporated under reduced pressure. The residue was purified by column chromatography (dichloromethane/methanol (v/v)=20/1) to give the title compound as a faint yellow solid (465 mg, 86.4%).

MS (ESI, pos. ion) m/z: 481.30 [M+H]$^+$.

$^1$H NMR (400 MHz, DMSO-d$_6$) δ (ppm): 11.36 (s, 1H), 9.08 (s, 2H), 9.04 (d, J=1.7 Hz, 1H), 8.26 (dd, J=8.3, 2.1 Hz, 1H), 8.14 (s, 1H), 8.10 (s, 1H), 8.05 (d, J=8.3 Hz, 1H), 7.52 (s, 1H), 7.49 (d, J=8.3 Hz, 1H), 7.40 (dd, J=8.4, 0.9 Hz, 1H), 7.35 (s, 1H), 3.90 (brs, 4H), 3.39 (brs, 4H), 2.73 (t, J=7.4 Hz, 2H), 2.45~2.39 (m, 2H), 1.73~1.65 (m, 2H), 1.54 (d, J=6.7 Hz, 2H);

HPLC: 95.11%.

Example 2 Synthesis of 6-(2-(4-(3-(5-cyano-1H-indol-3-yl)propyl)piperazin-1-yl)pyrimidin-5-yl) nicotinamide

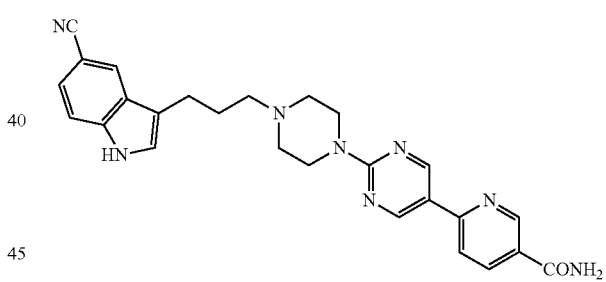

The title compound of this step was prepared by the method described in Step 3 of Example 1, namely, 6-(2-(piperazin-1-yl)pyrimidin-5-yl)nicotinamide dihydrochloride (400 mg, 1.12 mmol), 3-(3-chloropropyl)-1H-indole-5-nitrile (295 mg, 1.34 mmol), anhydrous sodium carbonate (712 mg, 6.72 mmol) and sodium iodide (50 mg, 0.33 mmol) were added to anhydrous acetonitrile (15 mL). The solution was heated to 90° C. and reacted for 36 hours. The crude product was purified by column chromatography (dichloromethane/methanol (v/v)=20/1) to give the title compound as a faint yellow solid (350 mg, 67.0%).

MS (ESI, pos. ion) m/z: 467.30 [M+H]$^+$.

$^1$H NMR (600 MHz, DMSO-d$_6$) δ (ppm): 11.40 (s, 1H), 9.11 (s, 2H), 9.05 (d, J=1.7 Hz, 1H), 8.25 (dd, J=8.3, 2.1 Hz, 1H), 8.15 (s, 1H), 8.11 (s, 1H), 8.01 (d, J=8.3 Hz, 1H), 7.58 (s, 1H), 7.51 (d, J=8.4 Hz, 1H), 7.41 (dd, J=8.4, 0.9 Hz, 1H), 7.37 (s, 1H), 3.87 (brs, 4H), 2.77 (t, J=7.4 Hz, 2H), 2.55 (brs, 4H), 2.53 (d, J=23.3 Hz, 2H), 2.42 (d, J=34.5 Hz, 2H), 1.88 (dd, J=19.8, 13.1 Hz, 2H);

HPLC: 99.15%.

Example 3 Synthesis of 5-(2-(4-(4-(5-cyano-1H-indol-3-yl)butyl)piperazin-1-yl)pyrimidin-5-yl)pyridine-2-carboxamide

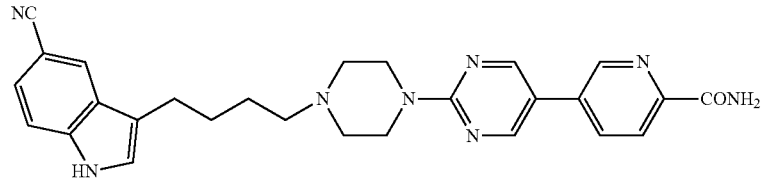

Step 1) Synthesis of t-butyl 4-(5-(6-cyanopyridin-3-yl)pyrimidin-2-yl)piperazine-1-formate t-Butyl 4-(5-bromopyrimidin-2-yl)piperazine-1-formate (2.00 g, 5.83 mmol), (6-cyano-3-pyridyl)boronic acid (1.04 g, 7.03 mmol), sesium carbonate (2.01 g, 14.5 mmol) and [1,1'-bis(diphenylphosphino)ferrocene]palladium(II) chloride (220 mg, 0.29 mmol) were added to a mixed solvent of 1,4-dioxane (30 mL) and water (3 mL), the mixture was heated to 100° C. and reacted for 18 hours under $N_2$. The reaction was stopped, and the mixture was cooled to room temperature. The solvent was evaporated under reduced pressure. The residue was purified by column chromatography (dichloromethane/methanol (v/v)=50/1) to give the title compound as a faint yellow solid (1.02 g, 47.8%).

MS (ESI, pos. ion) m/z: 312.10 [M+H−56]+;

$^1$H NMR (400 MHz, CDCl$_3$) δ (ppm): 8.88 (d, J=1.7 Hz, 1H), 8.61 (s, 2H), 7.93 (dd, J=8.1, 2.3 Hz, 1H), 7.77 (d, J=8.1 Hz, 1H), 3.96-3.88 (m, 4H), 3.57-3.50 (m, 4H), 1.51 (s, 9H).

Step 2) Synthesis of t-butyl 4-(5-(6-carbamoyl pyridin-3-yl)pyrimidin-2-yl)piperazine-1-formate t-Butyl 4-(5-(6-cyanopyridin-3-yl)pyrimidin-2-yl)piperazine-1-formate (1.02 g, 2.78 mmol) and potassium carbonate (77 mg, 5.56 mmol) were added to dimethyl sulfoxide (20 mL) in turn. And then 30% hydrogen peroxide (0.63 mL, 11.1 mmol) was slowly added to the mixture under a condition of ice bath. After the end of addition, the mixture was warmed to room temperature and reacted for 4 hours. The reaction was stopped. The reaction solution was diluted with water (100 mL), suction filtered, and a solid was collected. The crude product was purified by column chromatography (dichloromethane/methanol (v/v)=30/1) to give the title compound as a faint yellow solid (0.82 g, 76.6%).

MS (ESI, pos. ion) m/z: 385.15 [M+H]+.

$^1$H NMR (400 MHz, DMSO-d$_6$) δ (ppm): 8.94 (s, 1H), 8.89 (d, J=10.1 Hz, 2H), 8.26 (d, J=6.1 Hz, 1H), 8.15~8.04 (m, 2H), 7.65 (s, 1H), 3.81 (brs, 4H), 3.43 (brs, 4H), 1.39 (s, 9H).

Step 3) Synthesis of 5-(2-(piperazin-1-yl)pyrimidin-5-yl)pyridine-2-carboxamide dihydrochloride The title compound of this step was prepared by the method described in Example 1, Step 2, namely, t-butyl 4-(5-(6-carbamoylpyridin-3-yl)pyrimidin-2-yl)piperazine-1-formate (0.82 g, 2.13 mmol) and a solution of hydrogen chloride in ethyl acetate (6 mL, 3.2 mol/L) were added to dichloromethane (10 mL). Then the mixture was reacted for 4 hours at room temperature. The solvent was evaporated under reduced pressure to give the title compound as a faint yellow solid (0.76 g, 99.9%).

MS (ESI, pos. ion) m/z: 285.40 [M+H]+.

Step 4) Synthesis of 5-(2-(4-(4-(5-cyano-1H-indol-3-yl)butyl)piperazin-1-yl)pyrimidin-5-yl)pyridine-2-carboxamide The title compound of this step was prepared by the method described in Example 1, Step 3, namely, 5-(2-(piperazin-1-yl)pyrimidin-5-yl)pyridine-2-carboxamide dihydrochloride (400 mg, 1.12 mmol), 3-(4-chlorobutyl)-1H-indole-5-nitrile (312 mg, 1.34 mmol), anhydrous sodium carbonate (712 mg, 6.72 mmol) and sodium iodide (50 mg, 0.33 mmol) were added to anhydrous acetonitrile (15 mL). The mixture solution was heated to 90° C. and reacted for 36 hours. The crude product was separated and purified by column chromatography (dichloromethane/methanol (v/v)=20/1) to give the title compound as a white solid (390 mg, 73.6%).

MS (ESI, pos. ion) m/z: 481.70 [M+H]+.

$^1$H NMR (600 MHz, DMSO-d$_6$) δ (ppm): 11.36 (s, 1H), 8.92 (s, 1H), 8.83 (s, 2H), 8.31~8.18 (m, 1H), 8.07 (d, J=10.5 Hz, 3H), 7.63 (s, 1H), 7.50 (d, J=8.4 Hz, 1H), 7.40 (d, J=8.4 Hz, 1H), 7.34 (s, 1H), 3.80 (brs, 4H), 2.74 (t, J=7.3 Hz, 2H), 2.42 (brs, 4H), 2.37 (t, J=7.0 Hz, 2H), 1.67 (dd, J=14.6, 7.4 Hz, 2H), 1.54 (d, J=6.6 Hz, 2H);

HPLC: 99.42%.

Example 4 Synthesis of 5-(2-(4-(3-(5-cyano-1H-indol-3-yl)propyl)piperazin-1-yl)pyrimidin-5-yl)pyridine-2-carboxamide

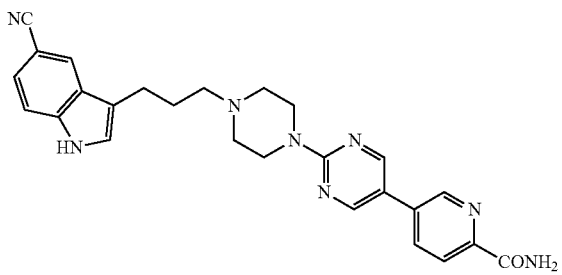 [SMILES: N#Cc1ccc2[nH]cc(CCCN3CCN(c4ncc(-c5ccc(C(N)=O)nc5)cn4)CC3)c2c1]

The title compound of this step was prepared by the method described in Example 1, Step 3, namely, 5-(2-(piperazin-1-yl)pyrimidin-5-yl)pyridine-2-carboxamide dihydrochloride (450 mg, 1.26 mmol), 3-(3-chloropropyl)-1H-indole-5-nitrile (330 mg, 1.51 mmol), anhydrous sodium carbonate (802 mg, 7.57 mmol) and sodium iodide (56 mg, 0.37 mmol) were added to anhydrous acetonitrile (15 mL). The mixture solution was heated to 90° C. and reacted for 36 hours. The crude product was purified by column chromatography (dichloromethane/methanol (v/v)=20/1) to give the title compound as a white solid (380 mg, 64.6%).

MS (ESI, pos. ion) m/z: 467.15 [M+H]$^+$.

$^1$H NMR (600 MHz, DMSO-d$_6$) δ (ppm): 11.38 (s, 1H), 8.90 (s, 1H), 8.85 (s, 2H), 8.33~8.23 (m, 1H), 8.05 (d, J=10.7 Hz, 3H), 7.65 (s, 1H), 7.50 (d, J=8.3 Hz, 1H), 7.41 (d, J=8.5 Hz, 1H), 7.33 (s, 1H), 3.82 (brs, 4H), 2.74 (t, J=7.1 Hz, 2H), 2.49~2.40 (m, 2H), 2.44 (brs, 4H), 1.93~1.81 (m, 2H);

HPLC: 95.14%.

Example 5 Synthesis of 6-(2-(4-(4-(5-cyano-1H-indol-3-yl)butyl)piperazin-1-yl)pyrimidin-5-yl)pyridine-2-carboxamide

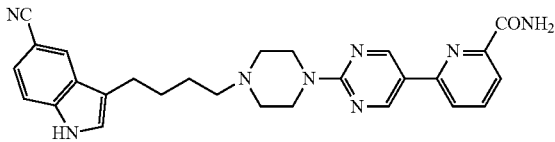 [SMILES: N#Cc1ccc2[nH]cc(CCCCN3CCN(c4ncc(-c5cccc(C(N)=O)n5)cn4)CC3)c2c1]

Step 1) Synthesis of t-butyl 4-(5-(6-cyanopyridin-2-yl)pyrimidin-2-yl)piperazine-1-formate The title compound of this step was prepared by the method described in Example 1, Step 1, namely, 2-[4-(Boc)piperazin-1-yl]pyrimidine-5-boronic acid pinacol ester (2.70 g, 6.93 mmol), 6-chloropyridine-2-nitrile (0.80 g, 5.77 mmol), tricyclohexylphosphine (0.16 g, 0.58 mmol), tris(dibenzylideneacetone)palladium(0) (0.17 g, 0.29 mmol) and potassium phosphate (2.50 g, 11.55 mmol) were added to a mixture of 1,4-dioxane (20 mL) and water (2 mL). The reaction was heated to 100° C. overnight under N$_2$. The crude product was purified by column chromatography (dichloromethane/methanol (v/v)=40/1) to give the title compound as a yellow solid (1.84 g, 87.0%).

MS (ESI, pos. ion) m/z: 311.40 [M+H−56]$^+$;

$^1$H NMR (400 MHz, CDCl$_3$) δ (ppm): 8.97 (s, 2H), 7.90~7.83 (m, 1H), 7.80 (dd, J=8.1, 0.9 Hz, 1H), 7.58 (dd, J=7.4, 0.9 Hz, 1H), 3.97~3.86 (m, 4H), 3.58~3.46 (m, 4H), 1.51 (s, 9H).

Step 2) Synthesis of t-butyl 4-(5-(6-carbamoylpyridin-2-yl)pyrimidin-2-yl) piperazine-1-formate The title compound of this step was prepared by the method described in Example 3, Step 2, namely, t-butyl 4-(5-(6-cyanopyridin-2-yl)pyrimidin-2-yl)piperazine-1-formate (2.00 g, 5.46 mmol), potassium carbonate (0.15 g, 1.09 mmol) and 30% hydrogen peroxide (2.19 mL, 21.8 mmol) were added to dimethyl sulfoxide (40 mL). Then the mixture was reacted for 4 hours at room temperature. The crude product was separated and purified by column chromatography (dichloromethane/methanol (v/v)=30/1) to give the title compound as a white solid (2.01 g, 95.8%).

MS (ESI, pos. ion) m/z: 385.60 [M+H]$^+$.

$^1$H NMR (400 MHz, DMSO-d$_6$) δ (ppm): 9.31 (s, 2H), 8.41 (s, 1H), 8.09 (d, J=7.3 Hz, 1H), 8.00 (t, J=7.8 Hz, 1H), 7.92 (d, J=7.5 Hz, 1H), 7.65 (s, 1H), 3.90~3.77 (m, 4H), 3.50~3.40 (m, 4H), 1.43 (s, 9H).

Step 3) Synthesis of 6-(2-(piperazin-1-yl)pyrimidin-5-yl)pyridine-2-carboxamide dihydrochloride The title compound of this step was prepared by the method described in Example 1, Step 2, namely, t-butyl 4-(5-(6-carbamoylpyridin-2-yl)pyrimidin-2-yl)piperazine-1-formate (2.00 g, 5.20 mmol) and a solution of hydrogen chloride in ethyl acetate (15 mL, 3.2 mol/L) were added to dichloromethane (20 mL). Then the mixture was reacted for 4 hours at room temperature. The solvent was evaporated under reduced pressure to give the title compound as a faint yellow solid (1.85 g, 99.5%).

MS (ESI, pos. ion) m/z: 285.50 [M+H]$^+$.

Step 4) Synthesis of 6-(2-(4-(4-(5-cyano-1H-indol-3-yl)butyl)piperazin-1-yl)pyrimidin-5-yl)pyridine-2-carboxamide The title compound of this step was prepared by the method described in Example 1, Step 3, namely, 6-(2-(piperazin-1-yl)pyrimidin-5-yl)pyridine-2-carboxamide dihydrochloride (400 mg, 1.12 mmol), 3-(4-chlorobutyl)-1H-indole-5-nitrile (286 mg, 1.23 mmol), anhydrous sodium carbonate (712 mg, 6.72 mmol) and sodium iodide (50 mg, 0.33 mmol) were added to anhydrous acetonitrile (15 mL). The mixture solution was heated to 90° C. and reacted for 36 hours. The crude product was separated and purified by column chromatography (dichloromethane/methanol (v/v)=20/1) to give the title compound as a white solid (420 mg, 72.6%).

MS (ESI, pos. ion) m/z: 481.70 [M+H]$^+$.

$^1$H NMR (400 MHz, DMSO-d$_6$) δ (ppm): 11.37 (s, 1H), 9.28 (s, 2H), 8.41 (s, 1H), 8.08 (d, J=6.6 Hz, 2H), 8.00 (t, J=7.8 Hz, 1H), 7.91 (d, J=7.5 Hz, 1H), 7.65 (s, 1H), 7.50 (d, J=8.4 Hz, 1H), 7.40 (dd, J=8.4, 1.4 Hz, 1H), 7.34 (d, J=1.8 Hz, 1H), 3.84 (brs, 4H), 3.37 (brs, 4H), 2.74 (t, J=7.3 Hz, 2H), 2.46~2.36 (m, 2H), 1.74~1.62 (m, 2H), 1.56 (d, J=6.7 Hz, 2H);

HPLC: 99.53%.

Example 6 Synthesis of 6-(2-(4-(3-(5-cyano-1H-indol-3-yl)propyl)piperazin-1-yl)pyrimidin-5-yl)pyridine-2-carboxamide

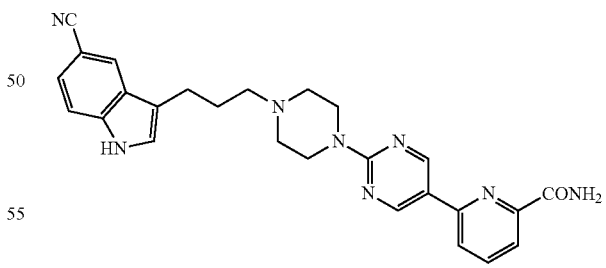

The title compound of this step was prepared by the method described in Example 1, Step 3, namely, 6-(2-(piperazin-1-yl)pyrimidin-5-yl)pyridine-2-carboxamide dihydrochloride (500 mg, 1.40 mmol), 3-(3-chloropropyl)-1H-indole-5-nitrile (367 mg, 1.68 mmol), anhydrous sodium carbonate (890 mg, 8.40 mmol) and sodium iodide (62 mg, 0.41 mmol) were added to anhydrous acetonitrile (15 mL). The mixture solution was heated to 90° C. and reacted for 36 hours. The crude product was separated and purified by column chromatography (dichloromethane/methanol (v/v) =20/1) to give the title compound as a white solid (462 mg, 70.4%).

MS (ESI, pos. ion) m/z: 467.70 [M+H]⁺;
¹H NMR (400 MHz, DMSO-d₆) δ (ppm): 11.39 (s, 1H), 9.28 (s, 2H), 8.41 (s, 1H), 8.15~8.05 (m, 2H), 8.00 (t, J=7.7 Hz, 1H), 7.91 (d, J=7.5 Hz, 1H), 7.65 (s, 1H), 7.50 (d, J=8.4 Hz, 1H), 7.41 (dd, J=8.4, E4 Hz, 1H), 7.36 (d, J=E6 Hz, 1H), 3.86 (brs, 4H), 3.37 (brs, 4H), 2.76 (t, J=7.3 Hz, 2H), 2.41 (s, 2H), 1.93-1.77 (m, 2H);
HPLC: 95.88%.

Example 7 Synthesis of 2-(2-(4-(4-(5-cyano-1H-indol-3-yl)butyl)piperazin-1-yl)pyrimidin-5-yl)-4-methylthiazole-5-formamide

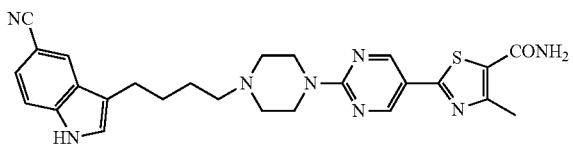 [SMILES: Cc1nc(-c2cnc(N3CCN(CCCCc4c[nH]c5ccc(C#N)cc45)CC3)nc2)oc1C(N)=O]

Step 1) Synthesis of t-butyl 4-(5-(5-carbamoyl-4-methylthiazol-2-yl)pyrimidin-2-yl) piperazine-1-formate 2-(4-Boc-piperazin-1-yl)pyrimidine-5-boronic acid pinacol ester (1.40 g, 3.59 mmol), 2-bromo-4-methylthiazole-5-carboxamide (0.96 g, 4.34 mmol), cesium carbonate (2.98 g, 8.96 mmol) and [1,1'-bis(diphenylphosphino)ferrocene]palladium dichloride (II) (134 mg, 0.18 mmol) were added to a mixed solvent of 2-methyltetrahydrofuran (15 mL) and water (3 mL), the mixture was heated to 100° C. and reacted overnight under N₂. The reaction was stopped, and the mixture was cooled to room temperature. The solvent was evaporated under reduced pressure. The crude product was purified by a silica gel column chromatography (dichloromethane/methanol (v/v)=40/1) to give the title compound as a faint yellow solid (1.02 g, 70.3%).

MS (ESI, pos. ion) m/z: 405.25 [M+H]⁺;
¹H NMR (400 MHz, DMSO-d₆) δ (ppm): 8.86 (s, 2H), 7.59 (s, 2H), 3.88~3.77 (m, 4H), 3.43 (dd, J=11.3, 6.7 Hz, 4H), 2.59 (s, 3H), 1.43 (s, 9H).

Step 2) Synthesis of 4-methyl-2-(2-(piperazin-1-yl)pyrimidin-5-yl)thiazole-5-carboxamide dihydrochloride The title compound of this step was prepared by the method described in Example 1, Step 2, namely, t-butyl 4-(5-(5-carbamoyl-4-methylthiazolyl-2-methyl)pyrimidin-2-yl)piperazine-1-formate (1.02 g, 2.52 mol) and a solution of hydrogen chloride in ethyl acetate (8.0 mL, 3.2 mol/L) were added to dichloromethane (10 mL). Then the mixture was reacted for 4 hours at room temperature. The solvent was evaporated under reduced pressure to give the title compound as a faint yellow solid (0.95 g, 99.8%).

MS (ESI, pos. ion) m/z: 305.20 [M+H]⁺;

Step 3) Synthesis of 2-(2-(4-(4-(5-cyano-1H-indol-3-yl)butyl)piperazin-1-yl)pyrimidin-5-yl)-4-methylthiazole-5-formamide The title compound of this step was prepared by the method described in Example 1, Step 3, namely, 4-methyl-2-(2-(piperazin-1-yl)pyrimidin-5-yl)thiazole-5-carboxamide dihydrochloride (1.68 g, 4.45 mmol), 3-(4-chlorobutyl)-1H-indole-5-nitrile (1.24 g, 5.35 mmol), anhydrous sodium carbonate (2.83 g, 26.7 mmol) and sodium iodide (0.20 g, 1.33 mmol) were added to anhydrous acetonitrile (50 mL). The mixture solution was heated to 90° C. and reacted for 36 hours. The residue was further purified by a silica gel column chromatography (dichloromethane/methanol (v/v)=30/1) to give the title compound as a faint yellow solid (1.76 g, 78.8%).

MS (ESI, pos. ion) m/z: 501.25 [M+H]⁺;
¹H NMR (600 MHz, DMSO-d₆) δ (ppm): 11.36 (s, 1H), 8.83 (s, 2H), 8.12 (s, 1H), 7.58 (s, 2H), 7.50 (d, J=8.4 Hz, 1H), 7.40 (d, J=8.4 Hz, 1H), 7.34 (s, 1H), 3.82 (brs, 4H), 2.76 (t, J=7.4 Hz, 2H), 2.61 (s, 3H), 2.42 (brs, 4H), 2.39 (t, J=7.0 Hz, 2H), 1.65 (dd, J=14.5, 7.3 Hz, 2H), 1.52 (d, J=6.7 Hz, 2H);
HPLC: 99.32%.

Example 8 Synthesis of 2-(2-(4-(3-(5-cyano-1H-indol-3-yl)propyl)piperazin-1-yl)pyrimidin-5-yl)-4-methylthiazole-5-formamide

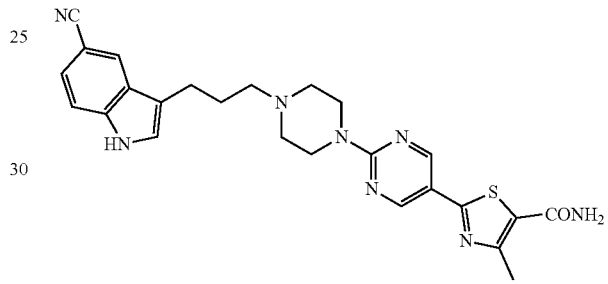

The title compound of this step was prepared by the method described in Example 1, Step 3, namely, 4-methyl-2-(2-(piperazin-1-yl)pyrimidin-5-yl)thiazole-5-carboxamide dihydrochloride (1.68 g, 4.45 mmol), 3-(3-chloropropyl)-1H-indole-5-nitrile (1.17 g, 5.35 mmol), anhydrous sodium carbonate (2.83 g, 26.7 mmol) and sodium iodide (0.20 g, 1.33 mmol) were added to acetonitrile (50 mL). The mixture solution was heated to 90° C. and reacted for 36 hours. The crude product was further purified by a silica gel column chromatography (dichloromethane/methanol (v/v)=30/1) to give the title compound as a faint yellow solid (1.87 g, 86.3%).

MS (ESI, pos. ion) m/z: 487.90 [M+H]⁺;
¹H NMR (400 MHz, DMSO-d₆) δ (ppm): 11.38 (s, 1H), 8.82 (s, 2H), 8.10 (s, 1H), 7.57 (s, 2H), 7.50 (d, J=8.4 Hz, 1H), 7.40 (d, J=8.4 Hz, 1H), 7.35 (s, 1H), 3.84 (brs, 4H), 2.76 (t, J=7.1 Hz, 2H), 2.60 (s, 3H), 2.43 (brs, 4H), 2.36 (t, J=6.7 Hz, 2H), 1.91~1.75 (m, 2H);
HPLC: 99.61%.

Example 9 Synthesis of ethyl 2-(2-(4-(4-(5-cyano-1H-indol-3-yl)butyl)piperazin-1-yl)pyrimidin-5-yl)-4-methylthiazole-5-formate

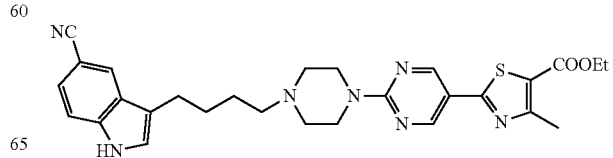

Step 1) Synthesis of ethyl 2-(2-(4-(Boc)piperazin-1-yl)pyrimidin-5-yl)-4-methylthiazole-5-formate The title compound of this step was prepared by the method described in Example 7, Step 1, namely, 2-(4-Boc-piperazin-1-yl)pyrimidine-5-boronic acid pinacol ester (1.50 g, 3.84 mmol), ethyl 2-bromo-4-methylthiazole-5-formate (1.15 g, 4.61 mmol), cesium carbonate (3.13 g, 9.60 mmol) and [1,1'-bis(diphenylphosphino)ferrocene]palladium dichloride (II) (141 mg, 0.19 mmol) were added to a mixed solvent of 2-methyltetrahydrofuran (15 mL) and water (3 mL), the mixture was heated to 100° C. and reacted overnight under $N_2$. The residue was further purified by a silica gel column chromatography (dichloromethane/methanol (v/v)=60/1) to give the title compound as a faint yellow solid (1.21 g, 72.6%).

MS (ESI, pos. ion) m/z: 434.25 $[M+H]^+$;

$^1$H NMR (600 MHz, DMSO-$d_6$) δ (ppm): 8.84 (s, 2H), 4.27 (q, J=7.1 Hz, 2H), 3.91-3.79 (m, 4H), 3.43 (dd, J=14.7, 10.3 Hz, 4H), 2.59 (s, 3H), 1.45 (s, 9H), 1.30 (t, J=7.1 Hz, 3H).

Step 2) Synthesis of ethyl 4-methyl-2-(2-(piperazin-1-yl)pyrimidin-5-yl)thiazole-5-formate dihydrochloride The title compound of this step was prepared by the method described in Example 1, Step 2, namely, ethyl 2-(2-(4-(Boc)piperazin-1-yl)pyrimidin-5-yl)-4-methylthiazole-5-formate (1.21 g, 2.79 mmol) and a solution of hydrogen chloride in ethyl acetate (8.0 mL, 3.2 mol/L) were added to dichloromethane (10 mL). Then the mixture was reacted for 4 hours at room temperature. The solvent was evaporated under reduced pressure to give the title compound as a faint yellow solid (1.13 g, 99.8%).

MS (ESI, pos. ion) m/z: 334.15 $[M+H]^+$.

Step 3) Synthesis of ethyl 2-(2-(4-(4-(5-cyano-1H-indol-3-yl)butyl)piperazin-1-yl)pyrimidin-5-yl)-4-methylthiazole-5-formate The title compound of this step was prepared by the method described in Example 1, Step 3, namely, ethyl 4-methyl-2-(2-(piperazin-1-yl)pyrimidin-5-yl)thiazole-5-formate dihydrochloride (500 mg, 1.23 mmol), 3-(4-chlorobutyl)-1H-indole-5-nitrile (344 mg, 1.48 mmol), anhydrous sodium carbonate (782 mg, 7.38 mmol) and sodium iodide (56 mg, 0.37 mmol) were added to acetonitrile (15 mL). The mixture solution was heated to 90° C. and reacted for 36 hours. The crude product was further purified by a silica gel column chromatography (dichloromethane/methanol (v/v)=50/1) to give the title compound as a faint yellow solid (492 mg, 75.6%).

MS (ESI, pos. ion) m/z: 530.30 $[M+H]^+$;

$^1$H NMR (600 MHz, DMSO-$d_6$) δ (ppm): 11.38 (s, 1H), 8.82 (s, 2H), 8.10 (s, 1H), 7.51 (d, J=8.3 Hz, 1H), 7.40 (d, J=8.3 Hz, 1H), 7.34 (s, 1H), 4.27 (q, J=7.1 Hz, 2H), 3.84 (brs, 4H), 2.75 (t, J=7.4 Hz, 2H), 2.62 (s, 3H), 2.40 (brs, 4H), 2.39 (t, J=7.1 Hz, 2H), 1.65 (dd, J=14.6, 7.4 Hz, 2H), 1.50 (d, J=6.8 Hz, 2H), 1.29 (t, J=7.0 Hz, 3H);

HPLC: 99.50%.

Example 10 Synthesis of ethyl 2-(2-(4-(3-(5-cyano-1H-indol-3-yl)propyl)piperazin-1-yl)pyrimidin-5-yl)-4-methylthiazole-5-formate

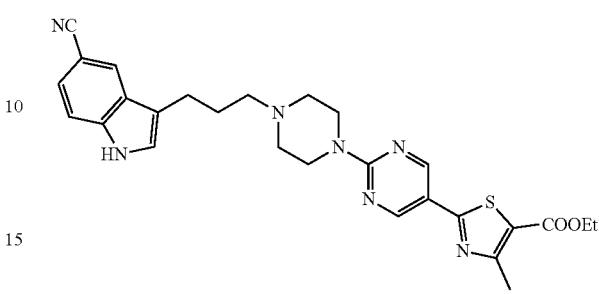

The title compound of this step was prepared by the method described in Example 1, Step 3, namely, ethyl 4-methyl-2-(2-(piperazin-1-yl)pyrimidin-5-yl)thiazole-5-formate dihydrochloride (500 mg, 1.23 mmol), 3-(3-chloropropyl)-1H-indole-5-nitrile (324 mg, 1.48 mmol), anhydrous sodium carbonate (782 mg, 7.38 mmol) and sodium iodide (56 mg, 0.37 mmol) were added to acetonitrile (15 mL). The mixture solution was heated to 90° C. and reacted for 36 hours. The crude product was purified by a silica gel column chromatography (dichloromethane/methanol (v/v)=50/1) to give the title compound as a faint yellow solid (523 mg, 82.5%).

MS (ESI, pos. ion) m/z: 516.25 $[M+H]^+$;

$^1$H NMR (400 MHz, DMSO-$d_6$) δ (ppm): 11.37 (s, 1H), 8.80 (s, 2H), 8.12 (s, 1H), 7.50 (d, J=8.4 Hz, 1H), 7.40 (d, J=8.3 Hz, 1H), 7.35 (s, 1H), 4.27 (q, J=7.2 Hz, 2H), 3.88 (brs, 4H), 2.77 (t, J=7.1 Hz, 2H), 2.62 (s, 3H), 2.41 (brs, 4H), 2.35 (t, J=6.7 Hz, 2H), 1.89~1.77 (m, 2H), 1.29 (t, J=7.0 Hz, 3H);

HPLC: 99.15%.

Example 11 Synthesis of 2-(2-(4-(4-(5-cyano-1H-indol-3-yl)butyl)piperazin-1-yl)pyrimidin-5-yl)-4-methyloxazole-5-carboxamide

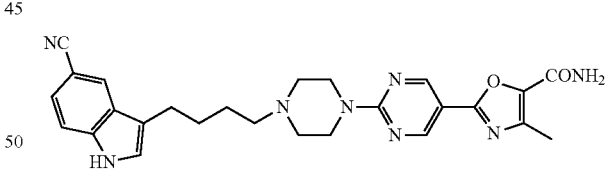

Step 1) Synthesis of t-butyl 4-(5-(5-carbamoyl-4-methyloxazole-2-yl)pyrimidin-2-yl)piperazine-1-formate The title compound of this step was prepared by the method described in Example 7, Step 1, namely, 2-(4-Boc-piperazin-1-yl)pyrimidine-5-boronic acid pinacol ester (1.50 g, 3.84 mmol), 2-bromo-4-methyloxazole-5-carboxamide (0.94 g, 4.61 mmol), cesium carbonate (3.13 g, 9.60 mmol) and [1,1'-bis(diphenylphosphino)ferrocene]palladium dichloride (II) (139 mg, 0.19 mmol) were added to a mixed solvent of 2-methyltetrahydrofuran (15 mL) and water (3 mL), the mixture was heated to 100° C. and reacted overnight under $N_2$. The crude product was further purified by a silica gel column chromatography (dichloromethane/methanol (v/v)=40/1) to give the title compound as a faint yellow solid (1.13 g, 75.5%).

MS (ESI, pos. ion) m/z: 389.30 [M+H]$^+$;

1H NMR (600 MHz, DMSO-d$_6$) δ (ppm): 8.88 (s, 2H), 7.58 (s, 2H), 3.85~3.75 (m, 4H), 3.43~3.33 (m, 4H), 2.58 (s, 3H), 1.44 (s, 9H).

Step 2) Synthesis of 4-methyl-2-(2-(piperazin-1-yl)pyrimidin-5-yl)oxazole-5-carboxamide dihydrochloride The title compound of this step was prepared by the method described in Example 1, Step 2, namely, t-butyl 4-(5-(5-carbamoyl-4-methyloxazol-2-yl)pyrimidin-2-yl)piperazine-1-Formate (1.13 g, 2.91 mmol) and a solution of hydrogen chloride in ethyl acetate (8.2 mL, 3.2 mol/L) were added to dichloromethane (10 mL). Then the mixture was reacted for 4 hours at room temperature. The solvent was evaporated under reduced pressure to give the title compound as a faint yellow solid (1.05 g, 99.5%).

MS (ESI, pos. ion) m/z: 289.25 [M+H]$^+$.

Step 3) Synthesis of 2-(2-(4-(4-(5-cyano-1H-indol-3-yl)butyl)piperazin-1-yl)pyrimidin-5-yl)-4-methyl-oxazole-5-formamide The title compound of this step was prepared by the method described in Example 1, Step 3, namely, 4-methyl-2-(2-(piperazin-1-yl)pyrimidin-5-yl)oxazole-5-carboxamide dihydrochloride (500 mg, 1.38 mmol), 3-(4-chlorobutyl)-1H-indole-5-nitrile (386 mg, 1.66 mmol), anhydrous sodium carbonate (878 mg, 8.28 mmol) and sodium iodide (63 mg, 0.42 mmol) were added to acetonitrile (15 mL). The mixture solution was heated to 90° C. and reacted for 36 hours. The crude product was further purified by a silica gel column chromatography (dichloromethane/methanol (v/v)=30/1) to give the title compound as a faint yellow solid (492 mg, 73.6%).

MS (ESI, pos. ion) m/z: 485.25 [M+H]$^+$;

$^1$H NMR (600 MHz, DMSO-d$_6$) δ (ppm): 11.37 (s, 1H), 8.85 (s, 2H), 8.15 (s, 1H), 7.60 (s, 2H), 7.50 (d, J=8.4 Hz, 1H), 7.41 (dd, J=8.4, 1.4 Hz, 1H), 7.35 (d, J=1.5 Hz, 1H), 3.85 (brs, 4H), 2.76 (t, J=7.3 Hz, 2H), 2.61 (s, 3H), 2.45 (brs, 4H), 2.37 (t, J=7.1 Hz, 2H), 1.95~1.81 (m, 2H), 1.56~1.50 (m, 2H);

HPLC: 98.95%.

Example 12 Synthesis of 2-(2-(4-(3-(5-cyano-1H-indol-3-yl)propyl)piperazin-1-yl)pyrimidin-5-yl)-4-methyloxazole-5-carboxamide

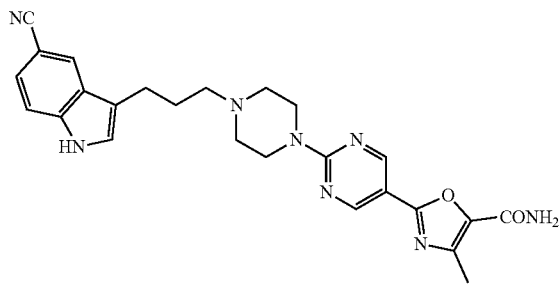 [SMILES: Cc1nc(-c2cnc(N3CCN(CCCc4c[nH]c5ccc(C#N)cc45)CC3)nc2)oc1C(N)=O]

The title compound of this step was prepared by the method described in Example 1, Step 3, namely, 4-methyl-2-(2-(piperazin-1-yl)pyrimidin-5-yl)oxazole-5-carboxamide dihydrochloride (500 mg, 1.38 mmol), 3-(3-chloropropyl)-1H-indole-5-nitrile (363 mg, 1.66 mmol), anhydrous sodium carbonate (878 mg, 8.28 mmol) and sodium iodide (63 mg, 0.42 mmol) were added to acetonitrile (15 mL). The mixture solution was heated to 90° C. and reacted for 36 hours. The residue was further purified by a silica gel column chromatography (dichloromethane/methanol (v/v)=30/1) to give the title compound as a faint yellow solid (488 mg, 75.2%).

MS (ESI, pos. ion) m/z: 471.25 [M+H]$^+$;

$^1$H NMR (600 MHz, DMSO-d$_6$) δ (ppm): 11.35 (s, 1H), 8.86 (s, 2H), 8.13 (s, 1H), 7.62 (s, 2H), 7.50 (d, J=8.3 Hz, 1H), 7.40 (dd, J=8.3, 1.3 Hz, 1H), 7.37 (d, J=1.5 Hz, 1H), 3.86 (brs, 4H), 2.73 (t, J=7.3 Hz, 2H), 2.61 (s, 3H), 2.42 (brs, 4H), 2.36 (t, J=7.1 Hz, 2H), 1.92~1.79 (m, 2H);

HPLC: 99.66%.

Example 13 Synthesis of ethyl 2-(2-(4-(4-(5-cyano-1H-indol-3-yl)butyl)piperazin-1-yl)pyrimidin-5-yl)-4-methylthiazole-5-formate

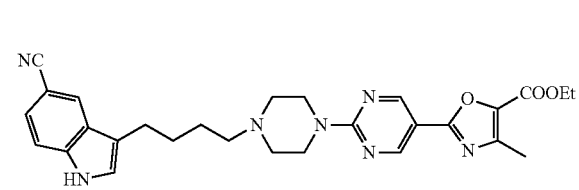 [SMILES: CCOC(=O)c1oc(-c2cnc(N3CCN(CCCCc4c[nH]c5ccc(C#N)cc45)CC3)nc2)nc1C]

Step 1 Synthesis of ethyl 2-(2-(4-(Boc)piperazin-1-yl)pyrimidin-5-yl)-4-methylthiazole-5-formate The title compound of this step was prepared by the method described in Example 7, Step 1, namely, 2-(4-Boc-piperazin-1-yl)pyrimidine-5-boronic acid pinacol ester (1.50 g, 3.84 mmol), ethyl 2-bromo-4-methyloxazole-5-formate (1.08 g, 4.61 mmol), cesium carbonate (3.13 g, 9.60 mmol) and [1,1'-bis(diphenylphosphino)ferrocene]palladium dichloride (II) (141 mg, 0.19 mmol) were added to a mixed solvent of 2-methyltetrahydrofuran (15 mL) and water (3 mL), the mixture was heated to 100° C. and reacted overnight under N$_2$. The residue was further purified by a silica gel column chromatography (dichloromethane/methanol (v/v)=60/1) to give the title compound as a faint yellow solid (1.03 g, 70.3%).

MS (ESI, pos. ion) m/z: 418.30 [M+H]$^+$;

$^1$H NMR (600 MHz, DMSO-d$_6$) δ (ppm): 8.88 (s, 2H), 4.26 (q, J=7.1 Hz, 2H), 3.91~3.83 (m, 4H), 3.45~3.31 (m, 4H), 2.59 (s, 3H), 1.44 (s, 9H), 1.29 (t, J=7.1 Hz, 3H).

Step 2) Synthesis of ethyl 4-methyl-2-(2-(piperazin-1-yl)pyrimidin-5-yl)oxazole-5-formate dihydrochloride The title compound of this step was prepared by the method described in Example 1, Step 2, namely, ethyl 2-(2-(4-(Boc)piperazin-1-yl)pyrimidin-5-yl)-4-methyloxazole-5-formate (1.03 g, 2.47 mmol) and a solution of hydrogen chloride in ethyl acetate (7.0 mL, 3.2 mol/L) were added to dichloromethane (10 mL). Then the mixture was reacted for 4 hours at room temperature. The solvent was evaporated under reduced pressure to give the title compound as a faint yellow solid (0.96 g, 99.8%).

MS (ESI, pos. ion) m/z: 318.15 [M+H]$^+$.

Step 3) Synthesis of ethyl 2-(2-(4-(4-(5-cyano-1H-indol-3-yl)butyl)piperazin-1-yl)pyrimidin-5-yl)-4-methyloxazole-5-formate The title compound of this step was prepared by the method described in Example 1, Step 3, namely, ethyl 4-methyl-2-(2-(piperazin-1-yl)pyrimidin-5-yl)oxazole-5-formate dihydrochloride (450 mg, 1.15 mmol), 3-(4-chlorobutyl)-1H-indole-5-nitrile (321 mg, 1.38 mmol), anhydrous sodium carbonate (731 mg, 6.90 mmol) and sodium iodide (51 mg, 0.34 mmol) were added to acetonitrile (15 mL). The mixture solution was heated to 90° C. and reacted for 36 hours. The crude product was further purified by a silica gel column chromatography (dichloromethane/methanol (v/v)=30/1) to give the title compound as a faint yellow solid (444 mg, 75.1%).

MS (ESI, pos. ion) m/z: 514.30 [M+H]$^+$.

$^1$H NMR (600 MHz, DMSO-d$_6$) δ (ppm): 11.34 (s, 1H), 8.83 (s, 2H), 8.12 (s, 1H), 7.50 (d, J=8.3 Hz, 1H), 7.42 (dd, J=8.3, 1.3 Hz, 1H), 7.35 (s, 1H), 4.27 (q, J=7.1 Hz, 2H), 3.86 (brs, 4H), 2.76 (t, J=7.3 Hz, 2H), 2.61 (s, 3H), 2.42 (brs, 4H), 2.39 (t, J=7.1 Hz, 2H), 1.93~1.83 (m, 2H), 1.55~1.50 (m, 2H), 1.30 (t, J=7.1 Hz, 3H);

HPLC: 99.26%.

Example 14 Synthesis of ethyl 2-(2-(4-(3-(5-cyano-1H-indol-3-yl)propyl)piperazin-1-yl)pyrimidin-5-yl)-4-methylthiazole-5-formate

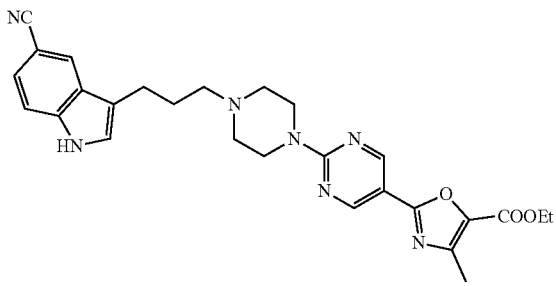 [SMILES: CCOC(=O)c1oc(-c2cnc(N3CCN(CCCc4c[nH]c5ccc(C#N)cc45)CC3)nc2)nc1C]

The title compound of this step was prepared by the method described in Example 1, Step 3, namely, ethyl 4-methyl-2-(2-(piperazin-1-yl)pyrimidin-5-yl)oxazole-5-formate dihydrochloride (450 mg, 1.15 mmol), 3-(3-chloropropyl)-1H-indole-5-nitrile (302 mg, 1.38 mmol), anhydrous sodium carbonate (731 mg, 6.90 mmol) and sodium iodide (51 mg, 0.34 mmol) were added to acetonitrile (15 mL). The mixture solution was heated to 90° C. and reacted for 36 hours. The crude product was further purified by a silica gel column chromatography (dichloromethane/methanol (v/v)=30/1) to give the title compound as a faint yellow solid (450 mg, 78.3%).

MS (ESI, pos. ion) m/z: 500.30 [M+H]$^+$;

$^1$H NMR (600 MHz, DMSO-d$_6$) δ (ppm): 11.38 (s, 1H), 8.82 (s, 2H), 8.10 (s, 1H), 7.51 (d, J=8.3 Hz, 1H), 7.45 (d, J=8.3, 1H), 7.36 (s, 1H), 4.26 (q, J=7.1 Hz, 2H), 3.88 (brs, 4H), 2.77 (t, J=7.3 Hz, 2H), 2.60 (s, 3H), 2.39 (brs, 4H), 2.38 (t, J=7.1 Hz, 2H), 1.81~1.73 (m, 2H), 1.28 (t, J=7.1 Hz, 3H);

HPLC: 99.05%.

Biological Assay

Example A: Evaluation of the Affinity of the Compound of the Invention to Humanized 5-HT Transporter Transfected by CHQ Cells Test method To a mixture of cell membrane homogenate protein (12 μg), 2 nM [$^3$H] imipramine, buffer (50 mM Tris-HCl (pH 7.4), 120 mM NaCl, 5 mM KCl, and 0.1% BSA) was added test compound or not under a condition of 22° C. The reaction mixture was incubated for 60 minutes.

To the mixture of the above condition was added 10 μM imipramine to measure the non-specific binding value.

The incubated samples were quickly filtered through a glass fiber membrane (GF/B, Packard) impregnated with 0.3% PEI by a 96-well cell collector (Unifilter, Packard) under vacuum, and repeatedly rinsed with cold 50 mM Tris-HCl and 150 mM NaCl for several times. The filter was dried and the residual radioactivity was calculated in a scintillation counter (Topcount, Packard) by using scintillation fluid (Microscint 0, Packard). The experimental results were expressed as a percentage of inhibition of specific binding of radioligand to the control group.

The standard reference compound was imipramine. The competitive curve was obtained by a series of concentration experiments and the IC$_{50}$ was calculated. The results were shown in Table A. Table A showed the experimental results of the affinity of the compound of the invention to humanized 5-HT transporter (SERT).

TABLE A

The testing result of the affinity of the compound of the invention to humanized 5-HT transporter (SERT).

| Example | IC$_{50}$ (nM) | Example | IC$_{50}$ (nM) |
| --- | --- | --- | --- |
| Example 1 | 0.68 | Example 6 | 0.23 |
| Example 2 | 0.45 | Example 7 | 0.77 |
| Example 3 | 0.79 | Example 8 | 0.33 |
| Example 4 | 0.81 | Example 9 | 0.45 |
| Example 5 | 0.66 | Example 10 | 0.13 |

The experimental results show that the compound of the present invention has a strong affinity to human 5-HT transporter (SERT).

Example B: h5-HT$_{1A}$ Binding Affinity Test

Test method

To a mixture of human HEK-293 cell membrane homogenate (36 μg protein), 0.3 nM [$^3$H]8-OH-DPAT (Perkin-Elmer) and buffer (50 mM Tris-HCl (pH 7.4), 10 mM MgSO$_4$, 0.5 mM EDTA, 2 μg/ml aprotinine) was added test compound or not under a condition of 22° C. The reaction mixture was incubated for 60 minutes.

The standard reference compound was 8-OH-DPAT. To a mixture of the above condition was added 10 μM 8-OH-DPAT to measure the non-specific binding value. A competitive curve was obtained by testing the data of a series of concentrations of 8-OH-DPAT in different experiments.

The incubated samples were quickly filtered through a glass fiber membrane (GF/B, Packard) impregnated with 0.3% PEI by a 96-well cell collector (Unifilter, Packard) under vacuum, and repeatedly rinsed with cold 50 mM Tris-HCl for several times. The filter was dried and the residual radioactivity was calculated in a scintillation counter (Topcount, Packard) by using scintillation fluid (Microscint 0, Packard). The experimental results were expressed as a percentage of inhibition of specific binding of radioligand to the control group.

Data Analysis

The binding assay of [$^3$H]8-OH-DPAT (0.3 nM) to the 5-HT$_{1A}$ receptor in human HEK-293 cells was performed by a scintillation proximity assay of the membrane. The test compound needed to be tested at least three times at a concentration exceeding 6 log, and the data was subjected to nonlinear regression analysis by a Hill equation curve to obtain an IC$_{50}$ value, which was then calculated by the ChengPrusoff equation to obtain a Ki value. The results were shown in Table B. Table B showed the experimental results of the affinity of the compound of the invention to 5-HT$_{1A}$ receptor.

TABLE B

The testing result of the affinity of the compound of the invention to 5-HT$_{1A}$ receptor.

| Example | K$_i$ (nM) | Example | K$_i$ (nM) |
|---------|-----------|---------|-----------|
| Example 1 | 2.13 | Example 6 | 1.1 |
| Example 2 | 4.31 | Example 7 | 1.01 |
| Example 3 | 2.19 | Example 8 | 2.14 |
| Example 4 | 4.13 | Example 9 | 0.99 |
| Example 5 | 0.53 | Example 10 | 2.16 |

The experimental results show that the compound of the present invention has a strong affinity to 5-HT$_{1A}$ receptor.

Example C: Pharmacokinetic Evaluation of Rats, Dogs and Monkeys after Intravenous or Intragastric Administration of the Compound of the Invention Pharmacokinetics of the compound of the invention in rats, dogs and monkeys were studied and evaluated. Animal information was shown in Table 1.

TABLE 1 information table of the animals in this experiment

| Species | Grade | Gender | Weight | Age | Source |
|---------|-------|--------|--------|-----|--------|
| SD rat | SPF | Male | 170–250 g | 6-9 weeks | Hunan Slake Laboratory Animal Co., Ltd. |
| Beagle dog | Clean facility | Male | 8~10 kg | 6-7 weeks | Hunan Slake Laboratory Animal Co., Ltd. |
| Cynomolgus monkey | SPF | Male | 3~5 kg | 4 years | Guangdong Landau Biotechnology Co., Ltd. |

Test method

The compound was administered to the tested animals in the form of 5% DMSO+5% Kolliphor HS15+2% (2% HCl)+88% Saline saline solution or 10% DMSO+10% Kolliphor HS15+80% normal saline solution. For the intravenous administration group, the dose was 1 mg/kg, and then the venous blood (0.3 mL) was taken at a time of 0, 0.083, 0.25, 0.5, 1.0, 2.0, 5.0, 7.0, and 24 hours after administration, and centrifuged at 3,000 or 4,000 rpm for 10 minutes. The plasma solution was collected and stored at −20° C. or −70° C. For the intragastric administration group, the dose was 2.5 mg/kg, and then the venous blood (0.3 mL) was taken at a time of 0, 0.083, 0.25, 0.5, 1.0, 2.0, 5.0, 7.0, and 24 hours after administration, and centrifuged at 3,000 or 4,000 rpm for 10 minutes. The plasma solution was collected and stored at −20° C. or −70° C.

The plasma solutions obtained from each of the above groups were subjected to LC/MS/MS analysis.

LC/MS/MS Analysis Method

The LC/MS/MS system for analysis included the Agilent 1200 Series vacuum degasser, binary pump, orifice autosampler, thermostatic column oven, and Agilent G6430A triple quadrupole mass spectrometer with electrospray ionization (ESI) source. Quantitative analysis was performed in MRM mode, wherein the source parameters of MRM conversion were shown in Table 2:

TABLE 2

| Ion source voltage | 3500 V |
|---|---|
| The temperature of dry gas | 350° C. |
| Atomizing gas | 40 psi |
| The flow rate of dry gas | 9 L/min |

Analysis was performed using a waters XBridge C18 (2.1×50 mm) column. The column was 3.5 μM and injection volume was 5 μL. The analytical conditions were as follows: mobile phase A: water+2 mM ammonium formate+0.1% formic acid mobile phase B: methanol+2 mM ammonium formate+0.1% formic acid. The flow rate was 0.4 mL/min. The gradient of mobile phase was shown in Table 3.

TABLE 3

| Time | The gradient of mobile phase B |
|------|-------------------------------|
| 0.9 min | 5%. |
| 1.6 min | 85%. |
| 2.7 min | 95%. |

TABLE 3-continued

| Time | The gradient of mobile phase B |
|------|-------------------------------|
| 2.8 min | 5%. |
| 4.0 min | Termination |

The results were shown in Table C. Table C showed the results of pharmacokinetic experiments of the compound of the invention in rats.

TABLE C

The results of pharmacokinetic experiments of the compound of the invention in rats.

| Compound number | Route of administration | dosage (mg/kg) | $T_{max}$ (h) | $C_{max}$ (ng/ml) | $AUC_{last}$ (h * ng/mL) | $AUC_{INF}$ (h * ng/mL) | $T_{1/2}$ (h) | Cl (mL/min/kg) | $V_{ss}$ (L/kg) | F (%) |
|---|---|---|---|---|---|---|---|---|---|---|
| Example 8 | iv | 1 | 0.083 | 1000 | 1740 | 1820 | 1.72 | 9.22 | 1.3 | N/A |
|  | po | 2.5 | 1 | 590 | 1740 | 1550 | 1.58 | N/A | N/A | 39.8 |

Note:
iv is intravenous administration;
po is oral administration;
N/A means "none".

The experimental results show that the compound of the present invention has good pharmacokinetic properties in rats.

Example D: Evaluation of the Effect of the Compound of the Invention on the Stationary Time in a Forced Swimming Test of Mice The effects of the compound of the invention on the stationary time in a forced swimming test of mice were evaluated in the present invention. Animal information was shown in Table 4.

TABLE 4

Information table of the test animals in this experiment

| Species | Grade | Gender | Weight | age | Source |
|---|---|---|---|---|---|
| C57BL/ 6 mice | SPF | Male | 21.1 ± 0.1 g | 8-10 weeks | Shanghai Lingchang Experimental Animal Co., Ltd. |

Test method

Animals (C57BL/6 mice) were fed in the animal house barrier system one week earlier to adapt to the rearing environment of animal house. Three days before the trial, each animal was touched 2-3 minutes/day. On the day of the experiment, the animals were transferred to the operating room 60 minutes in advance, and were randomly divided into a vehicle group (20% HP-β-CD+80% $H_2O$), a 40 mg/kg dose group of hydrochloride of Desipramine as the standard reference compound, 1, 3, 10 mg/kg dose groups of the phosphate of the test compound, a 3 mg/kg dose group of the hydrochloride of Vilazone, and a 3 mg/kg dose group of hydrochloride of compound A, a total of 7 groups, the number of animals in each group was 15-16. The vehicle, the standard reference compound of Desipramine, the test compound, Vilazodone or Compound A were intraperitoneally injected 30 minutes before the test. The mice were placed in the experimental apparatus during the test. The experimental apparatus was a cylindrical organic transparent glass tank (23 cm high and 12 cm in diameter). The water level was 8 cm from the bottom and the water temperature was 22±2° C. The length of each test was 6 minutes. There was one animal in each sink, recorded by an Ethovision software and a double-blind manual counting analysis. The stationary time of the last 4 minutes of the animal was recorded. All the experimental results were expressed as mean ±standard error (Mean ±SEM). Prism 6.0 statistical software was used to test and analyze the results. The significance of the difference was P<0.05, and P<0.01 was very significant.

The results were shown in Table D. Table D showed the results of the experiment of the compound of the invention about the stationary time of the last 4 minutes in a forced swimming test of mice.

TABLE D

The results of the experiment of the compound of the invention about the stationary time of the last 4 minutes in a forced swimming test of mice.

| Drug group | dosage (mg/kg) | Stationary time (seconds) |
|---|---|---|
| Solvent group (20% HP-β-CD + 80% $H_2O$) | N/A | 120.4 ± 16.5 |
|  | 3 | 75.1 ± 13.3* |

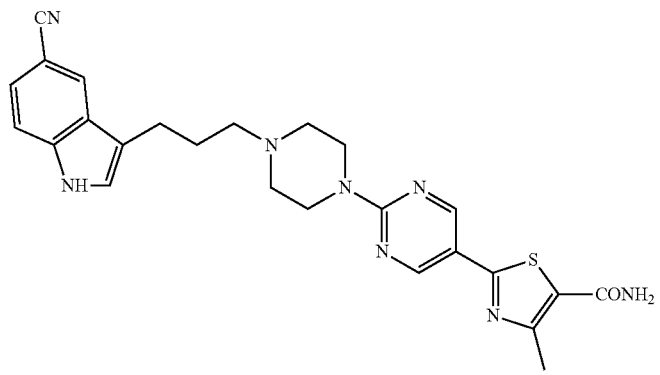

Example 8

TABLE D-continued

The results of the experiment of the compound of the invention about the
stationary time of the last 4 minutes in a forced swimming test of mice.

| Drug group | dosage (mg/kg) | Stationary time (seconds) |
|---|---|---|
| 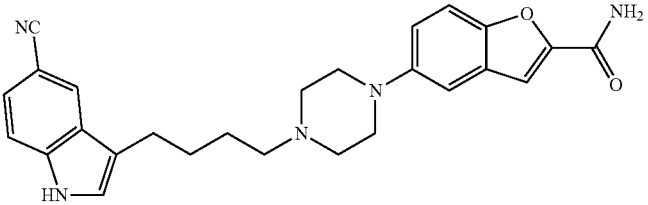 Vilazodone | 3 | 107.8 ± 16.1 |
| Compound A Error! Objects cannot be created from editing field codes. | 3 | 108.9 ± 11.7 |

Note:
Compared with the vehicle group: *, P < 0.05.
The synthesis method of Compound A refers to the synthesis method of Example 2 in Patent application WO 2016192657 A1.

The results of the experiment show that the compound of the present invention can reduce the stationary time of mice compared with the vehicle group, and the difference is significant (P<0.05); both Vilazodone and Compound A can slightly reduce the stationary time of mice, but there is no significant difference. Therefore, the above experimental results show that the compound of the present invention has better antidepressant activity and is superior to Velazodone and Compound A at the same dose.

Example E: Evaluation of the Effect of the Compound of the Invention on the Stationary Time in Tail Suspension Test of Mice Test method DBA/2J mice were acclimatized in the animal house for at least 7 days. On the day of the experiment, the animals were transferred to the operating room 1 hour in advance, and were randomly divided into a vehicle group (20% HP-β-CD+80% $H_2O$), a 60 mg/kg dose group of hydrochloride of Vilazodone, 30, 60, 120 mg/kg dose groups of the phosphate of the test compound, a 60 mg/kg dose group of hydrochloride of compound A, a total of 6 groups. At 24 h, 5 h and 1 h before the experiment, the vehicle group, Vilazodone, test compound or compound A were intraperitoneally injected for 3 times. The animals were suspended on the tail suspension system test box and fixed on the tail hook of the test box with adhesive tape about 2 cm from the tail tip. The test duration was 6 minutes and the stationary time of the mice was recorded over the 6 minutes. All the experimental results were expressed as mean ±standard error (Mean ±SEM). Prism 6.0 statistical software was used to test and analyze the results. The significance of the difference was P<0.05, and P<0.01 was very significant.

The experimental results show that the compound of the present invention can reduce the stationary time of the mice, and therefore the compound of the present invention has better antidepressant activity.

Example F: Analysis of the Inhibitory Effect of the Compound of the Invention on [$^3$H]5-HT Uptake in Synaptosomes of Rats Test method To a mixture of buffer (106.2 mM NaCl, 4.5 mM KCl, 2.25 mM $MgSO_4$, 1.08 mM $NaH_2PO_4$, 22.5 mM $NaHCO_3$, 9.9 mM glucose, 9 μM EGTA and 45 μM ascorbic acid (pH 7.4)), the synaptosome (150 μg) and 0.1 μCi [$^3$H]5-hydroxytryptamine were added test compound or positive drug or negative control. The mixture was incubated for 15 min.

As a standard positive compound for inhibiting 5-hydroxytryptamine uptake, imipramine of 10 μM was added to the same mixed system as above to block 5-hydroxytryptamine uptake and incubated at 4° C. for 15 minutes to determine the basal control activity value. The inhibitory values of different concentrations of imipramine on brain synaptosomes of rats were tested to produce inhibition curves through experiments.

The incubated samples were quickly filtered through a glass fiber membrane (GF/B, Packard) by a 96-well cell collector (Unifilter, Packard) under vacuum, and rinsed with cold incubation buffer for twice to eliminate free [$^3$H]5-hydroxytryptamine. The filter was dried and the residual radioactivity was calculated in a scintillation counter (Topcount, Packard) by using scintillation fluid (Microscint 0, Packard). The experimental results were expressed as a percentage of inhibition of 5-hydroxytryptamine uptake to the control group.

Data Analysis

The inhibition of SERT transporter in synaptosomes of rats was measured by the concentration of [$^3$H]5-HT. The test compound needed to be tested at least two times at a concentration exceeding 6 log, and the data was subjected to nonlinear regression analysis by a Hill equation curve to obtain an $IC_{50}$ value.

The experimental results show that the compounds provided in the examples of the present invention have good inhibitory activity against 5-HT reuptake.

In the description of the present specification, the reference terms "one embodiment", "some embodiments", "an example", "a specific example" or "some examples", and the like means that a particular feature, structure, material, or characteristic described in connection with the embodiment or example is included in at least one embodiment or example of the present disclosure. In the present specification, the schematic representation of the above terms is not necessarily directed to the same embodiment or example. Furthermore, the particular features, structures, materials, or characteristics may be combined in any suitable manner in one or more embodiments or examples. In addition, those skilled in the art can integrate and combine different embodiments, examples or the features of them as long as they are not contradictory to one another.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

The invention claimed is:

1. A compound having Formula (I) or a stereoisomer, a geometric isomer, a tautomer, an N-oxide, a hydrate, a solvate, or a pharmaceutically acceptable salt thereof,

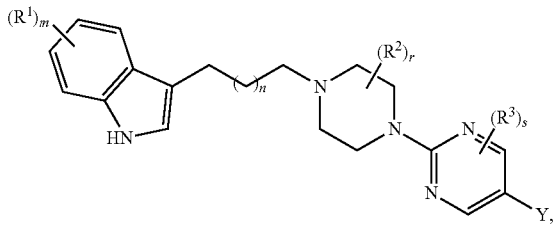

(I)

wherein

Y is 5-6 membered heteroaryl, wherein optionally the 5-6 membered heteroaryl is independently substituted with one or more $R^x$;

each $R^x$ is independently H, D, F, Cl, Br, I, nitro, cyano, —$NR^aR^b$, —$OR^c$, —$SR^c$, —$C(=O)R^d$, —$C(=O)OR^c$, —$C(=O)NR^aR^b$, —$OC(=O)R^d$, —$N(R^a)C(=O)R^d$, —$S(=O)R^d$, —$S(=O)_2R^d$, —$S(=O)_2OR^c$, —$S(=O)_2NR^aR^b$, —$N(R^a)S(=O)_2R^d$, —$N(R^a)C(=O)OR^c$, —$N(R^a)C(=O)NR^aR^b$, $C_1$-$C_6$ alkyl, $C_2$-$C_6$ alkenyl, $C_2$-$C_6$ alkynyl, $C_1$-$C_6$ haloalkyl, $C_3$-$C_{10}$ cycloalkyl, ($C_3$-$C_{10}$ cycloalkyl)-($C_1$-$C_6$ alkylene)-, 3-10 membered heterocyclyl, (3-10 membered heterocyclyl)-($C_1$-$C_6$ alkylene)-, $C_6$-$C_{10}$ aryl, ($C_6$-$C_{10}$ aryl)-($C_1$-$C_6$ alkylene)-, 5-10 membered heteroaryl or (5-10 membered heteroaryl)-($C_1$-$C_6$ alkylene);

each $R^1$ is independently H, D, F, Cl, Br, I, nitro, cyano, amino, hydroxy, sulfydryl, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, ($C_1$-$C_6$ alkoxy)-($C_1$-$C_4$ alkylene)-, $C_1$-$C_6$ alkylamino, ($C_1$-$C_6$ alkylamino)-($C_1$-$C_4$ alkylene)-, $C_1$-$C_6$ alkylthio or ($C_1$-$C_6$ alkylthio)-($C_1$-$C_4$ alkylene)-;

each $R^2$ is independently H, D, F, Cl, Br, I, $C_1$-$C_6$ alkyl, $C_1$-$C_6$ haloalkyl, —$NR^aR^b$, —$OR^c$, —$C(=O)R^d$, —$C(=O)OR^c$, —$C(=O)NR^aR^b$ or ($C_6$-$C_{10}$ aryl)-($C_1$-$C_6$ alkylene)-, or two R of adjacent carbon atoms, together with the carbon atoms they are attached to, form a $C_3$-$C_6$ carbocycle, a benzene ring, a 3-7 membered heterocyclyl ring or a 5-6 membered heteroaryl ring; or two $R^2$ of the same carbon atom, together with the carbon atom they are attached to together, form a $C_3$-$C_6$ carbocycle or a 3-7 membered heterocyclyl ring;

each $R^3$ is independently H, D, F, Cl, Br, I, nitro, cyano, amino, hydroxy, sulfydryl, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, ($C_1$-$C_6$ alkoxy)-($C_1$-$C_4$ alkylene)-, $C_1$-$C_6$ alkylamino, ($C_1$-$C_6$ alkylamino)-($C_1$-$C_4$ alkylene)-, $C_1$-$C_6$ alkylthio or ($C_1$-$C_6$ alkylthio)-($C_1$-$C_4$ alkylene)-;

each $R^a$ and $R^b$ is independently H, $C_1$-$C_6$ alkyl, $C_3$-$C_6$ alkenyl, $C_3$-$C_6$ alkynyl, $C_1$-$C_6$ haloalkyl, $C_3$-$C_6$ cycloalkyl, ($C_3$-$C_6$ cycloalkyl)-($C_1$-$C_4$ alkylene)-, 3-7 membered heterocyclyl, (3-7 membered heterocyclyl)-($C_1$-$C_4$ alkylene)-, phenyl, phenyl-($C_1$-$C_4$ alkylene)-, 5-6 membered heteroaryl and (5-6 membered heteroaryl)-($C_1$-$C_4$ alkylene)-, or $R^a$ and $R^b$ together with the nitrogen atom they are attached to together, form a 3-7 membered heterocyclyl ring;

each $R^c$ and $R^d$ is independently H, $C_1$-$C_6$ alkyl, $C_2$-$C_6$ alkenyl, $C_2$-$C_6$ alkynyl, $C_1$-$C_6$ haloalkyl, $C_3$-$C_6$ cycloalkyl, ($C_3$-$C_6$ cycloalkyl)-($C_1$-$C_4$ alkylene)-, 3-7 membered heterocyclyl, (3-7 membered heterocyclyl)-($C_1$-$C_4$ alkylene)-, phenyl, phenyl-($C_1$-$C_4$ alkylene)-, 5-6 membered heteroaryl or (5-6 membered heteroaryl)-($C_1$-$C_4$ alkylene)-;

m is 0, 1, 2, 3 or 4;

n is 0, 1, 2, 3, or 4;

r is 0, 1, 2, 3, 4, 5 or 6; and s is 0, 1, or 2.

2. The compound of claim 1, wherein Y is one of the substructures shown by Formulae (Y-1) to (Y-15):

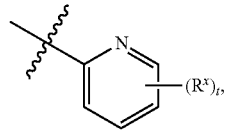

(Y-1)

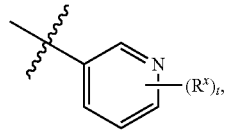

(Y-2)

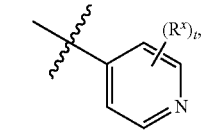

(Y-3)

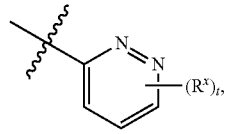

(Y-4)

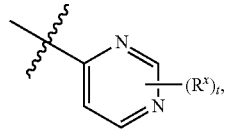

(Y-5)

-continued

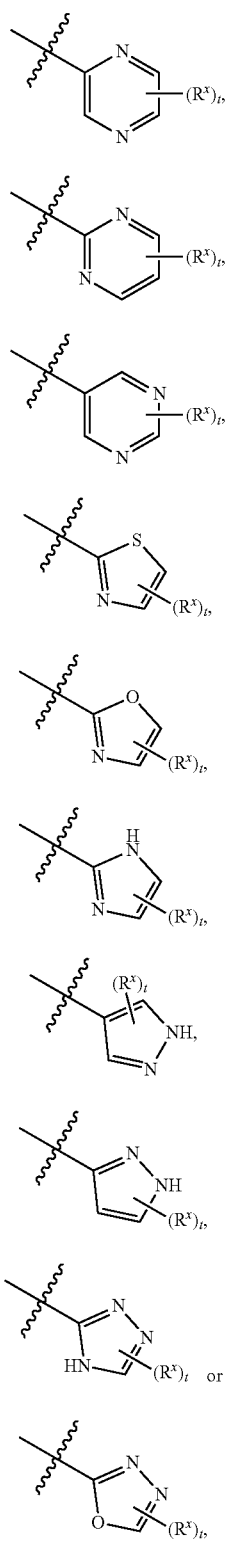

wherein each t is independently 1, 2, 3 or 4.

3. The compound of claim 1 having formula (VI), (VII), (VIII) or (IX) or a stereoisomer, a geometric isomer, a tautomer, an N-oxide, a hydrate, a solvate, or a pharmaceutically acceptable salt thereof,

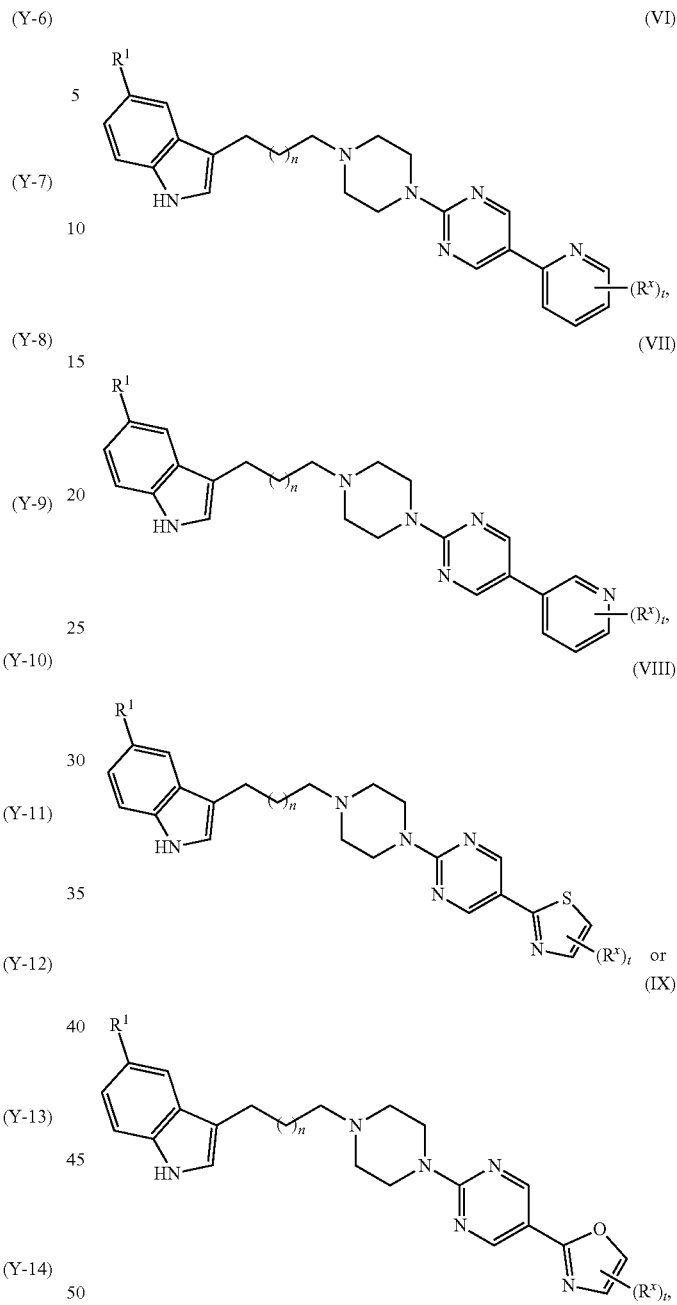

wherein each t is independently 1, 2, 3 or 4.

4. The compound of claim 1, wherein each $R^1$ is independently H, D, F, Cl, Br, I, cyano, nitro, amino, —NMe$_2$, hydroxy, —OMe, —OEt, —O(i-Pr), —O(t-Bu), methyl, ethyl, -(n-Pr), -(i-Pr), -(t-Bu) or —CF$_3$.

5. The compound of claim 1, wherein each $R^2$ is independently H, D, F, Cl, Br, I, amino, hydroxy, methyl, ethyl, -(n-Pr), -(i-Pr), -(t-Bu) or —CF$_3$, —OMe, —OEt, —O(i-Pr) or —O(t-Bu).

6. The compound of claim 1, wherein each $R^3$ is independently H, D, F, Cl, Br, I, cyano, nitro, amino, —NMe$_2$, hydroxy, —OMe, —OEt, —O(i-Pr), —O(t-Bu), methyl, ethyl, -(n-Pr), -(i-Pr), -(t-Bu) or —CF$_3$.

7. The compound of claim 1, wherein each $R^x$ is independently H, D, F, Cl, Br, I, cyano, nitro, amino, —NMe$_2$, —NHEt, —NEt$_2$, hydroxy, —OMe, —OEt, —O(n-Pr), —O(i-Pr), —O(t-Bu), methyl, ethyl, -(n-Pr), -(i-Pr), -(t-Bu), —CF$_3$, —CH$_2$CH$_2$C$_1$, —OCHF$_2$, —OCF$_3$, —OCH$_2$CF$_3$, —OCF$_2$CHF$_2$, —OCHFCF$_3$, —OCF$_2$CF$_3$, —OCF$_2$CH$_2$CH$_3$, —OCF$_2$CH$_2$CF$_3$, —OCF$_2$CH$_2$CHF$_2$, —OCH$_2$CHFCH$_3$, —OCH$_2$CF$_2$CH$_3$, —OCH$_2$CF$_2$CF$_3$, —OCH$_2$CF$_2$CHF$_2$, —CONH$_2$, —CONHMe, —CONMe$_2$, —C(=O)OMe, —C(=O)OEt, —NHC(=O)H, —NHC(=O)CH$_3$, —NHC(=O)OMe or phenyl.

8. The compound of claim 1, each R$^a$ and R$^b$ is independently H, Q-C$_4$ alkyl, C$_3$-C$_4$ alkenyl, C$_3$-C$_4$ alkynyl, C$_1$-C$_4$ haloalkyl, C$_5$-C$_6$ cycloalkyl, (C$_5$-C$_6$ cycloalkyl)-(C$_1$-C$_4$ alkylene)-, 5-7 membered heterocyclyl, (5-7 membered heterocyclyl)-(C$_1$-C$_4$ alkylene)-, phenyl, phenyl-(C$_1$-C$_4$ alkylene)-, 5-6 membered heteroaryl and (5-6 membered heteroaryl)-(C$_1$-C$_4$ alkylene)-, or R$^a$ and R$^b$, together with the nitrogen atom they are attached to together, form a 5-7 membered heterocyclyl ring; and each R$^c$ and R$^d$ is independently H, C$_1$-C$_4$ alkyl, C$_2$-C$_4$ alkenyl, C$_2$-C$_4$ alkynyl, C$_1$-C$_4$ haloalkyl, C$_5$-C$_6$ cycloalkyl, (C$_5$-C$_6$ cycloalkyl)-(C$_1$-C$_4$ alkylene)-, 5-7 membered heterocyclyl, (5-7 membered heterocyclyl)-(C$_1$-C$_4$ alkylene)-, phenyl, phenyl-(C$_1$-C$_4$ alkylene)-, 5-6 membered heteroaryl or (5-6 membered heteroaryl)-(C$_1$-C$_4$ alkylene)-.

9. The compound of claim 1, each R$^a$ and R$^b$ is independently H, methyl, ethyl, -(n-Pr), -(i-Pr), -(t-Bu), —CHF$_2$, —CF$_3$, —CH$_2$CF$_3$, —CF$_2$CHF$_2$, —CHFCF$_3$, —CF$_2$CF$_3$, —CF$_2$CH$_2$CH$_3$, —CF$_2$CH$_2$CF$_3$, —CF$_2$CH$_2$CHF$_2$, —CH$_2$CHFCH$_3$, —CH$_2$CF$_2$CH$_3$, —CH$_2$CF$_2$CF$_3$, —CH$_2$CF$_2$CHF$_2$, —CH$_2$CH$_2$Cl, cyclopentyl, pyrrolidinyl, piperidinyl, morpholinyl or piperazinyl, or R$^a$ and R$^b$, together with the nitrogen atom they are attached to together, form a 5-6 membered heterocyclyl; and each R$^c$ and R$^d$ is independently H, methyl, ethyl, -(n-Pr), -(i-Pr), -(t-Bu), —CHF$_2$, —CF$_3$, —CH$_2$CF$_3$, —CF$_2$CHF$_2$, —CHFCF$_3$, —CF$_2$CF$_3$, —CF$_2$CH$_2$CH$_3$, —CF$_2$CH$_2$CF$_3$, —CF$_2$CH$_2$CHF$_2$, —CH$_2$CHFCH$_3$, —CH$_2$CF$_2$CH$_3$, —CH$_2$CF$_2$CF$_3$, —CH$_2$CF$_2$CHF$_2$, —CH$_2$CH$_2$Cl, cyclopentyl, pyrrolidinyl, piperidinyl, morpholinyl or piperazinyl.

10. The compound of claim 1 having one of the following structures or a stereoisomer, a geometric isomer, a tautomer, an N-oxide, a hydrate, a solvate, or a pharmaceutically acceptable salt thereof:

(1)

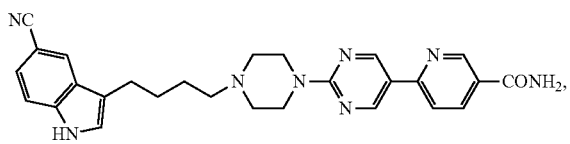

(2)

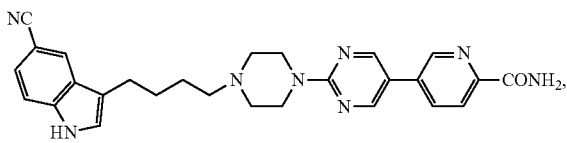

(3)

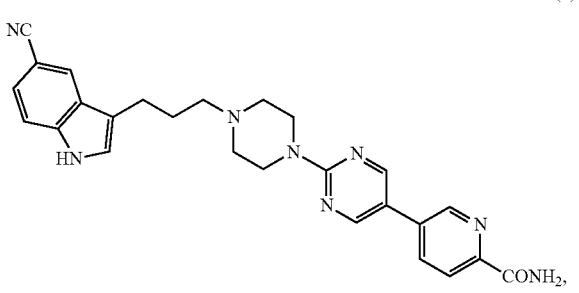

(4)

(5)

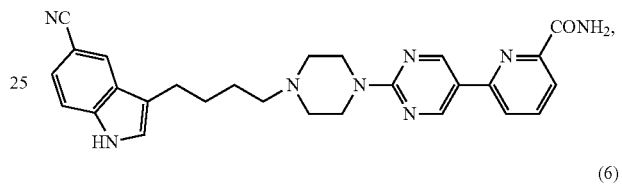

(6)

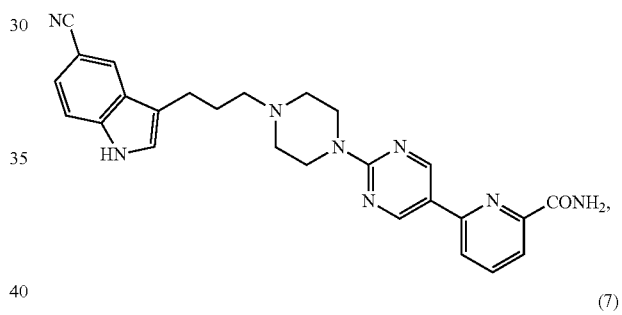

(7)

(8)

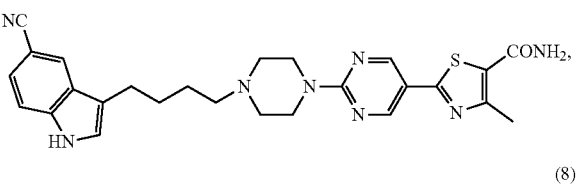

(9)

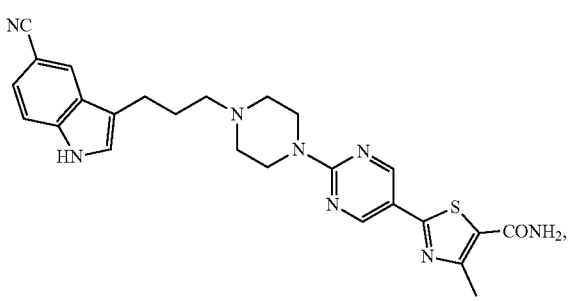

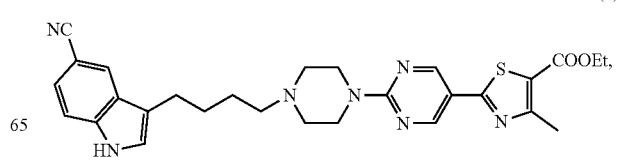

-continued

(10)
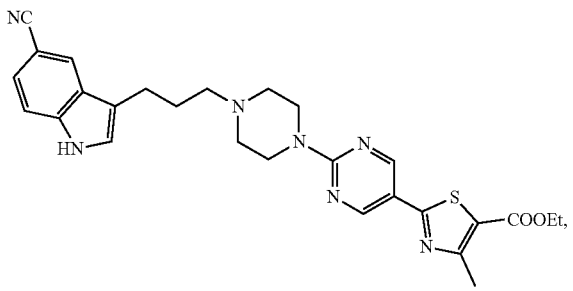

(11)
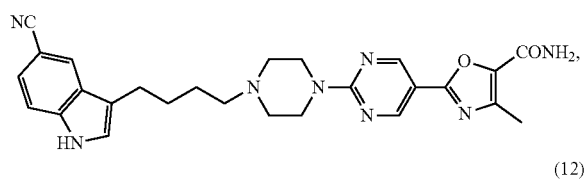

(12)
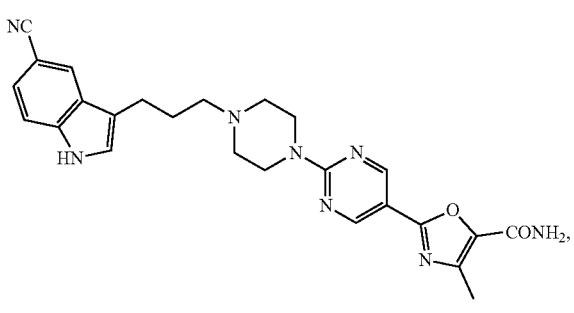

(13)
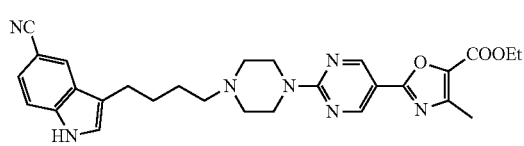

or

(14)
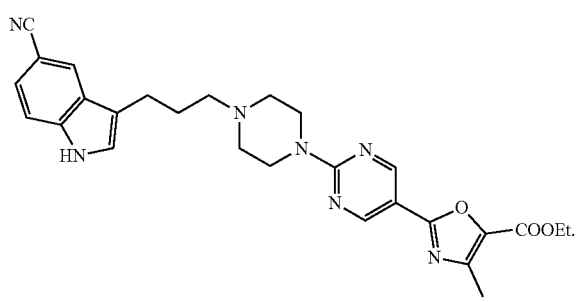

11. A pharmaceutical composition comprising a compound of claim 1;
further comprising pharmaceutically acceptable excipient, carrier, adjuvant, or any combination thereof.

12. The pharmaceutical composition according to claim 11 further comprising a drug for treating central nervous system dysfunction, wherein the drug for treating central nervous system dysfunction is an antidepressant, an anxiolytic, a lithium salt as an emotional stabilizer, an atypical antipsychotic, an antiepileptic drug, an anti-Parkin son's disease drug, a drug as a selective 5-hydroxytryptamine reuptake inhibitor and/or a 5-$HT_{1A}$ receptor agonist, a central nervous stimulant, a nicotinic antagonist or any combination thereof.

13. The pharmaceutical composition according to claim 11, further comprising a drug for treating central nervous system dysfunction, wherein the drug for treating central nervous system dysfunction is amitriptyline, desipramine, mirtazapine, bupropion, reboxetine, fluoxetine, trazodone, sertraline, duloxetine, fluvoxamine, milnacipran, L-minformin, desvenlafaxine, verazolidone, venlafaxine, dapoxetine, nefazodone, femoxetine, clomipramine, citalopram, escitalopram, paroxetine, lithium carbonate, buspirone, olanzapine, quetiapine, risperidone, ziprasidone, aripiprazole, perospirone, clozapine, modafinil, mecamylamine, cabergoline, adamantane, imipramine, pramipexole, thyroxine, dextromethorphan, quinidine, naltrexone, samidorphan, buprenorphine, melatonin, alprazolam, pipamperone, vitatipine, chlordiazepoxide, perphenazine or any combination thereof.

14. A method of treating or lessening central nervous system dysfunction comprising administering a therapeutically effective amount of the compound of claim 1 to the patient.

15. The method of claim 14, wherein the central nervous system dysfunction refers to depression, anxiety, mania, schizophrenia, bipolar disorder, sleep disorder, obsessive-compulsive disorder, panic disorder, post-traumatic stress disorder, dyskinesia, sexual dysfunction, musculoskeletal pain disorder, cognitive disorder, memory disorder, Parkinson's disease, Huntington's disease, phobia, substance abuse or addiction, withdrawal symptoms of drug addiction or premenstral syndrome.

16. A method of inhibiting 5-hydroxytryptamine reuptake; and/or partially activating 5-$HT_{1A}$ receptors comprising administering a therapeutically effective amount of the compound of claim 1 to the patient.

17. A method of, treating or lessening central nervous system dysfunction comprising administering a therapeutically effective amount of the pharmaceutical composition of claim 11 to the patient.

18. The method of claim 17, wherein the central nervous system dysfunction refers to depression, anxiety, mania, schizophrenia, bipolar disorder, sleep disorder, obsessive-compulsive disorder, panic disorder, post-traumatic stress disorder, dyskinesia, sexual dysfunction, musculoskeletal pain disorder, cognitive disorder, memory disorder, Parkinson's disease, Huntington's disease, phobia, substance abuse or addiction, withdrawal symptoms of drug addiction or premenstral syndrome.

19. A method of inhibiting 5-hydroxytryptamine reuptake; and/or partially activating 5-$HT_{1A}$ receptors comprising administering a therapeutically effective amount of the pharmaceutical composition of claim to the patient.

* * * * *